(12) United States Patent
Kroon et al.

(10) Patent No.: US 9,452,179 B2
(45) Date of Patent: Sep. 27, 2016

(54) VESICULAR FORMULATIONS

(71) Applicant: Targeted Delivery Technologies Limited, Valleta (MT)

(72) Inventors: Henk-Andre Kroon, Westport, CT (US); William Henry, Haddenham (GB)

(73) Assignee: Sequessome Technology Holdings Limited, Valletta (MT)

( * ) Notice: Subject to any disclaimer, the term of this patent is extended or adjusted under 35 U.S.C. 154(b) by 0 days.

(21) Appl. No.: 14/055,269

(22) Filed: Oct. 16, 2013

(65) Prior Publication Data

US 2014/0100191 A1     Apr. 10, 2014

Related U.S. Application Data

(63) Continuation of application No. 13/391,326, filed as application No. PCT/US2010/046245 on Aug. 20, 2010, now abandoned.

(60) Provisional application No. 61/235,992, filed on Aug. 21, 2009, provisional application No. 61/314,476, filed on Mar. 16, 2010, provisional application No. 61/320,154, filed on Apr. 1, 2010.

(51) Int. Cl.
| A61K 9/127 | (2006.01) |
| A61K 31/685 | (2006.01) |
| A61K 9/00 | (2006.01) |
| A61K 9/107 | (2006.01) |
| A61K 31/688 | (2006.01) |
| A61K 47/02 | (2006.01) |
| A61K 47/10 | (2006.01) |
| A61K 47/14 | (2006.01) |
| A61K 47/24 | (2006.01) |
| A61K 47/26 | (2006.01) |

(52) U.S. Cl.
CPC ........... *A61K 31/685* (2013.01); *A61K 9/0014* (2013.01); *A61K 9/107* (2013.01); *A61K 9/127* (2013.01); *A61K 31/688* (2013.01); *A61K 47/02* (2013.01); *A61K 47/10* (2013.01); *A61K 47/14* (2013.01); *A61K 47/24* (2013.01); *A61K 47/26* (2013.01)

(58) Field of Classification Search
None
See application file for complete search history.

(56) References Cited

U.S. PATENT DOCUMENTS

| 5,015,483 | A | | 5/1991 | Haynes et al. |
| 5,498,420 | A | | 3/1996 | Edgar et al. |
| 5,498,607 | A | | 3/1996 | Hsai et al. |
| 5,853,753 | A | | 12/1998 | Maierhofer et al. |
| 6,165,500 | A | * | 12/2000 | Cevc ............................ 424/450 |
| 6,191,121 | B1 | | 2/2001 | Perricone |
| 6,248,728 | B1 | | 6/2001 | Koo |
| 6,534,070 | B1 | | 3/2003 | Franke et al. |
| 7,175,850 | B2 | | 2/2007 | Cevc |
| 7,476,432 | B2 | | 1/2009 | Pringle et al. |
| 7,544,375 | B1 | | 6/2009 | Bellin et al. |
| 7,867,480 | B1 | | 1/2011 | Cevc et al. |
| 2002/0012680 | A1 | | 1/2002 | Patel et al. |
| 2003/0064948 | A1 | | 4/2003 | Fahr et al. |
| 2003/0099694 | A1 | * | 5/2003 | Cevc et al. .................... 424/449 |
| 2004/0071767 | A1 | | 4/2004 | Cevc et al. |
| 2004/0105881 | A1 | | 6/2004 | Cevc et al. |
| 2005/0123593 | A1 | | 6/2005 | Thompson et al. |
| 2007/0042008 | A1 | | 2/2007 | Kane et al. |
| 2007/0224256 | A1 | | 9/2007 | Bolton et al. |
| 2007/0238708 | A1 | | 10/2007 | Mandel et al. |
| 2008/0095722 | A1 | | 4/2008 | Cevc et al. |
| 2008/0268042 | A1 | | 10/2008 | Feuerstein et al. |
| 2009/0060990 | A1 | | 3/2009 | Cevc et al. |
| 2009/0324727 | A1 | | 12/2009 | Roca |
| 2010/0098749 | A1 | | 4/2010 | Barenholz et al. |
| 2010/0105139 | A1 | | 4/2010 | Spanjaard |
| 2010/0130611 | A1 | | 5/2010 | Feurstein et al. |
| 2010/0197621 | A1 | | 8/2010 | Henry et al. |
| 2012/0045405 | A1 | | 2/2012 | Gilman et al. |
| 2014/0100191 | A1 | | 4/2014 | Kroon et al. |
| 2015/0057249 | A1 | | 2/2015 | Mayo et al. |
| 2015/0065461 | A1 | | 3/2015 | Garraway et al. |
| 2015/0125407 | A1 | | 5/2015 | Henry et al. |
| 2015/0132349 | A1 | | 5/2015 | Garraway et al. |

FOREIGN PATENT DOCUMENTS

| CN | 1826123 A | 8/2006 |
| EP | 0220797 A2 | 5/1987 |
| EP | 0475160 A1 | 3/1992 |
| EP | 1551370 B1 | 4/2004 |

(Continued)

OTHER PUBLICATIONS

The International Search Report dated Oct. 1, 2010.

(Continued)

*Primary Examiner* — Nannette Holloman

(74) *Attorney, Agent, or Firm* — Fenwick & West LLP

(57) ABSTRACT

Disclosed herein are vesicular formulations that include one or more phospholipids and one or more surfactants and in certain embodiments the use of such formulations for the delivery of fatty acids for the treatment of disorders such as, fatty acid metabolic disorders, including essential fatty acid deficiency; pain or inflammation or osteoarthritis, more specifically for the treatment of deep tissue pain; asthma, bronchospasm, atherothrombatic cardiovascular disorders, avenous thrombatic disorders, inflammatory dermatoses disorders (e.g., atopic eczema, dyshidrotic hand eczema, plaque type psoriasis, seborrheic eczema, and acne vulgaris), and dysmenorrhea.

20 Claims, 31 Drawing Sheets

(56) References Cited

FOREIGN PATENT DOCUMENTS

| | | |
|---|---|---|
| EP | 2382994 A1 | 11/2011 |
| ES | 2107668 T3 | 12/1997 |
| JP | 4-55167 B2 | 9/1992 |
| JP | 7-206879 A | 8/1995 |
| JP | 8-509202 A | 10/1996 |
| JP | 11-139956 A | 5/1999 |
| JP | 2001-523723 A | 11/2001 |
| JP | 2005-515242 A | 5/2005 |
| JP | 2005-179313 A | 7/2005 |
| JP | 2006-528136 A | 12/2006 |
| JP | 2007-269720 A | 10/2007 |
| JP | 2008-127327 A | 6/2008 |
| JP | 2009-506120 A | 2/2009 |
| JP | 2009-256331 A | 11/2009 |
| WO | WO-87/01938 A1 | 4/1987 |
| WO | WO-98/17255 A1 | 4/1998 |
| WO | 0012060 A1 | 3/2000 |
| WO | WO-01/76555 A2 | 10/2001 |
| WO | WO-03/077861 A2 | 9/2003 |
| WO | WO-2004/006954 A2 | 1/2004 |
| WO | WO-2005/007169 A2 | 1/2005 |
| WO | WO-2006/086992 A2 | 8/2006 |
| WO | WO-2008/077641 A1 | 7/2008 |
| WO | 2008/156646 A1 | 12/2008 |
| WO | WO-2008/156646 A1 | 12/2008 |
| WO | WO-2009/093193 A2 | 6/2009 |
| WO | 2009/106338 A2 | 9/2009 |
| WO | WO-2010/140061 A2 | 12/2010 |
| WO | WO-2011/022707 A1 | 2/2011 |
| WO | WO-2011/162802 A1 | 12/2011 |
| WO | WO-2013/144289 A1 | 10/2013 |
| WO | WO-2013/153221 A1 | 10/2013 |
| WO | WO-2013/171131 A1 | 11/2013 |
| WO | WO-2013/171132 A1 | 11/2013 |
| WO | WO-2015/014965 A1 | 2/2015 |

OTHER PUBLICATIONS

The International Preliminary Report on Patentability dated Oct. 24, 2011.
Mezei, et al.; Journal of Pharmaceutical Sciences, (1970); 59:858-861.
Cevc, et al.; Biochemica et Biophysica Acta; (1998); 201-2015.
PCT International Search Report and Written Opinion for PCT/US2010/046245, dated Oct. 1, 2010, 29 Pages.
PCT International Preliminary Report on Patentability for PCT/US2010/046245, dated Oct. 24, 2011, 30 Pages.
PCT International Search Report and Written Opinion for PCT/EP2013/056694, dated Jun. 21, 2013, 8 Pages.
PCT International Search Report and Written Opinion for PCT/IB2010/001557, dated Jun. 6, 2011, 12 Pages.
PCT International Search Report and Written Opinion for PCT/EP2013/057742, dated May 21, 2013.
PCT International Search Report and Written Opinion for PCT/EP2013/059741, dated Jul. 23, 2013, 9 Pages.
PCT International Search Report and Written Opinion for PCT/EP2013/059740, dated Sep. 20, 2013, 19 Pages.
PCT International Search Report and Written Opinion for PCT/EP2014/066545, dated Oct. 15, 2014, 15 Pages.
Barthel, H. R., et al., "Randomized Controlled Trial of Diclofenac Sodium Gel in Knee Osteoarthritis," Semin Arthritis Rheum., 2009, pp. 203-212, vol. 39, No. 3.
Cevc, G., "Transfersomes, Liposomes and Other Lipid Suspensions on the Skin: Permeation Enhancement, Vesicle Penetration, and Transdermal Drug Delivery," Critical Reviews in Therapeutic Drug Carrier Systems, 1996, pp. 257-388, vol. 13, Nos. 3 and 4.
Cevc, G., et al., "Ultraflexible vesicles, Transfersomes, have an extremely low pore penetration resistance and transport therapeutic amounts of insulin across the intact mammalian skin," Biochemica et Biophysica Acta, 1998, pp. 201-215, vol. 1368.
Cevc, G., et al., "Ultradeformable lipid vesicles can penetrate the skin and other semi-permeable barriers unfragmented. Evidence from double label CLSM experiments and direct size measurements," Biochimica et Biophysica Acta, 2002, pp. 21-30.
Crosasso, P., et al., "Preparation, characterization and properties of sterically stabilized paclitaxel-containing liposomes," Journal of Controlled Release, 2000, pp. 19-30.
Dieppe, P. et al., "Pathogenesis and management of pain in osteoarthritis," The Lancet, 2005, pp. 965-973, vol. 365.
Bayer: Bepanthen-Spray Mousse Rafraichissant (patient information leaflet), Dec. 10, 2007, XP002636839.
Gallarate, M., et al., "Deformable Liposomes as Topical Formulations Containing α-Tocopherol," Journal of Dispersion Science and Technology, 2006, pp. 703-713, vol. 27, No. 5.
Idea AG, "Updates on Diractin® (ketoprofen in Transfersome® gel) status," Oct. 7, 2009, Munich, Germany.
Idea AG, "Multicenter, Randomized, Double-Blind, Placebo- and Active-Controlled Study of Safety and Efficacy of Two Dosages of Epicutaneously Applied Diractin® (Ketoprofen in Transfersome® Gel) for the Treatment of Osteoarthritis of the Knee," In: ClinicalTrials.gov [Internet], Bethesda (US): National Library of Medicine (US), Apr. 26, 2016, Available from: https://clinicaltrials.gov/archive/NCT00716547/2009_01_20.
Kawano, T., et al., "Mechanical Effects of the Intraarticular Administration of High Molecular Weight Hyaluronic Acid Plus Phospholipid on Synovial Joint Lubrication and Prevention of Articular Cartilage Degeneration in Experimental Osteoarthritis," Arthritis & Rheumatism, 2003, pp. 1923-1929, vol. 48, No. 7.
Lahey Hospital & Medical Center, "Lecithin," 2016, 6 Pages.
Mezei, M., et al., "Dermatitic Effect of Nonionic Surfactants IV: Phospholipid Composition of Normal and Surfactant-Treated Rabbit Skin," Journal of Pharmaceutical Sciences, 1970, pp. 858-861, vol. 59, No. 6.
Sivan, S., et al, "Liposomes Act as Effective Biolubricants for Friction Reduction in Human Synovial Joints," Langmuir, 2010, pp. 1107-1116, vol. 26, No. 2.
Simões, S. I., et al., Permeabilisation and solubilisation of soybean phosphatidylcholine bilayer vesicles, as membrane models, by polysorbate, Tween 80, European Journal of Pharmaceutical Sciences, 2005, pp. 307-317, vol. 26.
Skalko, N., et al., "Liposomes with Metronidazole for Topical Use: The Choice of Preparation Method and Vehicle," Journal of Liposome Research, 1998, pp. 283-293, vol. 8, No. 2.
Sumida, Y., "Application of a Liposome Technique to Cosmetics," Membrane, 1998, pp. 144-152, vol. 24, No. 3. (English abstract).
Treede, I., et al., "Anti-Inflammatory Effects of Phosphatidylcholine," The Journal of Biological Chemistry, 2007, pp. 27155-27164, vol. 282, No. 37.
Withdrawal Assessment Report for Diractin; EMEA—European Medicines Agency, Oct. 23, 2008, London, UK, 24 Pages.
United States Office Action, U.S. Appl. No. 13/375,155, dated Jul. 16, 2015, 8 Pages.
United States Office Action, U.S. Appl. No. 13/391,326, dated Jul. 6, 2015, 7 Pages.
United States Office Action, U.S. Appl. No. 14/055,269, dated Jul. 1, 2015, 7 Pages.
United States Office Action, U.S. Appl. No. 14/388,469, dated Mar. 8, 2016, 8 Pages.
United States Office Action, U.S. Appl. No. 14/400,866, dated Mar. 11, 2016, 6 Pages.

* cited by examiner

AEs by System Organ Class (SOC)
Drug Related Adverse Event by Organ Class System; ITT Population

|  | Ketoprofen | | Placebo | |
| --- | --- | --- | --- | --- |
|  | Absolute | Percent | Absolute | Percent |
| Eye disorders | 1 | 1.5 | 0 | 0.0 |
| Gastrointestinal disorders | 2 | 3.0 | 5 | 7.6 |
| General disorders and administration site conditions | 1 | 1.5 | 2 | 3.0 |
| Injury, poisoning and procedural complications | 2 | 3.0 | 0 | 0.0 |
| Infections and infestations | 0 | 0.0 | 1 | 1.5 |
| Investigations | 11 | 16.4 | 4 | 6.1 |
| Musculoskeletal and connective tissue disorders | 4 | 6.0 | 4 | 6.1 |
| Nervous system disorders | 5 | 7.5 | 9 | 13.6 |
| Skin and subcutaneous tissue disorders | 39 | 58.2 | 40 | 60.6 |
| Vascular disorders | 2 | 3.0 | 1 | 1.5 |
| Total | 67 | 100.0 | 66 | 100.0 |

FIG. 2

Use of rescue medication - Descriptive statistics

Intake of Analgesics during Treatment Period; ITT Population

CROSSTABULATION

| Scores Groups | No | Yes | Valid No. | Mean Rank |
|---|---|---|---|---|
| 100mg Keto (N = 274) | 49 17.88% | 225 82.12% | 274 | 279.874 |
| 100mg Plac (N = 281) | 54 19.22% | 227 80.78% | 281 | 276.173 |

%: row percent

Mean Intake of Analgesics (Days); ITT Population

Descriptive Statistics

| Groups | Mean | Valid No. |
|---|---|---|
| 100mg Keto (N = 274) | 13.1 | 274 |
| 100mg Plac (N = 281) | 13.1 | 281 |

FIG. 5

Possibly treatment related Aes by SOC (>1% in any group)

| Body System | 50mg Ketoprofen N=233 | | | 50mg Placebo Gel N=238 | | | 100mg Ketoprofen N=230 | | | 100mg Placebo Gel N=234 | | | 100mg Celecoxib N=233 | | | Oral Placebo N=227 | | |
|---|---|---|---|---|---|---|---|---|---|---|---|---|---|---|---|---|---|---|
| | AE | PAT | % | AE | PAT | % | AE | PAT | % | AE | PAT | % | AE | PAT | % | AE | PAT | % |
| Body Gastrointestinal | 4 | 3 | 1.3 | 2 | 2 | 0.8 | 3 | 3 | 1.3 | 8 | 7 | 3.0 | 53 | 37 | 15.9 | 46 | 33 | 14.5 |
| Nervous System | | | | 7 | 3 | 1.3 | | | | 1 | 1 | 0.4 | 2 | 2 | 0.9 | 6 | 5 | 2.2 |
| Skin/subcutaneous | 13 | 13 | 5.6 | 16 | 14 | 5.9 | 33 | 28 | 12.2 | 28 | 26 | 11.1 | 5 | 5 | 2.1 | 2 | 2 | 0.9 |
| Vascular | 1 | 1 | 0.4 | 3 | 2 | 0.8 | | | | 1 | 1 | 0.4 | 4 | 4 | 1.7 | 1 | 1 | 0.4 |

FIG. 17

VESICULAR FORMULATIONS

CROSS REFERENCE TO RELATED APPLICATION

This application is a continuation of application Ser. No. 13/391,326, entitled "Vesicular Formulations", filed Jun. 1, 2012, which was the 35 U.S.C. §371 national stage of PCT application entitled "Vesicular Formulations," having serial number PCT/US2010/046245, filed on 20 Aug. 2010, which claims priority to and benefit of U.S. Provisional Application No. 61/235,992, filed on Aug. 21, 2009, U.S. Provisional Application No. 61/314,476, filing date Mar. 16, 2010 and U.S. Provisional Application No. 61/320,154, filing date Apr. 1, 2010, each incorporated by reference in their entirety.

FIELD OF INVENTION

The present invention relates to formulations of phospholipids and surfactants and to the use of such formulations for the delivery of fatty acids for the treatment of disorders such as, fatty acid metabolic disorders, including essential fatty acid deficiency; pain or inflammation or osteoarthritis, more specifically for the treatment of deep tissue pain; asthma, bronchospasm, atherothrombatic cardiovascular disorders, avenous thrombatic disorders, inflammatory dermatoses disorders (e.g., atopic eczema, dishydrotic hand eczema, plaque type psoriasis, seborrheic eczema, and acne vulgaris), and dysmenorrhea.

BACKGROUND

U.S. Pat. No. 6,165,500 to Cevc describes a "preparation for the application of agents . . . provided with membrane-like structures consisting of one or several layers of amphiphilic molecules, or an amphiphilic carrier substance, in particular for transporting the agent into and through natural barriers such as skin and similar materials." Abstract. These transfersomes "consist of one or several components[, m]ost commonly a mixture of basic substances, one or several edge-active substances, and agents [ ]." Col. 5, lines 28-30. According to U.S. Pat. No. 6,165,500, "[l]ipids and other amphiphiles are best suited basic substances; surfactants or suitable solvents are the best choice from the point of view of edge-active substances[, and a]ll of these can be mixed with agents in certain proportions depending both on the choice of the starting substances and on their absolute concentration." Col. 5, lines 30-35.

U.S. Patent Application Publication No. US 2004/0071767 to Cevc et al. describes "formulations of nonsteroidal anti-inflammatory drugs (NSAIDs) based on complex aggregates with at least three amphiphatic components suspended in a . . . pharmaceutically acceptable . . . medium." Abstract. "One of these components is capable of forming stable, large bilayer membranes on its own. The other at least two amphiphatic components, including an NSAID, tend to destabilise such membranes." Paragraph [0002].

U.S. Patent Application Publication No. US 2004/0105881 to Cevc et al. describes extended surface aggregates, "suspendable in a suitable liquid medium and comprising at least three amphiphats (amphiphatic components) and being capable to improve the transport of actives through semi-permeable barriers, such as the skin, especially for the non-invasive drug application in vivo by means of barrier penetration by such aggregates." Paragraph [0002]. "The three amphiphats include at least one membrane forming compound (MFC), which can form the membrane of [the aggregates], and at least two membrane destabilising compounds ($MDC_1$ and $MDC_2$) differentiated by their capability of forming smaller aggregates (with no extended surfaces) by either themselves or else in combination with each other and/or characterized by their relatively high solubility in [the] suitable liquid medium. Paragraph [0002]. US 2004/0105881 specifically discloses that "incorporation of a surfactant into a bilayer membrane that is built from another less soluble amphiphat, such as a phospholipid, can increase the flexibility of the resulting complex membrane . . . promot[ing] the capability of complex aggregates . . . to cross pores in a semi-permeable membrane that otherwise would prevent comparably large aggregates from crossing." Paragraph [0015]. Citation of any reference in this section of the application is not an admission that the reference is prior art to the application. The above noted publications are hereby incorporated by reference in their entirety.

SUMMARY OF THE INVENTION

The invention encompasses vesicular formulations comprising one or more phospholipids and one or more nonionic surfactants that are effective for the delivery of fatty acids and/or phospholipids in the treatment of disorders related to fatty acid metabolic disorders, including essential fatty acid deficiency. In a particular embodiment, the vesicular formulations comprise about 25% to about 30% surfactant by weight based on the total weight of the vesicular formulation. These vesicular formulations are suitable for any method of administration, e.g., subcutaneously, topically, or intravenously.

In accordance with the present invention, the vesicular formulations of the invention are formulated to deliver fatty acids and phosphatidyl derivatives of fatty acids, such as arachidonic acid or omega-3 or omega-6 fatty acids. In accordance with this embodiment the vesicular formulations may optionally be formulated to include other lipids described herein, such as phophatidyl choline, and surfactants. In accordance with the present invention, the vesicular formulations of the invention deliver essential fatty acids, such as omega-3 fatty acids, to decrease the levels of triglycerides. Vesicular formulations of the invention which deliver essential fatty acids, such as omega-3 fatty acids, may be useful in the treatment of fatty acid metabolic disorders, such as essential fatty acid deficiency and hypertriglyceridemia. In one embodiment, the vesicular formulations which deliver essential fatty acids comprise a phosphatidylchloline derivative of a fatty acid, e.g., a phosphatidylcholine derivative of an omega-3 fatty acid. In various embodiments, the vesicular formulation is one of the formulations set forth in Example Formulations 1-129.

"Fatty acid metabolic disorder" means a defect in one of the enzymes involved in fatty acid metabolism, and include fatty oxidation disorders, whereby the body is unable to oxidize and metabolize fatty acids due to a failure in the enzymatic pathway. "Essential fatty acid deficiency" means a deficiency in the essential fatty acids, e.g., omega-3 and omega-6 fatty acids, which can lead to physical symptoms such as hemorrhagic dermatitis skin atrophy, scaly dermatitis, dry skin, weakness, impaired vision, tingling sensations, mood swings, edema, high blood pressure, high triglycerides, hemorrhagic folliculitis, hemotologic disturbances, immune and mental deficiencies, and impaired growth.

In accordance with the present invention, the vesicular formulations of the invention deliver fats and fat soluble vitamins, such as vitamin E, for the treatment of disorders related to hypolididemia, including, abetalipoproteinemia, hypobetalipoproteinemia, chlyomicron retention disease. In one embodiment, the vesicular formulations which deliver fats and fat soluble vitamins comprise a phosphatidylcholine derivative of a fatty acid, e.g., a phosphatidylcholine derivative of vitamin E. In various embodiments, the vesicular formulation is one of the formulations set forth in Example Formulations 1-129.

The invention encompasses vesicular formulations comprising one or more phopholipids and one or more nonionic surfactants that are effective in sequestering organic matter once delivered to the subject. These vesicular formulations are suitable for any method of administration, e.g., subcutaneously, topically, or intravenously. Without in any way being limited by theory, it is believed that the surprisingly effective and capacious sequestration of native organic compounds by the vesicular formulations disclosed herein occurs because of liquid crystallinity of the vesicular formulations mediated by the presence of membrane adapters such as surfactants. In various embodiments, the vesicular formulation is one of the formulations set forth in Example Formulations 1-129. In a preferred embodiments, the vesicular formulations comprise about 25% to about 30% surfactant by weight.

In one embodiment, the invention encompasses vesicular formulations of lipids and surfactants capable of sequestering native organic compounds, including arachidonic acid, upon delivery to human skin for the treatment of pain or inflammation. In some embodiments, these formulations are designed such that the vesicles are able to penetrate deep tissue without diversion into the blood vessels. That is, the formulations are able to travel to the site of the pain in sufficient amount to alleviate that pain to some extent. In accordance with the invention, delivery to the deep tissue includes delivery of the formulation beneath the skin to the muscle tissue and to the joint itself, while limiting systemic delivery and exposure to the formulation. In a particular embodiment, the vesicular formulation is capable of sequestering arachidonic acid upon administration to human skin, and therefore is capable of altering the pathology of, e.g., pain or inflammation. In another embodiment of the invention, vesicular formulations designed to sequester arachidonic acid may also be used to prevent the formation of metabolites, including eicosanoids, for the prevention and/or treatment of asthma, seborrheic eczema, bronchospasm, atherothrombatic cardiovascular disorders, venous thrombatic disorders, pain, and dysmenorrhea. In various embodiments, the vesicular formulation capable of sequestering arachidonic acid is one of the formulations set forth in Example Formulations 1-129.

In an embodiment of the invention, vesicular formulations comprising one or more phospholipids and one or more nonionic surfactants can sequester cholesterol upon administration to human skin, thus decreasing the accumulation of or uptake of cholesterol for the treatment of hypercholesterolemia. The invention relates to vesicular formulations comprising one or more phospholipids and one or more nonionic surfactants that are effective in sequestering triglycerides, thus decreasing the accumulation or uptake of triglycerides for the treatment of hypertriglyceridemia. In various embodiments, the vesicular formulation capable of sequestering cholesterol or triglycerides is one of the formulations set forth in Example Formulations 1-129.

The vesicular formulations of the invention may also be used to sequester factors involved in fatty acid metabolism, such as hormone sensitive lipase (HSL). Inhibition of HSL inhibits the conversion of triglycerides to glycerol and fatty acids, resulting in a decrease in plasma free fatty acids. Thus, the vesicular formualtions of the invention have utility where the decrease in plasma fatty acids is desired, including insulin resistance, metabolic syndrome X, dyslipidemias and abnormal lipoprotein metabolism. In various embodiments, the vesicular formulation capable of sequestering factors involved in fatty acid metabolism is one of the formulations set forth in Example Formulations 1-129.

The invention relates to vesicular formulations comprising one or more phospholipids and one or more nonionic surfactants that are effective in sequestering metal (as a chelator) upon administration to human skin for the treatment of, e.g., metal toxicity. In various embodiments, the vesicular formulation capable of sequestering metals is one of the formulations set forth in Example Formulations 1-129.

The invention relates to vesicular formulations comprising one or more phospholipids and one or more nonionic surfactants that are effective in sequestering a toxin (e.g., DDT) upon administration to human skin. In various embodiments, the vesicular formulation capable of sequestering toxins such as DDT is one of the formulations set forth in Example Formulations 1-129.

The invention relates to vesicular formulations comprising one or more phospholipids and one or more nonionic surfactants that are effective in sequestering inflammatory mediators (e.g., cytokines, such as interleukins, or presenting antigens) upon administration to human skin for the treatment of inflammation and inflammatory related disorders, such as asthma. In various embodiments, the vesicular formulation capable of sequestering inflammatory mediators is one of the formulations set forth in Example Formulations 1-129.

The invention relates to vesicular formulations comprising one or more phospholipids and one or more nonionic surfactants that are effective in sequestering amyloid upon administration for the treatment of Alzheimers disease. Such formulations may be administered intravenously in accordance with this embodiment. In various embodiments, the vesicular formulation capable of sequestering amyloid is one of the formulations set forth in Example Formulations 1-129.

The invention relates to vesicular formulations comprising one or more phospholipids and one or more nonionic surfactants that are effective in sequestering uric acid upon administration for the treatment of gout or macular degeneration, such as AMD. Such formulations may be administered topically or intravitreally in accordance with this embodiment. In various embodiments, the vesicular formulation capable of sequestering uric acid is one of the formulations set forth in Example Formulations 1-129.

The invention relates to vesicular formulations comprising one or more phospholipids and one or more nonionic surfactants that are effective in sequestering squalene, thus leading to fungistatic activity against, e.g., hyphal fungi. These vesicular formulations are suitable for any method of administration, e.g., subcutaneously, topically, or intravenously. In various embodiments, the vesicular formulation capable of sequestering squalene is one of the formulations set forth in Example Formulations 1-129.

The formulations of the invention are formulated in the absence of any pharmaceutically active agent, i.e., any non-lipid non-surfactant pharmaceutically active agent.

As used herein, the term "formulation" is not meant to imply that the ingredients or components are in combination with a pharmaceutically active agent, i.e., any non-lipid non-surfactant active agent that has received regulatory approval for the treatment of fatty acid related disorders, hypocholesterolemia, hypertriclyceridemia, pain, including osteoarthritic pain, inflammation, infection, or toxicity, including metal toxicity or any of the disorders listed above.

Despite the lack of a recognized active agent, the vesicles elicit a therapeutic effect, namely the treatment of disorders related to fatty acid deficiencies, fatty acid metabolism, hypertriglyceridemia and hypercholesterolemia, or any of the disorders listed above. Without being bound by any theory, Applicant believes that the vesicle components themselves are responsible for this effect.

In one embodiment, the invention provides a pharmaceutical package or kit comprising one or more containers filled with the formulation of the invention, and instructions for administration of the formulation to a patient or subject in need thereof for the treatment of any disorders related to fatty acid deficiencies, fatty acid metabolism, hypertriglyceridemia and hypercholesterolemia, or any of the disorders listed above. In certain embodiments, the formulation comprises one or more phospholipids and one or more surfactants. In certain embodiments, the formulation does not comprise a pharmaceutically active agent, i.e., any non-lipid, non-surfactant pharmaceutically active agent that has received marketing or regulatory approval in any country for the treatment of disorders related to fatty acid deficiencies, fatty acid metabolism, hypertriglyceridemia, hypercholesterolemia, pain, including osteoarthritic pain, inflammation, infection, including fungal or bacterial infection, or toxicity, including metal toxicity, or any of the other disorders listed above. In various embodiments, the container comprises a formulation formulated as a suspension, emulsion, gel, cream, lotion, spray, film forming solution or lacquer. The invention provides packages or kits that can be used in any of the above-described methods.

In one embodiment, the invention comprises a method for the treatment of disorders related to fatty acid deficiencies, fatty acid metabolism, hypertriglyceridemia, hypercholesterolemia, or any of the disorders listed above, wherein the vesicular formulations of the invention are administered over a period of one or more weeks, for example for at least five weeks, six weeks, seven weeks, eight weeks, nine weeks, ten weeks, eleven weeks, or twelve weeks, sixteen weeks, twenty four weeks, four months, six months, eight months, ten months, one year, two or more years, or indefinitely.

In one embodiment, the formulations of the invention comprise one or more phospholipids, one or more nonionic surfactants, in the absence of any pharmaceutically active agent, i.e., any non-lipid non-surfactant pharmaceutically active agent that has received regulatory approval for the treatment of disorders related to fatty acid deficiencies, fatty acid metabolism, hypertriglyceridemia, hypercholesterolemia pain, including osteoarthritic pain, inflammation, infection, including fungal or bacterial infection, or toxicity, including metal toxicity, or any of the disorders listed above.

In one embodiment, a 0.1 to 10 gram dose of the formulation of the invention is administered to the patient for the treatment of disorders related to fatty acid deficiencies, fatty acid metabolism, hypertriglyceridemia and hypercholesterolemia, or any of the disorders listed above; a 1 to 10 gram dose of the formulation is administered to the patient for the treatment of disorders related to fatty acid deficiencies, fatty acid metabolism, hypertriglyceridemia, hypercholesterolemia, or any of the disorders listed above; a 1 to 5 gram dose of the formulation is administered to the patient for the treatment of disorders related to fatty acid deficiencies, fatty acid metabolism, hypertriglyceridemia, hypercholesterolemia, pain, including osteoarthritic pain, inflammation, infection, including fungal or bacterial infection, or toxicity, including metal toxicity, or any of the disorders listed above; or a 1 gram, 2 gram, 3 gram, 4 gram, 5 gram, 6 gram, 7 gram, 8 gram, 9 gram or 10 gram dose of the formulation is administered to the patient for the treatment of disorders related to fatty acid deficiencies, fatty acid metabolism, hypertriglyceridemia, hypercholesterolemia pain, including osteoarthritic pain, inflammation, infection, including fungal or bacterial infection, or toxicity, including metal toxicity, or any of the disorders listed above. In some embodiments, the dose is measured as the total weight of the deformasome. In some embodiments, the dose is measured as the total weight of the lipid(s) and surfactant(s) in the deformasome. The dose may be administered once or twice daily for the treatment of disorders related to fatty acid deficiencies, fatty acid metabolism, hypertriglyceridemia and hypercholesterolemia, or any of the disorders listed above. The dose may be administered once, twice, three, four, five, six, or seven times per week in accordance with the invention. The dose may be administered every day, every other day, or two to three times a week in accordance with the invention.

In some embodiments, the lipid in the pharmaceutical composition is a phospholipid. In some embodiments, the second lipid is a lysophospholipid. In some embodiments, the surfactant is a non-ionic surfactant.

In some embodiments, the compositions of the invention form vesicles or other extended surface aggregates (ESAs), wherein the vesicular preparations have improved permeation capability through the semi-permeable barriers, such as skin. The adapatability and deformability of the vesicles allow the vesicles to penetrate beneath the skin to the muscle and the joint itself, however, the size of the vesicle prevents penetration into the vasculature and as a result prevents systemic delivery. While not to be limited to any mechanism of action, the formulations of the invention are able to form vesicles characterized by their deformability and/or adaptability. The adaptability or deformability of the vesicles may be determined by the ability of the vesicles to penetrate a barrier with pores having an average pore diameter at least 50% smaller than the average vesicle diameter before the penetration.

In some embodiments, the vesicular compositions of the invention provide for targeted delivery of e.g., fatty acids to phospholipase-rich sites, e.g., tissues that are part of an inflammatory process or sites containing microorganisms such as bacteria (including narcadia) or fungi. While not to be limited to any mechanism of action or by any theory, the vesicular compositions of the invention are broken down by phospholipases. Thus, phospholipases that are released as part of the inflammatory process (e.g., cancer or asthma) or that are released upon contact with a microorganism such as bacteria or fungi can lead to a number of effects including but not limited to rapid entry of the vesicular compositions into the target tissue, changes in the intracellular or intramembraneous lipid homeostasis, which may lead to increased apoptosis or altered membrane function, including increased permeability, and rapid metabolism of the vesicular composition with release of its constituents.

BRIEF DESCRIPTION OF THE DRAWINGS

The present invention is described with reference to the following examples and figures in which;

FIG. 2 shows the results of example 2 (United States study) and provides the incidents of adverse events by organ class system.

FIG. 5 shows the results of example 2 (United States study) and provides descriptive statistics for the use of rescue medication.

FIG. 17 shows the results of example 2 (European study) and shows possibly treatment related adverse events (AES) observed in the study.

DETAILED DESCRIPTION OF THE INVENTION

Figure 1A:
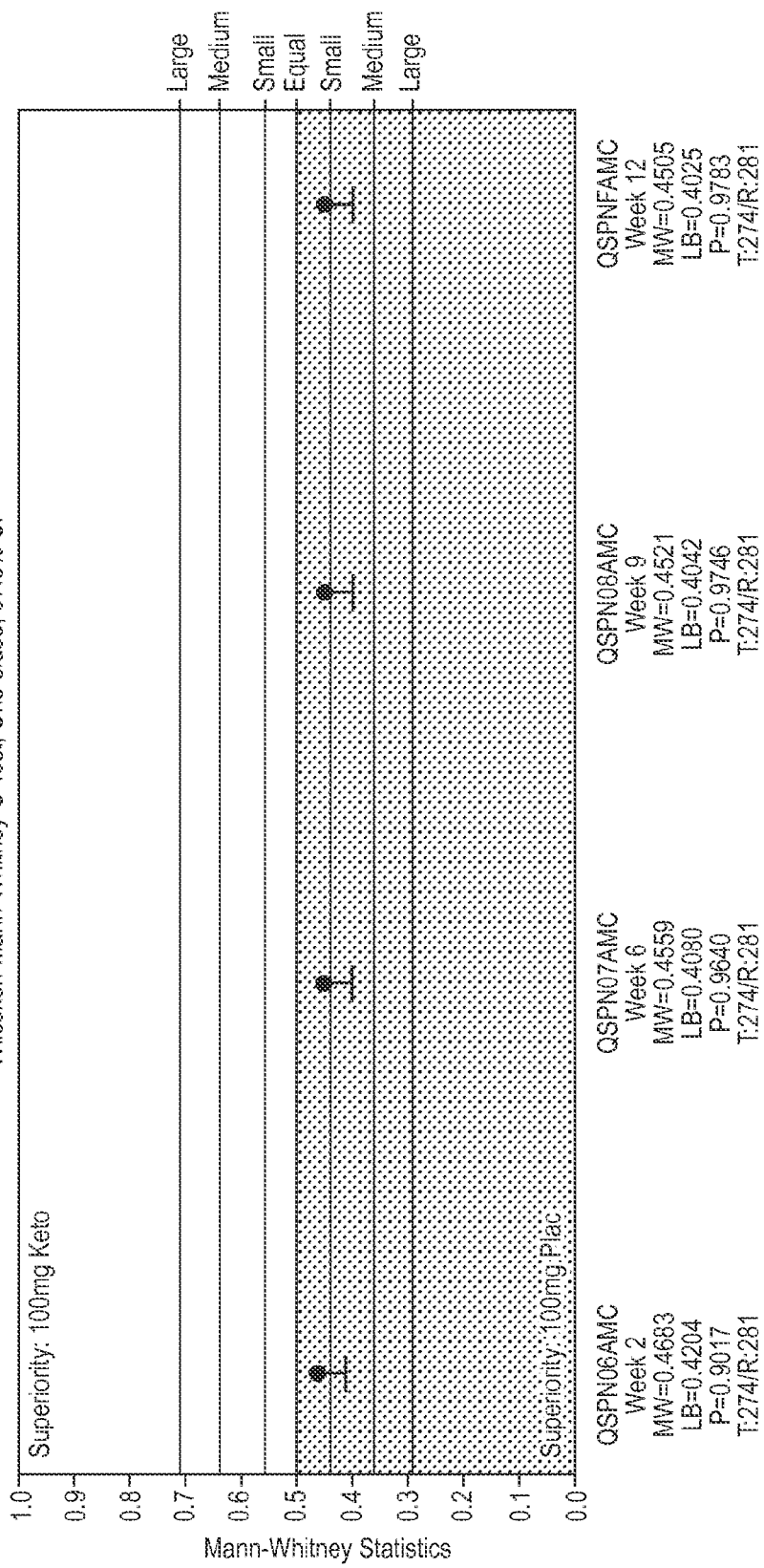
FIG. 1A shows the results of example 2 (United States study) and provides Mann-Whitney statistics and continuous responder analysis of pain measurements in patients, analysed by randomised Wilcoxon-Mann-Whitney-U test.

Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, sheep, goat, pig, horse, dog, cat, rabbit, rat, or mouse. The terms "subject" and "patient" are used interchangeably herein in reference, for example, to a mammalian subject, such as a human subject.

As used herein, a "sufficient amount," "amount effective to" or an "amount sufficient to" achieve a particular result refers to an amount of the formulation of the invention is effective to produce a desired effect, which is optionally a therapeutic effect (i.e., by administration of a therapeutically effective amount). Alternatively stated, a "therapeutically effective" amount is an amount that provides some alleviation, mitigation, and/or decrease in at least one clinical symptom. Clinical symptoms associated with the disorder that can be treated by the methods of the invention are well-known to those skilled in the art. Further, those skilled in the art will appreciate that the therapeutic effects need not be complete or curative, as long as some benefit is provided to the subject. For example, a "sufficient amount" or "an amount sufficient to" can be an amount that is effective to treat the symptoms of fatty acid deficiencies, hypertriglyceridemia or hypercholesterolemia or other joint or muscle pain.

As used herein, the terms "treat", "treating" or "treatment of" mean that the severity of a subject's condition is reduced or at least partially improved or ameliorated and/or that some alleviation, mitigation or decrease in at least one clinical symptom is achieved and/or there is an inhibition or delay in the progression of the condition and/or delay in the progression of the onset of disease or illness. The terms "treat", "treating" or "treatment of" also means managing the disease state.

As used herein, the term "pharmaceutically acceptable" when used in reference to the formulations of the invention denotes that a formulation does not result in an unacceptable level of irritation in the subject to whom the formulation is administered. Preferably such level will be sufficiently low to provide a formulation suitable for approval by regulatory authorities.

As used herein with respect to numerical values, the term "about" means a range surrounding a particular numeral value which includes that which would be expected to result from normal experimental error in making a measurement. For example, in certain embodiments, the term "about" when used in connection with a particular numerical value means ±20%, unless specifically stated to be ±1%, ±2%, ±3%, ±4%, ±5%, ±10%, ±15%, or ±20% of the numerical value.

The term "alkyl" refers to a linear or branched saturated monovalent hydrocarbon radical, wherein the alkyl may optionally be substituted with one or more substituents Q as described herein. The term "alkyl" also encompasses both linear and branched alkyl, unless otherwise specified. In certain embodiments, the alkyl is a linear saturated monovalent hydrocarbon radical that has 1 to 20 ($C_{1-20}$), 1 to 15 ($C_{1-15}$), 1 to 12 ($C_{1-12}$), 1 to 10 ($C_{1-10}$), or 1 to 6 ($C_{1-6}$) carbon atoms, or a branched saturated monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms. It is understood in the chemical arts, that the use of the longer chains described herein may be appropriate, or appropriate only in limited amounts, within a molecule so that the properties of the resulting molecule (such as solubility) are appropriate for the use. Thus, while those in the art may use the above longer length alkyl substituents they will be used only when appropriate to provide the desired function.

The term "aryl" refers to a monocyclic aromatic group and/or multicyclic monovalent aromatic group that contain at least one aromatic hydrocarbon ring. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In certain embodiments, aryl may also be optionally substituted with one or more substituents Q as described herein.

The term "heteroaryl" refers to a monocyclic aromatic group and/or multicyclic aromatic group that contain at least one aromatic ring, wherein at least one aromatic ring contains one or more heteroatoms independently selected from O, S, and N. Each ring of a heteroaryl group can contain one or two O atoms, one or two S atoms, and/or one to four N atoms, provided that the total number of heteroatoms in each ring is four or less and each ring contains at least one carbon atom. The heteroaryl may be attached to the main structure at any heteroatom or carbon atom which results in the creation of a stable compound. In certain embodiments, the heteroaryl has from 5 to 20, from 5 to 15, or from 5 to 10 ring atoms. Examples of monocyclic heteroaryl groups include, but are not limited to, pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, and triazinyl. Examples of bicyclic heteroaryl groups include, but are not limited to, indolyl, benzothiazolyl, benzoxazolyl, benzothienyl, quinolinyl, tetrahydroisoquinolinyl, isoquinolinyl, benzimidazolyl, benzopyranyl, indolizinyl, benzofuranyl, isobenzofuranyl, chromonyl, coumarinyl, cinnolinyl, quinoxalinyl, indazolyl, purinyl, pyrrolopyridinyl, furopyridinyl, thienopyridinyl, dihydroisoindolyl, and tetrahydroquinolinyl. Examples of tricyclic heteroaryl groups include, but are not limited to, carbazolyl, benzindolyl, phenanthrollinyl, acridinyl, phenanthridinyl, and xanthenyl. In certain embodiments, heteroaryl may also be optionally substituted with one or more substituents Z as described herein.

The term "alkenoyl" as used herein refers to —C(O)-alkenyl. The term "alkenyl" refers to a linear or branched monovalent hydrocarbon radical, which contains one or more, in one embodiment, one to five, carbon-carbon double bonds. The alkenyl may be optionally substituted with one or more substituents Z as described herein. The term "alkenyl" also embraces radicals having "cis" and "trans" configurations, or alternatively, "Z" and "E" configurations, as appreciated by those of ordinary skill in the art. As used herein, the term "alkenyl" encompasses both linear and branched alkenyl, unless otherwise specified. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 30 ($C_{2-30}$), 2 to 24 ($C_{2-24}$), 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched monovalent hydrocarbon radical of 3 to 30 ($C_{3-30}$), 3 to 24 ($C_{3-24}$), 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl. In certain embodiments, the alkenoyl is mono-alkenoyl, which contains one carbon-carbon double bond. In certain embodiments, the alkenoyl is di-alkenoyl, which contains two carbon-carbon double bonds. In certain embodiments, the alkenoyl is poly-alkenoyl, which contains more than two carbon-carbon double bonds.

The term "heterocyclyl" or "heterocyclic" refers to a monocyclic non-aromatic ring system and/or multicyclic ring system that contains at least one non-aromatic ring, wherein one or more of the non-aromatic ring atoms are heteroatoms independently selected from O, S, or N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. In certain embodiments, the heterocyclyl is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic radicals include, but are not limited to, acridinyl, azepinyl, benzimidazolyl, benzindolyl, benzoisoxazolyl, benzisoxazinyl, benzodioxanyl, benzodioxolyl, benzofuranonyl, benzofuranyl, benzonaphthofuranyl, benzopyranonyl, benzopyranyl, benzotetrahydrofuranyl, benzotetrahydrothienyl, benzothiadiazolyl, benzothiazolyl, benzothiophenyl, benzotriazolyl, benzothiopyranyl, benzoxazinyl, benzoxazolyl, benzothiazolyl, β-carbolinyl, carbazolyl, chromanyl, chromonyl, cinnolinyl, coumarinyl, decahydroisoquinolinyl, dibenzofuranyl, dihydrobenzisothiazinyl, dihydrobenzisoxazinyl, dihydrofuryl, dihydropyranyl, dioxolanyl, dihydropyrazinyl, dihydropyridinyl, dihydropyrazolyl, dihydropyrimidinyl, dihydropyrrolyl, dioxolanyl, 1,4-dithianyl, furanonyl, furanyl, imidazolidinyl, imidazolinyl, imidazolyl, imidazopyridinyl, imidazothiazolyl, indazolyl, indolinyl, indolizinyl, indolyl, isobenzotetrahydrofuranyl, isobenzotetrahydrothienyl, isobenzothienyl, isochromanyl, isocoumarinyl, isoindolinyl, isoindolyl, isoquinolinyl, isothiazolidinyl, isothiazolyl, isoxazolidinyl, isoxazolyl, morpholinyl, naphthyridinyl, octahydroindolyl, octahydroisoindolyl, oxadiazolyl, oxazolidinonyl, oxazolidinyl, oxazolopyridinyl, oxazolyl, oxiranyl, perimidinyl, phenanthridinyl, phenathrolinyl, phenarsazinyl, phenazinyl, phenothiazinyl, phenoxazinyl, phthalazinyl, piperazinyl, piperidinyl, 4-piperidonyl, pteridinyl, purinyl, pyrazinyl, pyrazolidinyl, pyrazolyl, pyridazinyl, pyridinyl, pyridopyridinyl, pyrimidinyl, pyrrolidinyl, pyrrolinyl, pyrrolyl, quinazolinyl, quinolinyl, quinoxalinyl, quinuclidinyl, tetrahydrofuryl, tetrahydrofuranyl, tetrahydroisoquinolinyl, tetrahydropyranyl, tetrahydrothienyl, tetrazolyl, thiadiazolopyrimidinyl, thiadiazolyl, thiamorpholinyl, thiazolidinyl, thiazolyl, thienyl, triazinyl, triazolyl, and 1,3,5-trithianyl. In certain embodiments, heterocyclic may also be optionally substituted with one or more substituents Z as described herein.

The term "halogen", "halide" or "halo" refers to fluorine, chlorine, bromine, and/or iodine.

The term "optionally substituted" is intended to mean that a group, including alkyl, alkenyl, alkynyl, cycloalkyl, aryl, aralkyl, heteroaryl, and heterocyclyl, may be substituted with one or more substituents Z, in one embodiment, one, two, three or four substituents Z, where each Z is independently selected from the group consisting of cyano, halo, oxo, nitro, $C_{1-6}$ alkyl, halo-$C_{1-6}$ alkyl, $C_{2-6}$ alkenyl, $C_{2-6}$ alkynyl, $C_{3-7}$ cycloalkyl, $C_{6-14}$ aryl, $C_{7-14}$ aralkyl, heteroaryl, heterocyclyl, —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^f$, —NR$^e$C(O)OR$^f$, —NR$^e$C(O)NR$^f$R$^g$—NR$^e$C(=NR$^h$)NR$^f$R$^g$—NR$^e$S(O)R$^f$, —NR$^e$S(O)$_2$R$^f$, —NR$^e$S(O)NR$^f$R$^g$, —NR$^e$S(O)$_2$NR$^f$R$^g$, —SR$^e$, —S(O)R$^e$, —S(O)$_2$R$^e$, and —S(O)$_2$NR$^f$R$^g$, wherein each R$^e$, R$^f$, R$^g$, and R$^h$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-14}$ aralkyl, heteroaryl, or heterocyclyl; or R$^f$ and R$^g$ together with the N atom to which they are attached form heterocyclyl.

The term "solvate" refers to a compound provided herein or a salt thereof, which further includes a stoichiometric or non-stoichiometric amount of solvent bound by non-covalent intermolecular forces. Where the solvent is water, the solvate is a hydrate.

In accordance with this disclosure, the term "comprising" is inclusive or open-ended and does not exclude additional, unrecited elements or method steps; the term "consisting of" excludes any element, step, or ingredient not specified; and the term "consisting essentially of" excludes any element, step, or ingredient that materially changes a basic characteristic of the invention.

In some embodiments, the formulation of the invention provided herein comprise at least one lipid, preferably a phospholipid, at least one surfactant, preferably a nonionic surfactant, optionally suspended in a pharmaceutically acceptable medium, preferably an aqueous solution, preferably having a pH ranging from 3.5 to 9.0, preferably from 4 to 7.5. The formulation of the invention may optionally contain buffers, antioxidants, preservatives, microbicides, antimicrobials, emollients, co-solvents, and/or thickeners. In some embodiments, the formulation of the invention comprises a mixture of more than one lipid, preferably more than one phospholipids. In some embodiments, the formulation of the invention consists essentially of at least one lipid, preferably a phospholipid, at least one surfactant, preferably a nonionic surfactant, a pharmaceutically acceptable carrier, and optionally buffers, antioxidants, preservatives, microbicides, antimicrobials, emollients, co-solvents, and/or thickeners. In some embodiments, the formulation of the invention consists of at least one lipid, preferably a phospholipid, at least one surfactant, preferably a nonionic surfactant, a pharmaceutically acceptable carrier, and one or more of the following: buffers, antioxidants, preservatives, microbicides, antimicrobials, emollients, co-solvents, and thickeners.

Lipid

In the sense of this disclosure, a "lipid" is any substance, which has properties like or similar to those of a fat. As a rule, it has an extended apolar group (the "chain", X) and generally also a water-soluble, polar hydrophilic part, the "head" group (Y) and has the basic Formula I:

$$X—Y_n \qquad (I)$$

wherein n is equal to or larger than zero.

Lipids with n=0 are referred to as apolar lipids and lipids with n≥1 are referred to as polar lipids. In this sense, all amphiphilic substances, including, but not limited to glycerides, glycerophospholipids, glycerophosphinolipids, glycerophosphonolipids, sulfolipids, sphingolipids, isoprenoid lipids, steroids or sterols and carbohydrate-containing lipids can generally be referred to as lipids, and are included as such in this disclosure. A list of relevant lipids and lipid related definitions is provided in EP 0 475 160 A1 (see, e.g. p. 4, l. 8 to p. 6, l. 3) and U.S. Pat. No. 6,165,500 (see, e.g., col. 6, l. 10 to col. 7, l. 58), each incorporated herein by reference in their entirety.

A phospholipid in various embodiments may contain (1) a moiety derived from glycerol or a sphingosine, (2) a phosphate group, and/or (3) simple organic molecule such as choline. A phospholipid as used herein may, for example, be a compound of Formula II:

$$R^1\text{—}CH_2\text{—}CHR^2\text{—}CR^3H\text{—}O\text{—}PHO_2\text{—}O\text{—}R^4 \quad (II)$$

wherein $R^1$ and $R^2$ are hydrogen, OH, an alkyl group, an aliphatic chain, an aliphatic chain derived from a fatty acid or a fatty alcohol; provided however that $R^1$ and $R^2$ cannot both be hydrogen, OH or a $C_1$-$C_3$ alkyl group; In some embodiments $R^1$ and $R^2$ are independently, an aliphatic chain, most often derived from a fatty acid or a fatty alcohol; $R^3$ generally is a hydrogen.

The OH-group of the phosphate is a hydroxyl radical or hydroxyl anion (i.e., hydroxide) form, dependent on degree of the group ionization. Furthermore, $R^4$ may be a proton or a short-chain alkyl group, substituted by a tri-short-chain alkylammonium group, such as a trimethylammonium group, or an amino-substituted short-chain alkyl group, such as 2-trimethylammonium ethyl group (cholinyl) or 2-dimethylammonium short alkyl group.

A sphingophospholipid is, for example, a compound of Formula IIB:

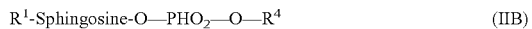

$$R^1\text{-Sphingosine-O}\text{—}PHO_2\text{—}O\text{—}R^4 \quad (IIB)$$

wherein $R^1$ is a fatty-acid attached via an amide bond to the nitrogen of the sphingosine and $R^4$ has the meanings given under Formula II.

A lipid preferably is a substance of formulae II or IIB, wherein $R^1$ and/or $R^2$ are acyl or alkyl, n-hydroxyacyl or n-hydroxyalkyl, but may also be branched, with one or more methyl groups attached at almost any point of the chain; usually, the methyl group is near the end of the chain (iso or anteiso). The radicals $R^1$ and $R^2$ may moreover either be saturated or unsaturated (mono-, di- or poly-unsaturated). $R^3$ is hydrogen and $R^4$ is 2-trimethylammonium ethyl (the latter corresponds to the phosphatidyl choline head group), 2-dimethylammonium ethyl, 2-methylammonium ethyl or 2-aminoethyl (corresponding to the phosphatidyl ethanolamine head group). $R^4$ may also be a proton (giving phosphatidic acid), a serine (giving phosphatidylserine), a glycerol (giving phosphatidylglycerol), an inositol (giving phosphatidylinositol), or an alkylamine group (giving phosphatidylethanolamine in case of an ethylamine), if one chooses to use a naturally occurring glycerophospholipid. Otherwise, any other sufficiently polar phosphate ester, such that will form a lipid bilayer, may be considered as well for making the formulations of the disclosure.

A phospholipid is, for example, a compound of Formula IIC:

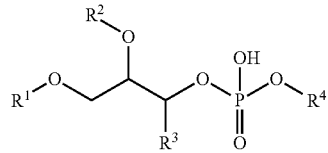

wherein $R^1$ and $R^2$ are independently an acyl group, alkyl group, n-hydroxyacyl group, or n-hydroxyalkyl group, most often derived from a fatty acid or a fatty alcohol, wherein $R^1$ and $R^2$ may also be branched, with one or more methyl groups attached at almost any point of the chain; usually, the methyl group is near the end of the chain (iso or anteiso), wherein $R^1$ and $R^2$ cannot both be hydrogen, OH or a $C_1$-$C_3$ alkyl group. The radicals $R^1$ and $R^2$ may moreover either be saturated or unsaturated (mono-, di- or poly-unsaturated). $R^3$ generally is a hydrogen. The OH-group of the phosphate is a hydroxyl radical or hydroxyl anion (i.e., hydroxide) form, dependent on degree of the group ionization. Furthermore, $R^4$ may be a proton or a short-chain alkyl group, substituted by a tri-short-chain alkylammonium group, such as a trimethylammonium group, or an amino-substituted short-chain alkyl group, such as 2-trimethylammonium ethyl group (cholinyl) or 2-dimethylammonium short alkyl group. $R^4$ may be 2-trimethylammonium ethyl (the latter corresponds to the phosphatidyl choline head group), 2-dimethylammonium ethyl, 2-methylammonium ethyl or 2-aminoethyl (corresponding to the phosphatidyl ethanolamine head group). $R^4$ may also be a proton (giving phosphatidic acid), a serine (giving phosphatidylserine), a glycerol (giving phosphatidylglycerol), an inositol (giving phosphatidylinositol), or an alkylamine group (giving phosphatidylethanolamine in case of an ethylamine), if one chooses to use a naturally occurring glycerophospholipid. Otherwise, any other sufficiently polar phosphate ester, such that will form a lipid bilayer, may be considered as well for making the formulations of the disclosure.

Table 1 lists preferred phospholipids in accordance with one embodiment of the disclosure.

TABLE 1

| | | Preferred (phospho)lipids | | |
|---|---|---|---|---|
| Fatty chain | | Phospholipid: Type and Charge | | |
| Name(s) | Length: nr. of double bonds | Phosphatidylcholine/ ±Main lipid, L1 | Phosphatidylethanolamine/ ±Main lipid, L1 | Sphingomyelin/ +Main lipid, L1 |
| | C24 | | | |
| Behen(o)yl | C22 | | | |
| Eruca(o)yl | C22:1-13cis | | | |
| Arachin(o)yl | C20 | | | |
| Gadolen(o)yl | C20:1-11cis | | | |
| Arachidon(o)yl | C20:4-5,8,11,14cis | | | |
| Ole(o)yl | C18:1-9cis | DOPC | DOPE | SM-oleyl |
| Stear(o)yl | C18 | | | |
| Linol(o)yl | C18:2-9,12cis | (Soy-PC/ | (Soy-PE/ | Brain SM |

TABLE 1-continued

| | | Preferred (phospho)lipids | | |
|---|---|---|---|---|
| Linole(n/o)yl | C18:3-9,12,15cis | Egg-PC) | Egg-PE) | |
| Palmitole(o)yl | C18:1-9cis | | | |
| Palmit(o)yl | C16 | | | |
| Myrist(o)yl | C14 | DMPC | DMPE | SM-myristyl |
| Laur(o)yl | C12 | DLPC | DLPE | SM-lauryl |
| Capr(o)yl | C10 | | | |
| Rel. concentration range L1/L2 (M/M) | | 1/0 | 1/0 | |
| "Total Lipid"* concentration range (w-%) | | 0.5-45 | 0.5-45 | |

| | Fatty chain | | | |
|---|---|---|---|---|
| | Length: | Phospholipid: Type and Charge | | |
| Name(s) | nr. of double bonds | Phosphatidylglycerol/ −Aux, lipid, L2 | Phosphatidylinositol/ −Aux, lipid, L2 | Phosphatidic acid/ −Aux, lipid, L2 |
| | C24 | | | |
| Behen(o)yl | C22 | | | |
| Eruca(o)yl | C22:1-13cis | | | |
| Arachin(o)yl | C20 | | | |
| Gadolen(o)yl | C20:1-11cis | | | |
| Arachidon(o)yl | C20:4-5,8,11,14cis | | | |
| Ole(o)yl | C18:1-9cis | DOPG | DOPI | DOPA |
| Stear(o)yl | C18 | | | |
| Linol(o)yl | C18:2-9,12cis | (Soy-PC/ | (Soy-PI/ | (Soy-PA/ |
| Linole(n/o)yl | C18:3-9,12,15cis | Egg-PC) | Liver-PI) | Egg-PA) |
| Palmitole(o)yl | C18:1-9cis | | | |
| Palmit(o)yl | C16 | | | |
| Myrist(o)yl | C14 | DMPG | DMPI | |
| Laur(o)yl | C12 | | | DLPA |
| Capr(o)yl | C10 | | | |
| Rel. concentration range L1/L2 (M/M) | | 10/1-1/1 | 10/1-3/1 | 10/1-5/1 |
| "Total Lipid"* concentration range (w-%) | | 0.5-40 | 0.5-40 | 0.5-40 |

*Total Lipid includes phospholipid(s), surfactant(s)t and all lipophilic excipients The preferred lipids in the context of this disclosure are uncharged and form stable, well hydrated bilayers; phosphatidylcholines, phosphatidylethanolamine, and sphingomyelins are the most prominent representatives of such lipids. Any of those can have chains as listed in the Table 1, the ones forming fluid phase bilayers, in which lipid chains are in disordered state, being preferred.

Different negatively charged, i.e., anionic, lipids can also be incorporated into vesicular lipid bilayers. Attractive examples of such charged lipids are phosphatidylglycerols, phosphatidylinositols and, somewhat less preferred, phosphatidic acid (and its alkyl ester) or phosphatidylserine. It will be realized by anyone skilled in the art that it is less commendable to make vesicles just from the charged lipids than to use them in a combination with electro-neutral bilayer component(s). In case of using charged lipids, buffer composition and/or pH care must selected so as to ensure the desired degree of lipid head-group ionization and/or the desired degree of electrostatic interaction between the, oppositely, charged drug and lipid molecules. Moreover, as with neutral lipids, the charged bilayer lipid components can in principle have any of the chains listed in the Table 1. The chains forming fluid phase lipid bilayers are clearly preferred, however, both due to vesicle adaptability increasing role of increasing fatty chain fluidity and due to better ability of lipids in fluid phase to mix with each other.

The fatty acid- or fatty alcohol-derived chain of a lipid is typically selected amongst the basic aliphatic chain types given in the following tables:

TABLE 2

The (most) preferred basic, straight, saturated fatty chain residues

| Shorthand designation | Systematic name | Trivial name |
|---|---|---|
| 12:0 | Dodecanoic | Lauric |
| 13:0 | Tridecanoic | |
| 14:0 | Tetradecanoic | Myristic |
| 15:0 | Pentadecanoic | |
| 16:0 | Hexadecanoic | Palmitic |
| 17:0 | Heptadecanoic | Margaric |
| 18:0 | Octadecanoic | Stearic |
| 19:0 | Nonadecanoic | |
| 20:0 | Eicosanoic | Arachidic |
| 21:0 | Heneicosanoic | |
| 22:0 | Docosanoic | Behenic |
| 23:0 | Tricosanoic | |
| 24:0 | Tetracosanoic | Lignoceric |

TABLE 3

The (most) preferred monoenoic fatty chain residues

| Shorthand designation | Systematic name | Trivial name |
|---|---|---|
| 9-14:1/14:1(n-5) | cis-9-Tetradecenoic | Myristoleic |
| 7-16:1/16:1(n-9) | cis-7-Hexadecenoic | |
| 9-16:1/16:1(n-7) | cis-9-Hexadecenoic | Palmitoleic |
| 9-18:1/18:1(n-9) | cis-9-Octadecenoic | Oleic |
| 11-18:1/18:1(n-7) | cis-11-Octadecenoic | cis-Vaccenic |
| 11-20:1/20:1(n-9) | cis-11-Eicosenoic | Gondoic |
| 14-20:1/20:1(n-6) | cis-14-Eicosaenoic | |
| 13-22:1/22:1(n-9) | cis-13-Docosenoic | Erucic |

TABLE 3-continued

The (most) preferred monoenoic fatty chain residues

| Shorthand designation | Systematic name | Trivial name |
|---|---|---|
| 15-24:1/24:1(n-9) | cis-15-Tetracosenoic | Nervoni |
| 3t-18:1 | trans-3-Hexadecenoi | |
| 9t-18:1 | trans-9-Octadecenoic | Elaidic |
| 11t-18:1 | trans-11-Octadecenoic | Vaccenic |

TABLE 4

The (most) preferred dienoic and polyenoic fatty chain residues

| Shorthand designation | Systematic name | Trivial name |
|---|---|---|
| 10,13c-16:2/16:2(n-3) | 10-cis,13-cis-Hexadecadienoic | |
| 7,10c-16:2/16:3(n-6) | 7-cis,10-cis-Hexadecadienoic | |
| 7,10,13c-16:3/16:3(n-3) | 7-cis,10-cis,13-cis-Hexadecatrienoic | |
| 12,15c-18:2/18:2(n-3) | 12-cis,15-cis-Octadecadienoic | α-Linoleic |
| 10,12t-18:2/18:2(n-6) | trans-10,trans-12-Octadecadienoic | |
| 9,12c-18:2/18:2(n-6) | 9-cis,12-cis-Octadecadienoic | γ-Linoleic |
| 9,12,15c-18:3/18:3(n-3) | 9-cis,12-cis,15-cis-Octadecatrienoic | α-Linolenic |
| 6,9,12c-18:3/18:3(n-6) | 6-cis,9-cis,12-cis-Octadecatrienoic | γ-Linolenic |
| 9c,11c,13t-18:3 | 9-cis,11-trans,13-trans-Octadecatrienoic | α-Eleostearic |
| 8t,10t,12c-18:3 | 8-trans,10-trans,12-cis-Octadecatrienoic | Calendic |
| 6,9,12,15c-18:4/18:4(n-3) | 6,9,12,15-Octadecatetraenoic | Stearidonic |
| 3,6,9,12c-18:4/18:4(n-6) | 3,6,9,12-Octadecatetraenoic | |
| 3,6,9,12,15c-18:5/18:5(n-3) | 3,6,9,12,15-Octadecapentaenoic | |
| 14,17c-20:2/20:2(n-3) | 14-cis,17-cis-Eicosadienoic | |
| 11,14c-20:2/20:2(n-6) | 11-cis,14-cis-Eicosadienoic | |
| 11,14,17c-20:3/20:3(n-3) | 8-cis,11-cis,14-cis-Eicosatrienoic | Dihomo-α-linolenic |
| 8,11,14c-20:3/20:3(n-6) | 8-cis,11-cis,14-cis-Eicosatrienoic | Dihomo-γ-linolenic |
| 5,8,11c-20:3 20:3(n-9) | 5,8,11all-cis-Eicosatrienoic | 'Mead's' |
| 5,8,11,14c-20:4/20:4(n-6) | 5,8,11;14-all-cis-Eicosatetraenoic | Arachidonic |
| 8,11,14,17c-20:4/20:4(n-3) | 8,11,14,17-all-cis-Eicosatetraenoic | |
| 5,8,11,14,17c-20:5 or 20:5(n-3) | 5,8,11,14,17-all-cis-Eicosapentaenoic | |
| 13,16c-22:2 | 13,16-Docosadienoic | |
| 13,16,19c-22:3/22:3(n-3) | 13,16,19-Docosatrienoic | |
| 10,13,16c-22:3/22:3(n-6) | 10,13,16-Docosatrienoic | |
| 7,10,13,16c-22:4/22:4(n-6) | 7,10,13,16-Docosatetraenoic | Adrenic |
| 4,7,10,13,16c-22:5 or 22:5(n-6) | 4,7,10,13,16-Docosapentaenoic | |
| 4,7,10,13,16,19c-22:5 or 22:6(n-3) | 4,7,10,13,16,19-Docosahexaenoic | |

Other double bond combinations or positions are possible as well.

Suitable fatty residues can furthermore be branched, for example, can contain a methyl group in an iso or anteiso position of the fatty acid chain, or else closer to the chain middle, as in 10-R-methyloctadecanoic acid or tuberculostearic chain. Relatively important amongst branched fatty acids are also isoprenoids, many of which are derived from 3,7,11,15-tetramethylhexadec-trans-2-en-1-ol, the aliphatic alcohol moiety of chlorophyll. Examples include 5,9,13,17-tetramethyloctadecanoic acid and especially 3,7,11,15-tetramethylhexadecanoic (phytanic) and 2,6,10,14-tetramethylpentadecanoic (pristanic) acids. A good source of 4,8,12-trimethyltridecanoic acid are marine organisms. Combination of double bonds and side chains on a fatty residue are also possible.

Alternatively, suitable fatty residues may carry one or a few oxy- or cyclic groups, especially in the middle or towards the end of a chain. The most prominent amongst the later, alicyclic fatty acids, are those comprising a cyclopropane (and sometimes cyclopropene) ring, but cyclohexyl and cycloheptyl rings can also be found and might be useful for purposes of this disclosure. 2-(D)-Hydroxy fatty acids are more ubiquitous than alicyclic fatty acids, and are also important constituents of sphingolipids. Also interesting are 15-hydroxy-hexadecanoic and 17-hydroxy-octadecanoic acids, and maybe 9-hydroxy-octadeca-trans-10,trans-12-dienoic (dimorphecolic) and β-hydroxy-octadeca-cis-9,trans-11-dienoic (coriolic) acid. Arguably the most prominent hydroxyl-fatty acid in current pharmaceutical use is ricinoleic acid, (D-(–)12-hydroxy-octadec-cis-9-enoic acid, which comprises up to 90% of castor oil, which is also often used in hydrogenated form. Epoxy-, methoxy-, and furanoid-fatty acids are of only limited practical interest in the context of this disclosure.

Generally speaking, unsaturation, branching or any other kind of derivatization of a fatty acid is best compatible with the intention of present disclosure of the site of such modification is in the middle or terminal part of a fatty acid chain. The cis-unsaturated fatty acids are also more preferable than trans-unsaturated fatty acids and the fatty radicals with fewer double bonds are preferred over those with multiple double bonds, due to oxidation sensitivity of the latter. Moreover, symmetric chain lipids are generally better suited than asymmetric chain lipids.

A preferred lipid of the Formula II is, for example, a natural phosphatidylcholine, which used to be called lecithin. It can be obtained from egg (rich in palmitic, $C_{16:0}$, and oleic, $C_{18:1}$, but also comprising stearic, $C_{18:0}$, palmitoleic, $C_{16:1}$, linolenic, $C_{18:2}$, and arachidonic, $C_{20:4}$, radicals), soybean (rich in unsaturated $C_{18}$ chains, but also containing some palmitic radical, amongst a few others), coconut (rich in saturated chains), olives (rich in monounsaturated chains), saffron (safflower) and sunflowers (rich in n-6 linoleic acid), linseed (rich in n-3 linolenic acid), from whale fat (rich in monounsaturated n-3 chains), from primrose or primula (rich in n-3 chains). Preferred, natural phosphatidyl ethanolamines (used to be called cephalins) frequently originate from egg or soybeans. Preferred sphingomyelins of biological origin are typically prepared from eggs or brain tissue.

Preferred phosphatidylserines also typically originate from brain material whereas phosphatidylglycerol is preferentially extracted from bacteria, such as *E. Coli*, or else prepared by way of transphosphatidylation, using phospholipase D, starting with a natural phosphatidylcholine. The preferably used phosphatidylinositols are isolated from commercial soybean phospholipids or bovine liver extracts. The preferred phosphatidic acid is either extracted from any of the mentioned sources or prepared using phospholipase D from a suitable phosphatidylcholine.

Furthermore, synthetic phosphatidyl cholines ($R^4$ in Formula II corresponds to 2-trimethylammonium ethyl), and $R^1$ and $R^2$ are aliphatic chains, as defined in the preceding paragraph with 12 to 30 carbon atoms, preferentially with 14 to 22 carbon atoms, and even more preferred with 16 to 20 carbon atoms, under the proviso that the chains must be chosen so as to ensure that the resulting ESAs comprise fluid lipid bilayers. This typically means use of relatively short saturated and of relatively longer unsaturated chains. Synthetic sphingomyelins ($R^4$ in Formula IIB corresponds to 2-trimethylammonium ethyl), and $R^1$ is an aliphatic chain, as defined in the preceding paragraph, with 10 to 20 carbon atoms, preferentially with 10 to 14 carbon atoms per fully saturated chain and with 16-20 carbon atoms per unsaturated chain.

Synthetic phosphatidyl ethanolamines ($R^4$ is 2-aminoethyl), synthetic phosphatidic acids ($R^4$ is a proton) or its ester ($R^4$ corresponds, for example, to a short-chain alkyl, such as methyl or ethyl), synthetic phosphatidyl serines ($R^4$ is L- or D-serine), or synthetic phosphatidyl (poly)alcohols, such as phosphatidyl inositol, phosphatidyl glycerol ($R^4$ is L- or D-glycerol) are preferred as lipids, wherein $R^1$ and $R^2$ are fatty residues of identical or moderately different type and length, especially such as given in the corresponding tables given before in the text. Moreover, $R^1$ can represent alkenyl and $R^2$ identical hydroxyalkyl groups, such as tetradecylhydroxy or hexadecylhydroxy, for example, in ditetradecyl or dihexadecylphosphatidyl choline or ethanolamine, $R^1$ can represent alkenyl and $R^2$ hydroxyacyl, such as a plasmalogen ($R^4$ trimethylammonium ethyl), or $R^1$ can be acyl, such as lauryl, myristoyl or palmitoyl and $R^2$ can represent hydroxy as, for example, in natural or synthetic lysophosphatidyl cholines or lysophosphatidyl glycerols or lysophosphatidyl ethanolamines, such as 1-myristoyl or 1-palmitoyllysophosphatidyl choline or -phosphatidyl ethanolamine; frequently, $R^3$ represents hydrogen.

A lipid of Formula IIB is also a suitable lipid within the sense of this disclosure. In Formula IIB, n=1, $R^1$ is an alkenyl group, $R^2$ is an acylamido group, $R^3$ is hydrogen and $R^4$ represents 2-trimethylammonium ethyl (choline group). Such a lipid is known under the name of sphingomyelin.

Suitable lipids furthermore are a lysophosphatidyl choline analog, such as 1-lauroyl-1,3-dihydroxypropane-3-phosphoryl choline, a monoglyceride, such as monoolein or monomyristin, a cerebroside, ceramide polyhexoside, sulfatide, sphingoplasmalogen, a ganglioside or a glyceride, which does not contain a free or esterified phosphoryl or phosphono or phosphino group in the 3 position. An example of such a glyceride is diacylglyceride or 1-alkenyl-1-hydroxy-2-acyl glyceride with any acyl or alkenyl groups, wherein the 3-hydroxy group is etherified by one of the carbohydrate groups named, for example, by a galactosyl group such as a monogalactosyl glycerin.

Lipids with desirable head or chain group properties can also be formed by biochemical means, for example, by means of phospholipases (such as phospholilpase A1, A2, B, C and, in particular, D), desaturases, elongases, acyl transferases, etc., from natural or synthetic precursors.

Furthermore, a suitable lipid is any lipid, which is contained in biological membranes and can be extracted with the help of apolar organic solvents, such as chloroform. Aside from the lipids already mentioned, such lipids also include, for example, steroids, such as estradiol, or sterols, such as cholesterol, beta-sitosterol, desmosterol, 7-keto-cholesterol or beta-cholestanol, fat-soluble vitamins, such as retinoids, vitamins, such as vitamin A1 or A2, vitamin E, vitamin K, such as vitamin K1 or K2 or vitamin D1 or D3, etc.

The less soluble amphiphilic components comprise or preferably comprise a synthetic lipid, such as myristoleoyl, palmitoleoyl, petroselinyl, petroselaidyl, oleoyl, elaidyl, cis- or trans-vaccenoyl, linolyl, linolenyl, linolaidyl, octadecatetraenoyl, gondoyl, eicosaenoyl, eicosadienoyl, eicosatrienoyl, arachidoyl, cis- or trans-docosaenoyl, docosadienoyl, docosatrienoyl, docosatetraenoyl, lauroyl, tridecanoyl, myristoyl, pentadecanoyl, palmitoyl, heptadecanoyl, stearoyl or nonadecanoyl, glycerophospholipid or corresponding derivatives with branched chains or a corresponding dialkyl or sphingosin derivative, glycolipid or other diacyl or dialkyl lipid.

The more soluble amphiphilic components(s) is/are frequently derived from the less soluble components listed above and, to increase the solubility, substituted and/or complexed and/or associated with a butanoyl, pentanoyl, hexanoyl, heptanoyl, octanoyl, nonanoyl, decanoyl or undecanoyl substituent or several, mutually independent, selected substituents or with a different material for improving the solubility.

A further suitable lipid is a diacyl- or dialkyl-glycerophosphoetha-nolamine azo polyethoxylene derivative, a didecanoylphosphatidyl choline or a diacylphosphoolligomaltobionamide.

In certain embodiments, the amount of lipid in the formulation is from about 1% to about 12%, about 1% to about 10%, about 1% to about 4%, about 4% to about 7% or about 7% to about 10% by weight. In a specific embodiment, the lipid is a phospholipid. In another specific embodiment, the phospholipid is a phosphatidylcholine.

In some embodiments, the lipid in the formulation does not comprise an alkyl-lysophospholipid. In some embodiments, the lipid in the formulation does not comprise a polyeneylphosphatidylcholine.

Surfactant

The term "surfactant" has its usual meaning. A list of relevant surfactants and surfactant related definitions is provided in EP 0 475 160 A1 (see, e.g., p. 6, l. 5 to p. 14. l. 17) and U.S. Pat. No. 6,165,500 (see, e.g., col. 7, l. 60 to col. 19, l. 64), each herein incorporated by reference in their entirety, and in appropriate surfactant or pharmaceutical Handbooks, such as Handbook of Industrial Surfactants or US Pharmacopoeia, Pharm. Eu. In some embodiments, the surfactants are those described in Tables 1-18 of U.S. Patent Application Publication No. 2002/0012680 A1, published Jan. 31, 2002, the disclosure of which is herein incorporated by reference in its entirety. The following list therefore only offers a selection, which is by no means complete or exclusive, of several surfactant classes that are particularly common or useful in conjunction with present patent application. Preferred surfactants to be used in accordance with the disclosure include those with an HLB greater than 12. The list includes ionized long-chain fatty acids or long chain fatty alcohols, long chain fatty ammonium salts, such as alkyl- or alkenoyl-trimethyl-, -dimethyl- and -methylammonium salts, alkyl- or alkenoyl-sulphate salts, long fatty chain dimethyl-aminoxides, such as alkyl- or alkenoyl-dimethyl-aminoxides, long fatty chain, for example alkanoyl, dimethyl-aminoxides and especially dodecyl dimethyl-aminoxide, long fatty chain, for example alkyl-N-methylglucamide-s and alkanoyl-N-methylglucamides, such as MEGA-8, MEGA-9 and MEGA-10, N-long fatty chain-N,N-dimethylglycines, for example N-alkyl-N,N-dimethylglycines, 3-(long fatty chain-dimethylammonio)-alkanesulphonates, for example 3-(acyidimethylammonio)-alkanesulphonates, long fatty chain derivatives of sulphosuccinate salts, such as bis(2-ethylalkyl) sulphosuccinate salts, long fatty chain-sulphobetaines, for example acyl-sulphobetaines, long fatty chain betaines, such as EMPIGEN BB or ZWITTERGENT-3-16, -3-14, -3-12, -3-10, or -3-8, or polyethylen-glycol-acylphenyl ethers, especially nonaethylen-glycol-octyl-phenyl ether, polyethylene-long fatty chain-ethers, especially polyethylene-acyl ethers, such as nonaethylen-decyl ether, nonaethylen-dodecyl ether or octaethylene-dodecyl ether, polyethyleneglycol-isoacyl ethers, such as octaethyleneglycol-isotridecyl ether, polyethyleneglycol-sorbitane-long fatty chain esters, for example polyethyleneglycol-sorbitane-acyl esters and especially polyoxyethylene-monolaurate (e.g. polysorbate 20 or Tween 20), polyoxyethylene-sorbitan-monooleate (e.g. polysorbate 80 or Tween 80), polyoxyethylene-sorbitan-monolauroleylate, polyoxyethylene-sorbitan-monopetroselinate, polyoxyethylene-sorbitan-monoelaidate, polyoxyethylene-sorbitan-myristoleylate, polyoxyethylene-sorbitan-palmitoleinylate, polyoxyethylene-sorbitan-p-etroselinylate, polyhydroxyethylene-long fatty chain ethers, for example polyhydroxyethylene-acyl ethers, such as polyhydroxyethylene-lauryl ethers, polyhydroxyethylene-myristoyl ethers, polyhydroxyethylene-cetylst-earyl, polyhydroxyethylene-palmityl ethers, polyhydroxyethylene-oleoyl ethers, polyhydroxyethylene-palmitoleoyl ethers, polyhydroxyethylene-lino-leyl, polyhydroxyethylen-4, or 6, or 8, or 10, or 12-lauryl, miristoyl, palmitoyl, palmitoleyl, oleoyl or linoeyl ethers (Brij series), or in the corresponding esters, polyhydroxyethylen-laurate, -myristate, -palmitate, -stearate or -oleate, especially polyhydroxyethylen-8-stearate (Myrj 45) and polyhydroxyethylen-8-oleate, polyethoxylated castor oil 40 (Cremophor EL), sorbitane-mono long fatty chain, for example alkylate (Arlacel or Span series), especially as sorbitane-monolaurate (Arlacel 20, Span 20), long fatty chain, for example acyl-N-methylglucamides, alkanoyl-N-methylglucamides, especially decanoyl-N-methylglucamide, dodecanoyl-N-methylglucamide, long fatty chain sulphates, for example alkyl-sulphates, alkyl sulphate salts, such as lauryl-sulphate (SDS), oleoyl-sulphate; long fatty chain thioglucosides, such as alkylthioglucosides and especially heptyl-, octyl- and nonyl-beta-D-thioglucopyranoside; long fatty chain derivatives of various carbohydrates, such as pentoses, hexoses and disaccharides, especially alkylglucosides and maltosides, such as hexyl-, heptyl-, octyl-, nonyl- and decyl-beta-D-glucopyranoside or D-maltopyranoside; further a salt, especially a sodium salt, of cholate, deoxycholate, glycocholate, glycodeoxycholate, taurodeoxycholate, taurocholate, a fatty acid salt, especially oleate, elaidate, linoleate, laurate, or myristate, most often in sodium form, lysophospholipids, n-octadecylene-glycero-phosphatidic acid, octadecylene-phosphorylglycerol, octadecylene-phosphorylserine, n-long fatty chain-glycero-phosphatidic acids, such as n-acyl-glycero-phosphatidic acids, especially lauryl glycero-phosphatidic acids, oleoyl-glycero-phosphatidic acid, n-long fatty chain-phosphorylglycerol, such as n-acyl-phosphorylglycerol, especially lauryl-, myristoyl-, oleoyl- or palmitoeloyl-phosphorylglycerol, n-long fatty chain-phosphorylserine, such as n-acyl-phosphorylserine, especially lauryl-, myristoyl-, oleoyl- or palmitoeloyl-phosphorylserine, n-tetradecyl-glycero-phosphatidic acid, n-tetradecyl-phosphorylglycerol, n-tetradecyl-phosphorylserine, corresponding-, elaidoyl-, vaccenyl-lysophospholipids, corresponding short-chain phospholipids, as well as all surface active and thus membrane destabilising polypeptides. Surfactant chains are typically chosen to be in a fluid state or at least to be compatible with the maintenance of fluid-chain state in carrier aggregates.

Table 5 lists preferred surfactants in accordance with one embodiment of the disclosure.

TABLE 5

| Preferred surfactants | | Nonionic surfactants (S) | | | | |
| Fatty chain | | Head/Type/TM | | | | |
| Name(s) | Length: nr. of double bonds | POE-sorbitan-ester Tween | POE-ether Brij, Macrogol | POE-ester Myrj, Nonex | POE-phenoxy-ether Triton | Selected brandnames |
| --- | --- | --- | --- | --- | --- | --- |
| | C24 | | | | | |
| Behen(o)yl | C22 | | | | | |
| Eruca(o)yl | C22:1-13cis | | | | | |
| Arachin(o)yl | C20 | | | | | |
| Gadolen(o)yl | C20:1-11cis | | | | | |
| Arachidon(o)yl | C20:4-5,8,11,14cis | | | | | |
| Ole(o)yl | C18:1-9cis | Tween 80 | Brij 98 | Simulsol-2599 | TritonX100** | |
| Stear(o)yl | C18 | Tween 60 | | Myrj-52 | | |
| Linol(o)yl | C18:2-9,12cis | | | | | |
| Linole(n/o)yl | C18:3-9,12,15cis | | | | | |
| Palmitole(o)yl | C18:1-9cis | | | | | |
| Palmit(o)yl | C16 | Tween 40 | | NN | | |
| Myrist(o)yl | C14 | | | | | |

TABLE 5-continued

| | Preferred surfactants Fatty chain | Nonionic surfactants (S) Head/Type/TM | | | | |
|---|---|---|---|---|---|---|
| Name(s) | Length: nr. of double bonds | POE-sorbitan-ester Tween | POE-ether Brij, Macrogol | POE-ester Myrj, Nonex | POE-phenoxy-ether Triton | Selected brandnames |
| Laur(o)yl | C12 | Tween 20 | Brij 35 | NN | | |
| Capr(o)yl | C10 | | | | | |
| Rel. concentration range L/S (M/M) | | 5/1-1/1 | 5/1-1/1 | 5/1-1/1 | 4/1-3/2 | |

NN: not readily available in the market but in principle suitable
**Triton is not an oleate, but an octylphenoxy-POE derivative
Myrj-45: Stearoyl-EO8;
Myrj-49: Stearoyl-EO20 (not in the market);
Myrj-59: Stearoyl-EO100;
Myrj-52: Stearoyl-EO40;
Simulsol-2599 = Macrogol-10-oleate
Brij-98: Oleoyl-EO20
Brij-35: Lauryl-EO23

In certain embodiments, the surfactant is a nonionic surfactant. The surfactant may be present in the formulation in about 1% to about 10%, about 1% to about 4%, about 4% to about 7% or about 7% to about 10% by weight. In some embodiments, the amount of surfactants in the formulation is from about 0.2% to about 0.5%. In certain embodiments, the nonionic surfactant is selected from the group consisting of: polyoxyethylene sorbitans (polysorbate surfactants), polyhydroxyethylene stearates or polyhydroxyethylene laurylethers (Brij surfactants). In a specific embodiment, the surfactant is a polyoxyethylene-sorbitan-monooleate (e.g. polysorbate 80 or Tween 80). In certain embodiments, the polysorbate can have any chain with 12 to 20 carbon atoms. In certain embodiments, the polysorbate is fluid in the formulation, which may contain one or more double bonds, branching, or cyclo-groups.

Formulations

In some embodiments, the formulations of the invention comprise only one lipid and only one surfactant. In other embodiments, the formulations of the invention comprise more than one lipid and only one surfactant, e.g., two, three, four, or more lipids and one surfactant. In other embodiments, the formulations of the invention comprise only one lipid and more than one surfactant, e.g., two, three, four, or more surfactants and one lipid. In other embodiments, the formulations of the invention comprise more than one lipid and more than one surfactant, e.g., two, three, four, or more lipids and two, three, four, or more surfactants.

The formulations of the invention may have a range of lipid to surfactant ratios. The ratios may be expressed in terms of molar terms (mol lipid/mol surfactant). The molar ratio of lipid to surfactant in the formulations may be from about 1:3 to about 30:1, from about 1:2 to about 30:1, from about 1:1 to about 30:1, from about 5:1 to about 30:1, from about 10:1 to about 30:1, from about 15:1 to about 30:1, or from about 20:1 to about 30:1. In certain embodiments, the molar ratio of lipid to surfactant in the formulations of the invention may be from about 1:2 to about 10:1. In certain embodiments, the ratio is from about 1:1 to about 2:1, from about 2:1 to about 3:1, from about 3:1 to about 4:1, from about 4:1 to about 5:1 or from about 5:1 to about 10:1. In certain embodiments, the molar ratio is from about 10.1 to about 30:1, from about 10:1 to about 20:1, from about 10:1 to about 25:1, and from about 20:1 to about 25:1. In specific embodiments, the lipid to surfactant ratio is about 1.0:1.0, about 1.25:1.0, about 1.5/1.0, about 1.75/1.0, about 2.0/1.0, about 2.5/1.0, about 3.0/1.0 or about 4.0/1.0.

The formulations of the invention may also have varying amounts of total amount of the following components: lipid and surfactant combined (TA). The TA amount may be stated in terms of weight percent of the total composition. In one embodiment, the TA is from about 1% to about 40%, about 5% to about 30%, about 7.5% to about 15%, about 5% to about 10%, about 10% to about 20% or about 20% to about 30%. In specific embodiments, the TA is 8%, 9%, 10%, 15% or 20%.

Selected ranges for total lipid amounts and lipid/surfactant ratios (mol/mol) for the formulations of the invention are described in Table 6 below:

TABLE 6

| Total Amount and Lipid to Surfactant Ratios | |
|---|---|
| TA (and surfactant) (%) | Lipid/Surfactant (mol/mol) |
| 5 to 10 | 1.0 to 1.25 |
| 5 to 10 | 1.25 to 1.75 |
| 5 to 10 | 1.75 to 2.25 |
| 5 to 10 | 2.25 to 3.00 |
| 5 to 10 | 3.00 to 4.00 |
| 5 to 10 | 4.00 to 8.00 |
| 5 to 10 | 10.00 to 13.00 |
| 5 to 10 | 15.00 to 20.00 |
| 5 to 10 | 20.00 to 22.00 |
| 5 to 10 | 22.00 to 25.00 |
| 10 to 20 | 1.0 to 1.25 |
| 10 to 20 | 1.25 to 1.75 |
| 10 to 20 | 1.25 to 1.75 |
| 10 to 20 | 2.25 to 3.00 |
| 10 to 20 | 3.00 to 4.00 |
| 10 to 20 | 4.00 to 8.00 |
| 10 to 20 | 10.00 to 13.00 |
| 10 to 20 | 15.00 to 20.00 |
| 10 to 20 | 20.00 to 22.00 |
| 10 to 20 | 22.00 to 25.00 |

The formulations of the invention do not comprise a pharmaceutically active agent that has received marketing or regulatory approval in any country for the treatment of disorders related to fatty acid deficiencies, fatty acid metabolism, hypertriglyceridemia and hypercholesterolemia, or any other disorder listed above.

The formulations of the invention may optionally contain one or more of the following ingredients: co-solvents, chelators, buffers, antioxidants, preservatives, microbicides, emollients, humectants, lubricants and thickeners. Preferred amounts of optional components are described in Table 7.

The formulations of the invention may include a buffer to adjust the pH of the aqueous solution to a range from pH 3.5 to pH 9, pH 4 to pH 7.5, or pH 4 to pH 6.5. Examples of buffers include, but are not limited to, acetate buffers, lactate buffers, phosphate buffers, and propionate buffers.

The formulations of the invention are typically formulated in aqueous media. The formulations may be formulated with or without co-solvents, such as lower alcohols A "microbicide" or "antimicrobial" agent is commonly added to reduce the bacterial count in pharmaceutical formulations. Some examples of microbicides are short chain alcohols, including ethyl and isopropyl alcohol, chlorbutanol, benzyl alcohol, chlorbenzyl alcohol, dichlorbenzylalcohol, hexachlorophene; phenolic compounds, such as cresol, 4-chloro-m-cresol, p-chloro-m-xylenol, dichlorophene, hexachlorophene, povidon-iodine; parabenes, especially alkyl-parabenes, such as methyl-, ethyl-, propyl-, or butyl-paraben, benzyl paraben; acids, such as sorbic acid, benzoic acid and their salts; quaternary ammonium compounds, such as alkonium salts, e.g., a bromide, benzalkonium salts, such as a chloride or a bromide, cetrimonium salts, e.g., a bromide, phenoalkecinium salts, such as phenododecinium bromide, cetylpyridinium chloride and other salts; furthermore, mercurial compounds, such as phenylmercuric acetate, borate, or nitrate, thiomersal, chlorhexidine or its gluconate, or any antibiotically active compounds of biological origin, or any suitable mixture thereof.

Examples of "antioxidants" are butylated hydroxyanisol (BHA), butylated hydroxytoluene (BHT) and di-tert-butyl-phenol (LY178002, LY256548, HWA-131, BF-389, CI-986, PD-127443, E-5119, BI-L-239XX, etc.), tertiary butylhydroquinone (TBHQ), propyl gallate (PG), 1-O-hexyl-2,3,5-trimethylhydroquinone (HTHQ); aromatic amines (diphenylamine, p-alkylthio-o-anisidine, ethylenediamine derivatives, carbazol, tetrahydroindenoindol); phenols and phenolic acids (guaiacol, hydroquinone, vanillin, gallic acids and their esters, protocatechuic acid, quinic acid, syringic acid, ellagic acid, salicylic acid, nordihydroguaiaretic acid (NDGA), eugenol); tocopherols (including tocopherols (alpha, beta, gamma, delta) and their derivatives, such as tocopheryl-acylate (e.g., -acetate, -laurate, myristate, -palmitate, -oleate, -linoleate, etc., or an y other suitable tocopheryl-lipoate), tocopheryl-POE-succinate; trolox and corresponding amide and thiocarboxamide analogues; ascorbic acid and its salts, isoascorbate, (2 or 3 or 6)-o-alkylascorbic acids, ascorbyl esters (e.g., 6-o-lauroyl, myristoyl, palmitoyl-, oleoyl, or linoleoyl-L-ascorbic acid, etc.). Also useful are the preferentially oxidised compounds, such as sodium bisulphite, sodium metabisulphite, thiourea; chellating agents, such as EDTA, GDTA, desferral; miscellaneous endogenous defence systems, such as transferrin, lactoferrin, ferritin, cearuloplasmin, haptoglobion, heamopexin, albumin, glucose, ubiquinol-10); enzymatic antioxidants, such as superoxide dismutase and metal complexes with a similar activity, including catalase, glutathione peroxidase, and less complex molecules, such as beta-carotene, bilirubin, uric acid; flavonoids (flavones, flavonols, flavonones, flavanonals, chacones, anthocyanins), N-acetyl-cystein, mesna, glutathione, thiohistidine derivatives, triazoles; tannines, cinnamic acid, hydroxycinnamatic acids and their esters (coumaric acids and esters, caffeic acid and their esters, ferulic acid, (iso-) chlorogenic acid, sinapic acid); spice extracts (e.g., from clove, cinnamon, sage, rosemary, mace, oregano, allspice, nutmeg); carnosic acid, carnosol, carsolic acid; rosmarinic acid, rosmaridiphenol, gentisic acid, ferulic acid; oat flour extracts, such as avenanthramide 1 and 2; thioethers, dithioethers, sulphoxides, tetralkylthiuram disulphides; phytic acid, steroid derivatives (e.g., U74006F); tryptophan metabolites (e.g., 3-hydroxykynurenine, 3-hydroxyanthranilic acid), and organochalcogenides.

"Thickeners" are used to increase the viscosity of pharmaceutical formulations to and may be selected from selected from pharmaceutically acceptable hydrophilic polymers, such as partially etherified cellulose derivatives, comprising carboxymethyl-, hydroxyethyl-, hydroxypropyl-, hydroxypropylmethyl- or methylcellulose; completely synthetic hydrophilic polymers comprising polyacrylates, polymethacrylates, poly(hydroxyethyl)-, poly(hydroxypropyl)-, poly(hydroxypropylmethyl)methacrylate, polyacrylonitrile, methallyl-sulphonate, polyethylenes, polyoxiethylenes, polyethylene glycols, polyethylene glycol-lactide, polyethylene glycol-diacrylate, polyvinylpyrrolidone, polyvinyl alcohols, poly(propylmethacrylamide), poly(propylene fumarate-co-ethylene glycol), poloxamers, polyaspartamide, (hydrazine cross-linked) hyaluronic acid, silicone; natural gums comprising alginates, carrageenan, guar-gum, gelatine, tragacanth, (amidated) pectin, xanthan, chitosan collagen, agarose; mixtures and further derivatives or co-polymers thereof and/or other pharmaceutically, or at least biologically, acceptable polymers.

The formulations of the present invention may also comprise a polar liquid medium. The formulations of the invention may be administered in an aqueous medium. The of the present invention may be in the form of a solution, suspension, emulsion, cream, lotion, ointment, gel, spray, film forming solution or lacquer.

In some embodiments, the invention relates to the use of a vesicular formulation as described above for the preparation of a pharmaceutical composition for the treatment of disorders related to fatty acid deficiencies, fatty acid metabolism, hypertriglyceridemia and hypercholesterolemia. In some embodiments, the invention relates to a vesicular formulation or pharmaceutical composition comprising at least one phospholipid and one nonionic surfactant for the treatment of disorders related to fatty acid deficiencies, fatty acid metabolism, hypertriglyceridemia and hypercholesterolemia wherein the formulation or pharmaceutical composition is formulated for subcutaneous, topical or intravenous delivery.

Table 7 lists preferred excipients for the formulation.

TABLE 7

Preferred excipients for use in the formulations of the invention

Designated activity

| Antioxidant | Molar (M) or Rel. w %* | Antibiotic | Molar (M) or Weight-% | Buffer | Molar |
|---|---|---|---|---|---|
| Primary | | | | | |
| Butylated hydroxyanisole, BHA | 0.1-8 | Acetate | 30-150 mM | Acetate | 30-150 mM |
| Butylated hydroxytoluene, BHT | 0.1-4 | Benzyl alcohol | 0.1-3 | Phosphate | 10-50 mM |
| Thymol | 0.1-1 | Butylparabene | 0.1-3 | Triethanolamine•HCL | 30-150 mM |
| Metabisulphite (MW = 190.1) | 1-5 mM | Ethylparabene | 0.1-3 | | |
| Bisulphite | 1-5 mM | Imidurea (MW = 388.30) | 0.1-1 | | |
| Thiourea (MW = 76.12) | 1-10 mM | Dimethoxane (MW = 174.2) | 0.03-0.1 | | |
| Monothioglycerol (MW = 108.16) | 1-20 mM | | | | |

TABLE 7-continued

Preferred excipients for use in the formulations of the invention

| | Designated activity | | | | |
|---|---|---|---|---|---|
| Antioxidant | Molar (M) or Rel. w %* | Antibiotic | Molar (M) or Weight-% | Buffer | Molar |
| Propyl gallate (MW = 212.2) | 0.02-0.2 | Methylparabene | 0.1-5 | | |
| Ascorbate (MW = 175.3 + ion) | 1-10 mM | Phenoxyethanol | 0.1-5 | | |
| Palmityl-ascorbate | 0.01-1 | Benzalkonium chloride | 0.01-0.2 | | |
| Tocopherol-PEG | 0.5-5 | Benzethonium chloride | 0.01-0.1 | | |
| Secondary (chelator) | | Phenol | 0.05-2 | | |
| EDTA (MW = 292) | 1-10 mM | Phenylethyl alcohol | 0.1-1 | | |
| EGTA (MW = 380.35) | 1-10 mM | Thimerosal | 0.005-0.1 | | |
| Desferal (MW = 656.79) | 0.1-5 mM | | | | |

*As percentage of Total Lipid quantity
EGTA = Ethylene glycol-bis-(2-aminoethyl)-N,N,N',N'-tetraacetic acid
EDTA = Ethylenedioxy-diethylene-dinitrilo-tetraacetic acid Vesicular Formations While not to be limited to any mechanism of action or any theory, the formulations of the invention may form vesicles or ESAs characterized by their adaptability, deformability, or penetrability.

The term vesicle or aggregate "adaptability" which governs the "tolerable surface curvature" is defined as the ability of a given vesicle or aggregate to change easily its properties, such as shape, elongation ratio, and surface to volume ratio. The vesicles of this invention may be characterized by their ability to adjust the aggregates' shape and properties to the anisotropic stress caused by pore crossing. Sufficient adaptability implies that a vesicle or an aggregate can sustain different unidirectional forces or stress, such as one caused by pressure, without extensive fragmentation, which defines a "stable" aggregate. If an aggregate passes through a barrier fulfilling this condition the terms "adaptability" and (shape) "deformability" plus "permeability" are essentially equivalent. A "barrier" in the context of this invention is (as in, for example, EP 0 475 160 and WO 98/17255) a body with through-extending narrow pores, such narrow pores having a radius which is at least 25% smaller than the radius of the ESAs (considered as spherical) before said ESAs permeate through such pores.

The term "narrow" used in connection with a pore implies that the pore radius is significantly, typically at least 25%, smaller than the radius of the entity tested with regard to its ability to cross the pore. The necessary difference typically should be greater for the narrower pores. Using 25% limit is therefore quite suitable for >150 nm diameter whereas >100% difference requirement is more appropriate for the smaller systems, e.g., with <50 nm diameter. For diameters around 20 nm, aggregate diameter difference of at least 200% is often required.

The term "semipermeable" used in connection with a barrier implies that a solution can cross transbarrier openings whereas a suspension of non-adaptable aggregates (large enough for the above definition of "narrow" pores to apply) cannot. Conventional lipid vesicles (liposomes) made from any common phosphatidylcholine in the gel lamellar phase or else from any biological phosphatidylcholine/cholesterol 1/1 mol/mol mixture or else comparably large oil droplets, all having the specified relative diameter, are three examples for such non-adaptable aggregates.

The term "stable" means that the tested aggregates do not change their diameter spontaneously or under the transport related mechanical stress (e.g. during passage through a semipermeable barrier) unacceptably, which most often means only to a pharmaceutically acceptable degree. A 20-40% change is normally considered acceptable; the halving or doubling of aggregate diameter is borderline and a greater change in diameter is typically unacceptable. Alternatively and very conveniently, the change in aggregate diameter resulting from pore crossing under pressure is used to assess system stability; the same criteria are then applied as for "narrow" pores, mutatis mutandis. To obtain the correct value for aggregate diameter change, a correction for flux/vortex effects may be necessary. These procedures are described in greater detail in the publications of the applicant in Cevc et. al., Biochim. Biophys. Acta 2002; 1564: 21-30.

Non-destructing passage of ultradeformable, mixed lipid aggregates through narrow pores in a semi-permeable barrier is thus diagnostic of high aggregate adaptability. If pore radius is two times smaller than the average aggregate radius the aggregate must change its shape and surface-to-volume ratio at least 100% to pass without fragmentation through the barrier. An easy and reversible change in aggregate shape inevitably implies high aggregate deformability and requires large surface-to-volume ratio adaptation. A change in surface-to-volume ratio per se implies: a) high volume compressibility, e.g. in the case of compact droplets containing material other than, and immiscible with, the suspending fluid; b) high aggregate membrane permeability, e.g. in the case of vesicles that are free to exchange fluid between inner and outer vesicle volume.

The vesicles or ESAs of the present invention have "adaptability" that can be assessed using the following method: 1) measure the flux ($j_a$) of the aggregate or ESA suspension through a semi-permeable membrane (e.g., gravimetrically) for different transport-driving trans barrier pressures ($\Delta p$); 2) calculate the pressure dependence of barrier penetratability P for the suspension by dividing each measured flux value by the corresponding pressure value: $P(\Delta p)=j_a(\Delta p)/\Delta p$; 3) monitor the ratio of final and starting vesicle diameter 2 $r_{ves}(\Delta p)/2\ r_{ves,0}$ (e.g. by dynamic light scattering), wherein 2 $r_{ves}(\Delta p)$ is the vesicle diameter after semi-permeable barrier passage driven by $\Delta p$ and 2 $r_{ves,0}$ is the starting vesicle diameter, and if necessary make corrections for the flow-effects; and 4) aligh both data sets $P(\Delta p)$ vs. $r_{ves}(\Delta p)/r_{ves,0}$ to determine the co-existence range for high aggregate adaptability and stability.

It is also useful, but not essential, to parameterize experimental penetratability data within the framework of Maxwell-approximation in terms of the necessary pressure value p* and in terms of maximum penetratability value $P_{max}$. It is plausible to sum-up all the contributions to a moving aggregate energy (deformation energy/ies, thermal energy, the shearing work, etc.) into a single, total energy. The equilibrium population density of aggregate's energetic levels then may be taken to correspond to Maxwell's distribution. All aggregates with a total energy greater than the activation energy, E f $E_A$, are finally concluded to penetrate the barrier. The pore-crossing probability for such aggregates is then given by the following formula, where e is dimensionless aggregate energy units of the activation energy $E_A$:

$$P(e) = 1 - \mathrm{erf}\left(\sqrt{\frac{1}{e}}\right) + \sqrt{\frac{4}{\pi e}} \cdot \exp\left[-\frac{1}{e}\right]$$

It is therefore plausible to represent barrier penetratability of a given suspension as a function of transport driving pressure by the following formula, where $P_{max}$ is the maximum possible penetratability of a given barrier (for the aggregates with zero transport resistance this penetrability is identical to the penetrability of the suspending medium flux), and p* is an adjustable parameter that describes the pressure sensitivity, and thus the transport resistance, of the tested system (for barriers with a fixed pore radius this sensitivity is a function of aggregate properties solely; for non-interacting particles the sensitivity is dominated by aggregate adaptability, allowing to make the assumption: $a_a$ proportional to 1/p*

$$P(p) = p_{max} \cdot \left\{ 1 - \mathrm{erf}\left(\sqrt{\frac{p^*}{p}}\right) + \sqrt{\frac{4p^*}{\pi p}} \cdot \exp\left[-\frac{p^*}{p}\right] \right\}$$

Other methods of testing deformability and adaptability which may be used to characterize the compsitions of the invention are set forth, for example, in U.S. Patent Application Publication Nos. 2004/0071767 and 2004/0105881, each herein incorporated by reference as if set forth herein in their entirety.

Methods of Administration/Treatment

In another embodiment, the invention provides methods of treating disorders related to fatty acid deficiencies, fatty acid metabolism, hypolididemia, hypertriglyceridemia and hypercholesterolemia comprising administering to a subject in need thereof a pharmaceutical composition comprising at least one phospholipid and one nonionic surfactant. In another embodiment, the invention provides methods of treating disorders related to fatty acid deficiencies, fatty acid metabolism, hypolididemia, hypertriglyceridemia and hypercholesterolemia comprising administering to a subject in need thereof a pharmaceutical composition consisting essentially of at least one phospholipid and one nonionic surfactant, a pharmaceutically acceptable carrier, and optionally buffers, antioxidants, preservatives, microbicides, antimicrobials, emollients, co-solvents, and/or thickeners. In another embodiment, the invention provides methods of treating disorders related to fatty acid deficiencies, fatty acid metabolism, hypolididemia, hypertriglyceridemia and hypercholesterolemia comprising administering to a subject in need thereof a pharmaceutical composition consisting of at least one phospholipid and one nonionic surfactant, a pharmaceutically acceptable carrier, and one or more of the following: buffers, antioxidants, preservatives, microbicides, antimicrobials, emollients, co-solvents, and thickeners.

In another embodiment, the invention provides methods of treating disorders related to inflammation, asthma, bronchospasm, atherothrombatic cardiovascular disorders, venous thrombatic disorders, pain, dysmenorrheal, hypercholesterolemia, hypertriglyceridemia, fatty acid metabolism, metal or other toxicity, Alzheimers disease, gout or macular degeneration, such as AMD, or fungal infection, comprising administering to a subject in need thereof a pharmaceutical composition comprising at least one phospholipid and one nonionic surfactant, wherein the pharmaceutical composition sequesters organic matter upon administration. In another embodiment, the invention provides methods of treating disorders related to inflammation, asthma, bronchospasm, atherothrombatic cardiovascular disorders, venous thrombatic disorders, pain, dysmenorrheal, hypercholesterolemia, hypertriglyceridemia, fatty acid metabolism, metal or other toxicity, Alzheimers disease, gout or macular degeneration, such as AMD, or fungal infection comprising administering to a subject in need thereof a pharmaceutical composition consisting essentially of at least one phospholipid and one nonionic surfactant, a pharmaceutically acceptable carrier, and optionally buffers, antioxidants, preservatives, microbicides, antimicrobials, emollients, co-solvents, and/or thickeners, wherein the pharmaceutical composition sequesters organic matter upon administration. In another embodiment, the invention provides methods of treating disorders related to inflammation, asthma, bronchospasm, atherothrombatic cardiovascular disorders, venous thrombatic disorders, pain, dysmenorrheal, hypercholesterolemia, hypertriglyceridemia, fatty acid metabolism, metal or other toxicity, Alzheimers disease, gout or macular degeneration, such as AMD, or fungal infection comprising administering to a subject in need thereof a pharmaceutical composition consisting of at least one phospholipid and one nonionic surfactant, a pharmaceutically acceptable carrier, and one or more of the following: buffers, antioxidants, preservatives, microbicides, antimicrobials, emollients, co-solvents, and thickeners, wherein the pharmaceutical composition sequesters organic matter upon administration.

Packages

In another embodiment, the invention provides a pharmaceutical package or kit comprising one or more containers filled with the formulation of the invention, and instructions for administration of the formulation to a patient or subject in need thereof for treating disorders related to fatty acid deficiencies, fatty acid metabolism, hypertriglyceridemia and hypercholesterolemia. In certain embodiments, the formulation comprises one or more phospholipids and one or more surfactants. In certain embodiments, the formulation does not comprise a non-lipid non-surfactant pharmaceutically active agent that has received marketing or regulatory approval in any country for the treatment of disorders related to fatty acid deficiencies, fatty acid metabolism, hypertriglyceridemia and hypercholesterolemia, or other disorder listed above. In various embodiments, the container comprises a formulation formulated as a suspension, emulsion, gel, cream, lotion, spray, film forming solution or lacquer. The invention provides packages or kits that can be used in any of the above-described methods.

EXAMPLES

Example 1

Example Formulations

The Following Exemplary Formulations for Topical Application May be Prepared by the Following Procedure:

1. Organic phase production, which contains all lipophilic excipients

The organic phase is produced by weighing the lipid, the surfactant, any additional lipophilic excipients into suitable containers followed by mixing these components into anoptically isotropic phase which appears as a clear solution. During mixing, the organic phase will be heated up, but temperature must not rise above 45° C.

2. Aqueous Phase Production

The aqueous phase is prepared by weighing the non-lipophilic components and water, which serves as solvent, into suitable containers and then mixing these components into a clear solution. During mixing, the temperature will be elevated to 40° C.

3. Production of a Concentrated Intermediate by Combination of Both Phases

The isotropic organic phase and the clear aqueous phase are combined under stirring in a suitable vessel. Before and during the combination the temperature of both phases must be kept between 35° C. and 45° C. The resulting intermediate is homogenised mechanically at 40° C. Before starting homogenisation, the pressure in the production vessel is lowered to −0.08 MPa. The desired average carrier size is typically reached after 10 minutes of homogenisation.

Three process parameters must be controlled carefully during the production of the concentrated intermediate: temperature, homogeniser circulation velocity, and overall processing time.

4. Production of the Final Bulk Product by Mixing the Concentrated Intermediate with Dilution Buffer.

The concentrated intermediate is diluted with the dilution buffer to the intended final concentration. The mixture is carefully stirred in the mixing vessel at 20° C. to homogeneity.

Table 8 describes the amounts of surfactant and lipids, and other excipients in the tranfersome formulations, described in terms of the percent of the total amount of formulation.

TABLE 8

Preferred Formulations

Table 8A: This table lists the relative amounts of each of the components of Preferred Formulations

| | Lipid mg/g | Surfactant mg/g (1 to 10% by wt.) | Buffer (pH 4-7.5) | Antimicrobials (0-10 mg/g) | Antioxidants (0-10 mg/g) | Emollient (0-50 mg/g) | Other (0-50 mg/g) | Chelator (0-25 mg/g) |
|---|---|---|---|---|---|---|---|---|
| 1 | 47.944 | 42.056 | 4 | 5.000 | 0.700 | 30.000 | 30.000 | 3.000 |
| 2 | 53.750 | 31.250 | 4 | 5.000 | 0.700 | 30.000 | 15.000 | 3.000 |
| 3 | 90.561 | 79.439 | 4 | 5.000 | 0.700 | 30.000 | 30.000 | 3.000 |
| 4 | 47.944 | 42.056 | 5 | 5.000 | 0.700 | 30.000 | 30.000 | 3.000 |
| 5 | 50.607 | 44.393 | 5 | 5.000 | 0.700 | 0.000 | 10.000 | 3.000 |
| 6 | 90.561 | 79.439 | 5 | 5.000 | 0.700 | 30.000 | 30.000 | 3.000 |
| 7 | 49.276 | 43.224 | 6.5 | 5.000 | 0.700 | 30.000 | 30.000 | 3.000 |
| 8 | 53.750 | 31.250 | 6.5 | 5.000 | 0.200 | 30.000 | 0.000 | 3.000 |
| 9 | 90.561 | 79.439 | 6.5 | 5.000 | 0.200 | 30.000 | 20.000 | 3.000 |
| 10 | 41.351 | 48.649 | 4 | 5.000 | 0.200 | 30.000 | 30.000 | 3.000 |
| 11 | 47.882 | 37.118 | 4 | 5.000 | 0.200 | 0.000 | 30.000 | 3.000 |
| 12 | 95.764 | 74.236 | 4 | 5.000 | 0.200 | 30.000 | 30.000 | 3.000 |
| 13 | 65.676 | 24.324 | 5 | 5.000 | 0.200 | 0.000 | 25.000 | 3.000 |
| 14 | 62.027 | 22.973 | 5 | 5.000 | 0.200 | 0.000 | 30.000 | 3.000 |
| 15 | 124.054 | 45.946 | 5 | 5.000 | 0.200 | 15.000 | 36.510 | 3.000 |
| 16 | 62.687 | 32.313 | 6.5 | 5.000 | 0.200 | 15.000 | 0.000 | 3.000 |
| 17 | 41.853 | 43.147 | 6.5 | 5.000 | 0.200 | 30.000 | 30.000 | 3.000 |
| 18 | 95.764 | 74.236 | 6.5 | 5.000 | 0.200 | 0.000 | 30.000 | 3.000 |
| 19 | 47.882 | 37.118 | 6.5 | 5.000 | 0.200 | 0.000 | 0.000 | 3.000 |
| 20 | 45.000 | 45.000 | 6.5 | 5.000 | 0.200 | 0.000 | 0.000 | 1.000 |
| 21 | 31.935 | 58.065 | 5 | 5.000 | 0.200 | 30.000 | 15.000 | 3.000 |
| 22 | 42.500 | 42.500 | 6.5 | 5.000 | 0.200 | 30.000 | 0.000 | 3.000 |
| 23 | 38.276 | 51.724 | 4 | 5.000 | 0.200 | 0.000 | 36.510 | 3.000 |
| 24 | 42.500 | 42.500 | 4 | 5.000 | 0.200 | 0.000 | 15.000 | 3.000 |
| 25 | 85.000 | 85.000 | 4 | 5.000 | 0.200 | 30.000 | 30.000 | 3.000 |
| 26 | 38.276 | 51.724 | 5 | 5.000 | 0.200 | 30.000 | 0.000 | 1.000 |
| 27 | 36.429 | 48.571 | 5 | 5.000 | 0.200 | 30.000 | 30.000 | 3.000 |
| 28 | 72.299 | 97.701 | 5 | 5.000 | 0.200 | 30.000 | 15.000 | 3.000 |
| 29 | 46.250 | 46.250 | 6.5 | 5.000 | 0.700 | 0.000 | 20.000 | 3.000 |
| 30 | 38.804 | 46.196 | 6.5 | 5.000 | 0.700 | 15.000 | 30.000 | 3.000 |
| 31 | 36.667 | 33.333 | 6.5 | 5.000 | 0.700 | 30.000 | 10.000 | 3.000 |
| 32 | 66.667 | 23.333 | 4 | 5.000 | 0.200 | 0.000 | 0.000 | 3.000 |
| 33 | 45.833 | 41.667 | 4 | 5.000 | 0.200 | 30.000 | 0.000 | 3.000 |
| 34 | 31.957 | 38.043 | 4 | 5.000 | 0.200 | 0.000 | 30.000 | 3.000 |
| 35 | 47.143 | 42.857 | 5 | 5.000 | 0.200 | 30.000 | 25.000 | 1.000 |
| 36 | 96.905 | 88.095 | 5 | 5.000 | 0.200 | 30.000 | 20.000 | 3.000 |
| 37 | 31.957 | 38.043 | 5 | 5.000 | 0.200 | 0.000 | 30.000 | 3.000 |
| 38 | 35.455 | 54.545 | 6.5 | 5.000 | 0.700 | 30.000 | 0.000 | 3.000 |
| 39 | 84.457 | 100.543 | 6.5 | 5.000 | 0.700 | 30.000 | 30.000 | 3.000 |
| 40 | 89.048 | 80.952 | 6.5 | 5.000 | 0.700 | 30.000 | 30.000 | 3.000 |
| 41 | 41.087 | 48.913 | 4 | 5.000 | 0.700 | 30.000 | 36.510 | 3.000 |
| 42 | 45.280 | 39.720 | 4 | 5.000 | 0.700 | 0.000 | 0.000 | 3.000 |

TABLE 8-continued

Preferred Formulations

| | | | | | | | | |
|---|---|---|---|---|---|---|---|---|
| 43 | 107.500 | 62.500 | 4 | 5.000 | 0.700 | 30.000 | 30.000 | 3.000 |
| 44 | 77.243 | 67.757 | 4 | 5.000 | 0.700 | 0.000 | 15.000 | 3.000 |
| 45 | 45.280 | 39.720 | 5 | 5.000 | 0.700 | 0.000 | 20.000 | 3.000 |
| 46 | 90.561 | 79.439 | 5 | 5.000 | 0.700 | 0.000 | 30.000 | 3.000 |
| 47 | 47.944 | 42.056 | 5 | 5.000 | 0.700 | 0.000 | 10.000 | 3.000 |
| 48 | 50.607 | 44.393 | 5.5 | 5.000 | 0.700 | 30.000 | 0.000 | 1.000 |
| 49 | 107.500 | 62.500 | 5.5 | 5.000 | 0.700 | 30.000 | 0.000 | 3.000 |
| 50 | 47.944 | 42.056 | 5.5 | 5.000 | 0.700 | 30.000 | 30.000 | 3.000 |
| 51 | 46.364 | 38.636 | 4 | 5.000 | 0.200 | 30.000 | 25.000 | 3.000 |
| 52 | 46.364 | 38.636 | 4 | 5.000 | 0.200 | 0.000 | 20.000 | 3.000 |
| 53 | 46.098 | 43.902 | 5 | 5.000 | 0.200 | 15.000 | 30.000 | 3.000 |
| 54 | 43.537 | 41.463 | 5 | 5.000 | 0.200 | 30.000 | 0.000 | 3.000 |
| 55 | 45.000 | 45.000 | 5 | 5.000 | 0.200 | 0.000 | 30.000 | 3.000 |
| 56 | 59.492 | 30.508 | 6.5 | 5.000 | 0.200 | 30.000 | 30.000 | 3.000 |
| 57 | 39.054 | 45.946 | 6.5 | 5.000 | 0.200 | 0.000 | 0.000 | 3.000 |
| 58 | 35.854 | 34.146 | 6.5 | 5.000 | 0.200 | 30.000 | 0.000 | 3.000 |
| 59 | 50.000 | 40.000 | 6.5 | 5.000 | 0.700 | 30.000 | 30.000 | 3.000 |
| 60 | 38.571 | 51.429 | 6.5 | 5.000 | 0.700 | 30.000 | 30.000 | 3.000 |
| 61 | 41.954 | 50.546 | 6.5 | 5.000 | 0.700 | 30.000 | 30.000 | 3.000 |
| 62 | 42.632 | 47.368 | 6.5 | 5.000 | 0.700 | 30.000 | 30.000 | 3.000 |
| 63 | 46.098 | 43.902 | 6.5 | 5.000 | 0.700 | 30.000 | 30.000 | 3.000 |
| 64 | 39.721 | 50.279 | 6.5 | 5.000 | 0.700 | 30.000 | 30.000 | 3.000 |
| 65 | 44.198 | 50.802 | 6.5 | 5.000 | 0.700 | 30.000 | 30.000 | 3.000 |
| 66 | 46.453 | 51.047 | 6.5 | 5.000 | 0.700 | 30.000 | 30.000 | 3.000 |
| 67 | 51.221 | 43.779 | 6.5 | 5.000 | 0.700 | 30.000 | 30.000 | 3.000 |
| 68 | 54.167 | 43.333 | 6.5 | 5.000 | 0.700 | 30.000 | 30.000 | 3.000 |
| 69 | 66.440 | 23.560 | 6.5 | 5.000 | 0.700 | 30.000 | 30.000 | 3.000 |
| 70 | 66.440 | 23.560 | 6.5 | 5.000 | 0.700 | 30.000 | 30.000 | 3.000 |
| 71 | 66.440 | 23.560 | 6.5 | 5.000 | 0.700 | 30.000 | 30.000 | 3.000 |
| 72 | 40.000 | 50.000 | 6.5 | 5.000 | 0.700 | 30.000 | 30.000 | 3.000 |
| 73 | 40.000 | 50.000 | 6.5 | 5.000 | 0.700 | 30.000 | 30.000 | 3.000 |
| 74 | 40.000 | 50.000 | 5.5 | 0.000 | 0.700 | 30.000 | 30.000 | 3.000 |
| 75 | 40.000 | 50.000 | 6.5 | 5.000 | 0.700 | 30.000 | 30.000 | 3.000 |
| 76 | 40.000 | 50.000 | 6.5 | 5.000 | 0.700 | 30.000 | 30.000 | 3.000 |
| 77 | 40.000 | 50.000 | 6.5 | 5.000 | 0.700 | 30.000 | 30.000 | 3.000 |
| 78 | 66.440 | 23.560 | 6.5 | 5.000 | 0.700 | 30.000 | 30.000 | 3.000 |
| 79 | 66.440 | 23.560 | 6.5 | 5.000 | 0.700 | 30.000 | 30.000 | 3.000 |
| 80 | 40.000 | 50.000 | 5.5 | 0.000 | 0.700 | 30.000 | 30.000 | 3.000 |
| 81 | 40.000 | 50.000 | 5.5 | 5.000 | 0.700 | 30.000 | 30.000 | 3.000 |
| 82 | 44.444 | 55.556 | 5.5 | 5.000 | 0.700 | 30.000 | 30.000 | 3.000 |
| 83 | 66.440 | 23.560 | 5.5 | 5.000 | 0.700 | 30.000 | 30.000 | 3.000 |
| 84 | 54.000 | 36.000 | 4 | 5.000 | 0.700 | 30.000 | 30.000 | 3.000 |
| 85 | 50.000 | 40.000 | 4 | 5.000 | 0.700 | 30.000 | 30.000 | 3.000 |
| 86 | 48.611 | 38.889 | 4 | 5.000 | 0.700 | 30.000 | 30.000 | 3.000 |
| 87 | 46.575 | 38.425 | 4 | 5.000 | 0.700 | 30.000 | 30.000 | 3.000 |
| 88 | 46.575 | 38.425 | 4 | 5.000 | 0.700 | 30.000 | 30.000 | 3.000 |
| 89 | 46.575 | 38.425 | 4 | 5.000 | 0.700 | 30.000 | 30.000 | 3.000 |
| 90 | 50.000 | 40.000 | 4.5 | 5.000 | 0.700 | 30.000 | 30.000 | 3.000 |
| 91 | 94.444 | 75.556 | 4 | 5.000 | 0.700 | 30.000 | 30.000 | 3.000 |
| 92 | 46.712 | 38.288 | 4 | 5.000 | 0.700 | 30.000 | 30.000 | 3.000 |
| 93 | 48.889 | 39.111 | 4 | 5.000 | 0.700 | 30.000 | 30.000 | 3.000 |
| 94 | 39.721 | 50.279 | 6.5 | 5.000 | 0.700 | 30.000 | 30.000 | 3.000 |
| 95 | 90.000 | 0.000 | 6.5 | 5.000 | 0.700 | 30.000 | 30.000 | 3.000 |
| 96 | 68.700 | 8.500 | 7.5 | 5.000 | 0.700 | 30.000 | 36.510 | 1.000 |
| 97 | 71.460 | 4.720 | 7.8 | 5.000 | 0.700 | 50.000 | 35.000 | 3.000 |
| 99 | 71.460 | 4.720 | 7.8 | 5.000 | 0.700 | 50.000 | 15.000 | 3.000 |
| 98 | 71.460 | 4.720 | 7.8 | 0.000 | 0.700 | 50.000 | 15.000 | 3.000 |
| 100 | 71.460 | 4.720 | 7.8 | 0.000 | 0.700 | 50.000 | 35.000 | 3.000 |
| 101 | 46.575 | 38.425 | 4 | 0.000 | 0.700 | 0.000 | 0.000 | 3.000 |
| 102 | 46.575 | 38.425 | 4 | 0.000 | 0.700 | 0.000 | 0.000 | 3.000 |
| 103 | 54.643 | 30.357 | 4 | 5.000 | 0.700 | 0.000 | 0.000 | 3.000 |
| 104 | 39.72 | 50.279 | 6.5 | 5.000 | 0.700 | 30.000 | 30.000 | 3.000 |
| 105 | 90.00 | | 6.5 | 5.000 | 0.700 | 30.000 | 30.000 | 3.000 |
| 106 | 46.57 | 38.425 | 4 | | 0.700 | | | 3.000 |
| 107 | 46.75 | 38.425 | 4 | | 0.700 | | | 3.000 |
| 108 | 54.64 | 30.357 | 4 | | 0.700 | | | 3.000 |
| 109 | 46.364 | 38.636 | 4 | 5.000 | 0.200 | 30.000 | 25.000 | 3.000 |
| 110 | 46.364 | 38.636 | 4 | 5.000 | 0.200 | 0.000 | 20.000 | 3.000 |
| 111 | 46.098 | 43.902 | 5 | 5.000 | 0.200 | 15.000 | 30.000 | 3.000 |
| 112 | 43.537 | 41.463 | 5 | 5.000 | 0.200 | 30.000 | 0.000 | 3.000 |
| 113 | 45.000 | 45.000 | 5 | 5.000 | 0.200 | 0.000 | 30.000 | 3.000 |
| 114 | 59.492 | 30.508 | 6.5 | 5.000 | 0.200 | 30.000 | 30.000 | 3.000 |
| 115 | 39.054 | 45.946 | 6.5 | 5.000 | 0.200 | 0.000 | 0.000 | 3.000 |
| 116 | 35.854 | 34.146 | 6.5 | 5.000 | 0.200 | 30.000 | 0.000 | 3.000 |
| 117 | 50.000 | 40.000 | 6.5 | 5.000 | 0.700 | 30.000 | 30.000 | 3.000 |
| 118 | 38.571 | 51.429 | 6.5 | 5.000 | 0.700 | 30.000 | 30.000 | 3.000 |
| 119 | 41.954 | 50.546 | 6.5 | 5.000 | 0.700 | 30.000 | 30.000 | 3.000 |
| 120 | 42.632 | 47.368 | 6.5 | 5.000 | 0.700 | 30.000 | 30.000 | 3.000 |

TABLE 8-continued

Preferred Formulations

| | | | | | | | | |
|---|---|---|---|---|---|---|---|---|
| 121 | 46.098 | 43.902 | 6.5 | 5.000 | 0.700 | 30.000 | 30.000 | 3.000 |
| 122 | 39.721 | 50.279 | 6.5 | 5.000 | 0.700 | 30.000 | 30.000 | 3.000 |
| 123 | 44.198 | 50.802 | 6.5 | 5.000 | 0.700 | 30.000 | 30.000 | 3.000 |
| 124 | 46.453 | 51.047 | 6.5 | 5.000 | 0.700 | 30.000 | 30.000 | 3.000 |
| 125 | 51.221 | 43.779 | 6.5 | 5.000 | 0.700 | 30.000 | 30.000 | 3.000 |
| 126 | 54.167 | 43.333 | 6.5 | 5.000 | 0.700 | 30.000 | 30.000 | 3.000 |
| 127 | 66.440 | 23.560 | 6.5 | 5.000 | 0.700 | 30.000 | 30.000 | 3.000 |
| 128 | 66.440 | 23.560 | 6.5 | 5.000 | 0.700 | 30.000 | 30.000 | 3.000 |
| 129 | 66.440 | 23.560 | 6.5 | 5.000 | 0.700 | 30.000 | 30.000 | 3.000 |

Table 8B: The table lists the specific components of the formulas listed above.

| Formula | Lipid | Surfactant | Buffer | Antimicrobial | Antioxidants | Emollient | Chelator | Other |
|---|---|---|---|---|---|---|---|---|
| 1-4 | Sphingomyelin, e.g., brain | Tween 80 | Lactate | Benzyl alcohol or paraben | BHT (0.200) sodium metabisulfite (0.500) | Glycerol | EDTA | Ethanol |
| 5-7 | Sphingomyelin, lauroyl | Brij 98 | Acetate | Benzyl alcohol or paraben | BHT (0.200) sodium metabisulfite (0.500) | Glycerol | EDTA | Ethanol |
| 8-12 | Phosphatidyl choline + Phosphatidylglycerol | Brij 98 | Phosphate | Benzyl alcohol or paraben | HTHQ | Glycerol | EDTA | Ethanol |
| 13-16 | Phosphatidyl choline + phosphatidylinositol | Span 20 | Acetate | Benzyl alcohol or paraben | HTHQ | Glycerol | EDTA | Ethanol |
| 17-18 | Phosphatidyl choline + phosphatidic acid | Tween 80 | Phosphate | Benzyl alcohol or paraben | BHT | Glycerol | EDTA | Ethanol |
| 19 | Phosphatidyl choline + phosphatidic acid | Brij 98 + Tween 80 | Phosphate | Benzyl alcohol or paraben | BHT | Glycerol | EDTA | Ethanol |
| 20 | Phosphatidyl choline + phosphatidic acid | Span 20 + Tween 80 | Phosphate | Benzyl alcohol or paraben | BHT | Glycerol | EDTA | Ethanol |
| 21 | Phosphatidyl choline | Cremophor + Span 20 | Lactate | Thimerosal | BHA | Glycerol | EDTA | Ethanol |
| 22 | Phosphatidyl choline | Cremophor + Tween 80 | Lactate | Thimerosal | BHA | Glycerol | EDTA | Ethanol |
| 23-28 | Phosphatidyl choline | Cremophor | Lactate | Thimerosal | BHA | Glycerol | EDTA | Ethanol |
| 29-30 | Phosphatidyl ethanolamine | Tween 80 | Phosphate | Thimerosal | BHT (0.200) sodium metabisulfite (0.500) | Glycerol | EDTA | Ethanol |
| 31 | Phosphatidyl ethanolamine | Brij 98 + Tween 80 | Phosphate | Thimerosal | BHT (0.200) sodium metabisulfite (0.500) | Glycerol | EDTA | Ethanol |
| 32 | Phosphatidyl glycerol | Cremophor + Brij 98 | Acetate | Benzyl alcohol or paraben | BHT | Glycerol | EDTA | Ethanol |
| 33-37 | Phosphatidyl glycerol | Brij 98 | Acetate | Benzyl alcohol or paraben | BHT | Glycerol | EDTA | Ethanol |
| 38-40 | Phosphatidyl ethanolamine | Cremophor | phosphate | Benzyl alcohol or paraben | BHT (0.200) sodium metabisulfite (0.500) | Glycerol | EDTA | Ethanol |
| 41-47 | Phosphatidyl glycerol | Tween 80 | Propionate | Benzyl alcohol or paraben | BHT (0.200) sodium metabisulfite (0.500) | Glycerol | EDTA | Ethanol |
| 48-50 | Phosphatidyl serine | Brij 98 | Phosphate | Thimerosal | BHT (0.200) sodium metabisulfite (0.500) | Glycerol | EDTA | Ethanol |
| 51-58 | Phosphatidyl glycerol | Brij 98 | Acetate | Benzyl alcohol or paraben | BHT | Glycerol | EDTA | Ethanol |
| 59-68 | Phosphatidyl choline | Tween 80 | Phosphate | Benzyl alcohol or paraben | BHT (0.200) sodium metabisulfite (0.500) | Glycerol | EDTA | Ethanol |
| 69-71 | Phosphatidyl choline | Brij 98 | Phosphate | Benzyl alcohol or paraben | BHT (0.200) sodium metabisulfite (0.500) | Glycerol | EDTA | Ethanol |
| 72-73 | Phosphatidyl choline | Tween 80 | Phosphate | Benzyl alcohol or paraben | BHT (0.200) sodium | Glycerol | EDTA | Ethanol |

TABLE 8-continued

Preferred Formulations

| | | | | | | | | |
|---|---|---|---|---|---|---|---|---|
| 74 | Phosphatidyl choline | Tween 80 | Acetate | | metabisulfite (0.500) BHT (0.200) sodium metabisulfite (0.500) | Glycerol | EDTA | Ethanol |
| 75 | Phosphatidyl choline | Tween 80 | Phosphate | Benzyl alcohol or paraben | BHT (0.200) sodium metabisulfite (0.500) | Glycerol | EDTA | Ethanol |
| 76 | Phosphatidyl choline | Brij 98 | Phosphate | Benzalkonium chloride | BHT (0.200) sodium metabisulfite (0.500) | Glycerol | EDTA | Ethanol |
| 77 | Phosphatidyl choline | Tween 80 | Phosphate | Benzyl alcohol or paraben | BHT (0.200) sodium metabisulfite (0.500) | Glycerol | EDTA | Ethanol |
| 78 | Phosphatidyl choline | Brij 98 | Phosphate | Benzalkonium chloride | BHT (0.200) sodium metabisulfite (0.500) | Glycerol | EDTA | Ethanol |
| 79 | Phosphatidyl choline | Brij 98 | Phosphate | Benzyl alcohol or paraben | BHT (0.200) sodium metabisulfite (0.500) | Glycerol | EDTA | Ethanol |
| 80 | Phosphatidyl choline | Tween 80 | Acetate | | BHT (0.200) sodium metabisulfite (0.500) | Glycerol | EDTA | Ethanol |
| 81 | Phosphatidyl choline | Tween 80 | Acetate | Benzyl alcohol or paraben | BHT (0.200) sodium metabisulfite (0.500) | Glycerol | EDTA | Ethanol |
| 82-83 | Phosphatidyl choline | Tween 80 | Acetate | Benzyl alcohol or paraben | BHT (0.200) sodium metabisulfite (0.500) | Glycerol | EDTA | Ethanol |
| 84-88 | Phosphatidyl choline | Tween 80 | Acetate | Benzyl alcohol or paraben | BHA (0.200) sodium metabisulfite (0.500) | Glycerol | EDTA | Ethanol |
| 89 | Phosphatidyl choline | Tween 80 | Acetate | Benzyl alcohol or paraben | BHT (0.200) sodium metabisulfite (0.500) | Glycerol | EDTA | Ethanol |
| 90-93 | Phosphatidyl choline | Tween 80 | Acetate | Benzyl alcohol or paraben | BHT (0.200) sodium metabisulfite (0.500) | Glycerol | EDTA | Ethanol |
| 94-96 | Phosphatidyl choline | Tween 80 | Phosphate | Benzyl alcohol or paraben | BHT (0.200) sodium metabisulfite (0.500) | Glycerol | EDTA | Ethanol |
| 97-98 | Phosphatidyl choline | Tween 80 | Phosphate | Benzyl alcohol or paraben | BHT (0.200) sodium metabisulfite (0.500) | Glycerol | EDTA | Ethanol |
| 99-100 | Phosphatidyl choline | Tween 80 | Phosphate | | BHT (0.200) sodium metabisulfite (0.500) | Glycerol | EDTA | Ethanol |
| 101-103 | Phosphatidyl choline | Tween 80 | Acetate | | BHT (0.200) sodium metabisulfite (0.500) | | EDTA | |
| 104 | Phosphatidyl choline | Tween 80 | Phosphate | Benzyl alcohol or paraben | BHT (0.200) sodium metabisulfite (0.500) | Glycerol | EDTA | Ethanol |
| 105 | Phosphatidyl choline | | Phosphate | Benzyl alcohol or paraben | BHT (0.200) sodium metabisulfite (0.500) | Glycerol | EDTA | Ethanol |
| 106-108 | Phosphatidyl choline | Tween 80 | Phosphate | | BHT (0.200) sodium metabisulfite (0.500) | | EDTA | |

TABLE 8-continued

Preferred Formulations

| | | | | | | | | |
|---|---|---|---|---|---|---|---|---|
| 109-116 | Phosphatidyl glycerol and lysophospholipid | Brij 98 | Acetate | Benzyl alcohol or paraben | BHT | Glycerol | EDTA | Ethanol |
| 117-126 | Phosphatidyl choline and lysophospholipid | Tween 80 | Phosphate | Benzyl alcohol or paraben | BHT (0.200) sodium metabisulfite (0.500) | Glycerol | EDTA | Ethanol |
| 127-129 | Phosphatidyl choline and lysophospholipid | Brij 98 | Phosphate | Benzyl alcohol or paraben | BHT (0.200) sodium metabisulfite (0.500) | Glycerol | EDTA | Ethanol |

Example Formulation 1

Formulation 1 comprises sphingomyelin (brain) (47.944 mg/g) as a lipid, Tween 80 (42.056 mg/g) as a surfactant, lactate buffer (pH 4), benzyl alcohol or paraben (5.000 mg/g) as an antimicrobial agent, BHT (0.200 mg/g) and sodium metabisulfite (0.0500 mg/g) as antioxidants, glycerol (30.000 mg/g), EDTA (3.000 mg/g) as a chelating agent, and ethanol (30.000 mg/g).

Example Formulation 2

Formulation 2 comprises sphingomyelin (brain) (53.750 mg/g) as a lipid, Tween 80 (31.250 mg/g) as a surfactant, lactate (pH 4) buffer, benzyl alcohol or paraben (5.000 mg/g) as an antimicrobial agent, BHT (0.200 mg/g) and sodium metabisulfite (0.500 mg/g) as antioxidants, glycerol (30.000 mg/g), EDTA (3.000 mg/g) as a chelating agent, and ethanol (15.000 mg/g).

Example Formulation 3

Formulation 3 comprises sphingomyelin (brain) (90.561 mg/g) as a lipid, Tween 80 (79.439 mg/g) as a surfactant, lactate (pH 4) buffer, benzyl alcohol or paraben (5.000 mg/g) as an antimicrobial agent, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 4

Formulation 4 comprises sphingomyelin (brain) (47.944 mg/g) as a lipid, Tween 80 (42.056 mg/g) as a surfactant, lactate (pH 5) buffer, benzyl alcohol or paraben (5.000 mg/g) as an antimicrobial agent, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 5

Formulation 5 comprises sphingomyelin lauroyl (50.607 mg/g) as a lipid, Brij 98 (44.393 mg/g) as a surfactant, acetate (pH 5) buffer, benzyl alcohol or paraben (5.000 mg/g) as an antimicrobial agent, BHT (0.200 mg/g) and sodium metabisulfite (0.500 mg/g) as antioxidants, EDTA (3.000 mg/g) as a chelating agent, and ethanol (10.000 mg/g).

Example Formulation 6

Formulation 6 comprises sphingomyelin lauroyl (90.561 mg/g) as a lipid, Brij 98 (79.439 mg/g) as a surfactant, acetate (pH 5) buffer, benzyl alcohol or paraben (5.000 mg/g) as as antimicrobial agent, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 7

Formulation 7 comprises sphingomyelin lauroyl (49.276 mg/g) as a lipid, Brij 98 (79.439 mg/g) as a surfactant, acetate (pH 6.5) buffer, benzyl alcohol or paraben (5.000 mg/g) as an antimicrobial agent, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 8

Formulation 8 comprises phosphatidyl choline and phosphatidyl glycerol (53.750 mg/g) as a lipid, Brij 98 (31.250 mg/g) as a surfactant, phosphate (pH 6.5) buffer, benzyl alcohol or paraben (5.000 mg/g) as an antimicrobial agent, HTHQ (0.200 mg/g) as an antioxidant, glycerol (30.000 mg/g), and EDTA (3.000 mg/g) as a chelating agent.

Example Formulation 9

Formulation 9 comprises phosphatidyl choline and phosphatidyl glycerol (90.561 mg/g) as a lipid, Brij 98 (79.439 mg/g) as a surfactant, phosphate (pH 6.5) buffer, benzyl alcohol or paraben (5.000 mg/g) as an antimicrobial agent, HTHQ (0.200 mg/g) as as antioxidant, glycerol (30.000 mg/g), EDTA (3.000 mg/g) as a chelating agent, and ethanol (30.000 mg/g).

Example Formulation 10

Formulation 10 comprises phosphatidyl choline and phosphatidyl glycerol (41.351 mg/g) as a lipid, Brij 98 (48.649 mg/g) as a surfactant, phosphate (pH 4) buffer, benzyl alcohol or paraben (5.000 mg/g) as an antimicrobial agent, HTHQ (0.200 mg/g) as an antioxidant, glycerol (30.000 mg/g), EDTA (3.000 mg/g) as a chelating agent, and ethanol (30.000 mg/g).

Example Formulation 11

Formulation 11 comprises phosphatidyl choline and phosphatidyl glycerol (47.882 mg/g) as a lipid, Brij 98 (37.118 mg/g) as a surfactant, phosphate (pH 4) buffer, benzyl alcohol or paraben (5.000 mg/g) as an antimicrobial agent, HTHQ (0.200 mg/g) as an antioxidant, glycerol, EDTA (3.000 mg/g) as a chelating agent, and ethanol (30.000 mg/g).

Example Formulation 12

Formulation 12 comprises phosphatidyl choline and phosphatidyl glycerol (95.764 mg/g) as a lipid, Brij 98 (74.236 mg/g) as a surfactant, phosphate (pH 4) buffer, benzyl alcohol or paraben (5.000 mg/g) as an antimicrobial agent, HTHQ (0.200 mg/g) as an antioxidant, glycerol (30.000 mg/g), EDTA (3.000 mg/g) as a chelating agent, and ethanol (30.000 mg/g).

Example Formulation 13

Formulation 13 comprises phosphatidyl choline and phosphatidylinositol (66.676 mg/g) as a lipid, Span 20 (24.324 mg/g) as a surfactant, acetate (pH 5) buffer, benzyl alcohol or paraben (5.000 mg/g), HTHQ (0.200 mg/g) as an antioxidant, EDTA (3.000 mg/g) as a chelating agent, and ethanol (25.000 mg/g).

Example Formulation 14

Formulation 14 comprises phosphatidyl choline and phosphatidylinositol (62.027 mg/g) as a lipid, Span 20 (22.973 mg/g) as a surfactant, acetate (pH 5) buffer, benzyl alcohol or paraben (5.000 mg/g) as an antimicrobial agent, HTHQ (0.200 mg/g) as an antioxidant, EDTA (3.000 mg/g) as a chelating agent, and ethanol (30.000 mg/g).

Example Formulation 15

Formulation 15 comprises phosphatidyl choline and phosphatidylinositol (124.054 mg/g) as a lipid, Span 20 (45.946 mg/g) as a surfactant, acetate (pH 5) buffer, benzyl alcohol or paraben (5.000 mg/g) as an antimicrobial agent, HTHQ (0.200 mg/g) as an antioxidant, glycerol (30.000 mg/g), and EDTA (3.000 mg/g) as a chelating agent, and ethanol (36.510 mg/g).

Example Formulation 16

Formulation 16 comprises phosphatidyl choline and phosphatidylinositol (62.687 mg/g) as a lipid, Span 20 (32.313 mg/g) as a surfactant, acetate (pH 6.5) buffer, benzyl alcohol or paraben (5.000 mg/g) as an antimicrobial agent, HTHQ (0.200 mg/g) as an antioxidant, glycerol (30.000 mg/g), EDTA (3.000 mg/g) as a chelating agent.

Example Formulation 17

Formulation 17 comprises phosphatidyl choline and phosphatidic acid (41.853 mg/g) as a lipid, Tween 80 (43.147 mg/g) as a surfactant, phosphate (pH 6.5) buffer, benzyl alcohol or paraben (5.000 mg/g) as an antimicrobial agent, BHT (0.200 mg/g) as an antioxidant, glycerol (30.000 mg/g), EDTA (3.000 mg/g), and ethanol (30.000 mg/g).

Example Formulation 18

Formulation 18 comprises phosphatidyl choline and phosphatidic acid (95.764 mg/g) as a lipid, Tween 80 (74.236 mg/g) as a surfactant, phosphate (pH 6.5) buffer, benzyl alcohol or paraben (5.000 mg/g) as an antimicrobial agent, BHT (0.200 mg/g) as an antioxidant, EDTA (3.000 mg/g), and ethanol (30.000 mg/g).

Example Formulation 19

Formulation 19 comprises phosphatidyl choline and phosphatidic acid (47.882 mg/g) as a lipid, Brij 98 and Tween 80 (37.118 mg/g) as a surfactant, phosphate (pH 6.5) buffer, benzyl alcohol or paraben (5.000 mg/g) as an antimicrobial agent, BHT (0.200 mg/g) as an antioxidant, and EDTA (3.000 mg/g).

Example Formulation 20

Formulation 20 comprises phosphatidyl choline and phosphatidic acid (45.000 mg/g) as a lipid, Span 20 and Tween 80 (45.000 mg/g) as a surfactant, phosphate (pH 6.5) buffer, benzyl alcohol or paraben (5.000 mg/g) as an antimicrobial agent, BHT (0.200 mg/g) as as antioxidant, and EDTA (1.000 mg/g).

Example Formulation 21

Formulation 21 comprises phosphatidyl choline (31.935 mg/g) as a lipid, cremophor and Span 20 (58.065 mg/g) as a surfactant, lactate (pH 5) buffer, thimerosal (5.000 mg/g) as an antimicrobial agent, BHA (0.200 mg/g) as an antioxidant, glycerol (30.000 mg/g), EDTA (3.000 mg/g) as a chelating agent, and ethanol (15.000 mg/g).

Example Formulation 22

Formulation 22 comprises phosphatidyl choline (42.500 mg/g) as a lipid, cremophor and Tween 80 (42.500 mg/g) as a surfactant, lactate (pH 6.5) buffer, thimerosal (5.000 mg/g) as an antimicrobial agent, BHA (0.200 mg/g) as an antioxidant, glycerol (30.000 mg/g), and EDTA (3.000 mg/g) as a chelating agent.

Example Formulation 23

Formulation 23 comprises phosphatidyl choline (38.276 mg/g) as a lipid, cremophor (51.724 mg/g) as a surfactant, lactate (pH 4) buffer, thimerosal (5.000 mg/g) as an antimicrobial agent, BHA (0.200 mg/g) as an antioxidant, EDTA (3.000 mg/g) as a chelating agent, and ethanol (36.510 mg/g).

Example Formulation 24

Formulation 24 comprises phosphatidyl choline (42.500 mg/g) as a lipid, cremophor (42.500 mg/g) as a surfactant, lactate (pH 4) buffer, thimerosal (5.000 mg/g) as an antimicrobial agent, BHA (0.200 mg/g) as an antioxidant, EDTA (3.000 mg/g) as a chelating agent, and ethanol (15.000 mg/g).

Example Formulation 25

Formulation 25 comprises phosphatidyl choline (85.000 mg/g) as a lipid, cremophor (85.000 mg/g) as a surfactant, lactate (pH 4) buffer, thimerosal (5.000 mg/g) as an antimicrobial agent, BHA (0.200 mg/g) as an antioxidant, EDTA (3.000 mg/g) as a chelating agent, and ethanol (30.000 mg/g).

Example Formulation 26

Formulation 26 comprises phosphatidyl choline (38.276 mg/g) as a lipid, cremophor (51.276 mg/g) as a surfactant, lactate (pH 5) buffer, thimerosal (5.000 mg/g) as an antimicrobial agent, BHA (0.200 mg/g) as an antioxidant, and EDTA (1.000 mg/g) as a chelating agent.

Example Formulation 27

Formulation 27 comprises phosphatidyl choline (36.429 mg/g) as a lipid, cremophor (48.571 mg/g) as a surfactant, lactate (pH 5) buffer, thimerosal (5.000 mg/g) as an antimicrobial agent, BHA (0.200 mg/g) as an antioxidant, EDTA (3.000 mg/g) as a chelating agent, and ethanol (30.000 mg/g).

Example Formulation 28

Formulation 28 comprises phosphatidyl choline (72.299 mg/g) as a lipid, cremophor (97.701 mg/g) as a surfactant, lactate (pH 5) buffer, thimerosal (5.000 mg/g) as an antimicrobial agent, BHA (0.200 mg/g) as an antioxidant, EDTA (3.000 mg/g) as a chelating agent, and ethanol (15.000 mg/g).

Example Formulation 29

Formulation 29 comprises phosphatidyl ethanolamine (46.250 mg/g) as a lipid, Tween 80 (46.250 mg/g) as a surfactant, phosphate (pH 6.5) buffer, thimerosal (5.000 mg/g) as an antimicrobial agent, BHT (0.200 mg/g) and sodium metabisulfite (0.500 mg/g) as an antioxidant, EDTA (3.000 mg/g) as a chelating agent, and ethanol (20.000 mg/g).

Example Formulation 30

Formulation 30 comprises phosphatidyl ethanolamine (38.804 mg/g) as a lipid, Tween 80 (46.196 mg/g) as a surfactant, phosphate (pH 6.5) buffer, thimerosal (5.000 mg/g) as an antimicrobial agent, BHT (0.200 mg/g) and sodium metabisulfite (0.500 mg/g) as an antioxidant, glycerol (15.000 mg/g), EDTA (3.000 mg/g) as a chelating agent, and ethanol (30.000 mg/g).

Example Formulation 31

Formulation 31 comprises phosphatidyl ethanolamine (36.667 mg/g) as a lipid, Brij 98 and Tween 80 (33.333 mg/g) as a surfactant, phosphate (pH 6.5) buffer, thimerosal (5.000 mg/g) as an antimicrobial agent, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 32

Formulation 32 comprises phosphatidyl glycerol (23.333 mg/g) as a lipid, cremophor and Brij 98 (66.667 mg/g) as a surfactant, acetate (pH 4) buffer, benzyl alcohol or paraben (5.000 mg/g) as an antimicrobial agent, BHT (0.200 mg/g) as an antioxidant, and EDTA (3.000 mg/g) as a chelating agent.

Example Formulation 33

Formulation 33 comprises phosphatidyl glycerol (45.833 mg/g) as a lipid, Brij 98 (41.667 mg/g) as a surfactant, acetate (pH 4) buffer, benzyl alcohol or paraben (5.000 mg/g) as an antimicrobial agent, BHT (0.200 mg/g) as an antioxidant, glycerol (30.000 mg/g), and EDTA (3.000 mg/g) as a chelating agent.

Example Formulation 34

Formulation 34 comprises phosphatidyl glycerol (31.957 mg/g) as a lipid, Brij 98 (38.043 mg/g) as a surfactant, acetate (pH 4) buffer, benzyl alcohol or paraben (5.000 mg/g) as as antimicrobial agent, BHT (0.200 mg/g) as an antioxidant, EDTA (3.000 mg/g) as a chelating agent, and ethanol (30.000 mg/g).

Example Formulation 35

Formulation 35 comprises phosphatidyl glycerol (47.143 mg/g) as a lipid, Brij 98 (42.857 mg/g) as a surfactant, acetate (pH 5) buffer, benzyl alcohol or paraben (5.000 mg/g) as an antimicrobial agent, BHT (0.200 mg/g) as an antioxidant, glycerol (30.000 mg/g), EDTA (1.000 mg/g) as a chelating agent, and ethanol (25.000 mg/g).

Example Formulation 36

Formulation 36 comprises phosphatidyl glycerol (96.905 mg/g) as a lipid, Brij 98 (88.095 mg/g) as a surfactant, acetate (pH 5) buffer, benzyl alcohol or paraben (5.000 mg/g) as an antimicrobial agent, BHT (0.200 mg/g) as an antioxidant, glycerol (30.000 mg/g), EDTA (3.000 mg/g) as a chelating agent, and ethanol (20.000 mg/g).

Example Formulation 37

Formulation 37 comprises phosphatidyl glycerol (31.957 mg/g) as a lipid, Brij 98 (38.043) as a surfactant, acetate (pH 5) buffer, benzyl alcohol or paraben (5.000 mg/g) as an antimicrobial agent, BHT (0.200 mg/g) as an antioxidant, EDTA (3.000 mg/g) as a chelating agent, and ethanol (30.000 mg/g).

Example Formulation 38

Formulation 38 comprises phosphatidyl ethanolamine (35.455 mg/g) as a lipid, cremophor (54.545 mg/g) as a surfactant, phosphate (pH 6.5) buffer, benzyl alcohol or paraben (5.000 mg/g) as an antimicrobial agent, BHT (0.200 mg/g) and sodium metabisulfite (0.500 mg/g) as antioxidants, glycerol (30.000 mg/g), and EDTA (3.000 mg/g) as a chelating agent.

Example Formulation 39

Formulation 39 comprises phosphatidyl ethanolamine (84.457 mg/g) as a lipid, cremophor (100.543 mg/g) as a surfactant, phosphate (pH 6.5) buffer, benzyl alcohol or paraben (5.000 mg/g) as an antimicrobial agent, BHT (0.200 mg/g) and sodium metabisulfite (0.500 mg/g) as antioxidants, EDTA (3.000 mg/g) as a chelating agent, and ethanol (30.000 mg/g).

Example Formulation 40

Formulation 40 comprises phosphatidyl ethanolamine (89.048 mg/g) as a lipid, cremophor (80.952 mg/g) as a surfactant, phosphate (pH 6.5) buffer, benzyl alcohol or paraben (5.000 mg/g), BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 41

Formulation 41 comprises phosphatidyl glycerol (41.087 mg/g) as a lipid, Tween 80 (48.913 mg/g) as a surfactant, propionate (pH 4) buffer, benzyl alcohol or paraben (5.000 mg/g) as an antimicrobial agent, BHT (0.200 mg/g) and sodium metabisulfite (0.500 mg/g) as antioxidants, glycerol (30.000 mg/g), EDTA (3.000 mg/g) as a chelating agent, and ethanol (36.510 mg/g).

Example Formulation 42

Formulation 42 comprises phosphatidyl glycerol (45.280 mg/g) as a lipid, Tween 80 (39.720 mg/g) as a surfactant, propionate (pH 4) buffer, benzyl alcohol or paraben (5.000 mg/g) as an antimicrobial agent, BHT (0.200 mg/g) and sodium metabisulfite (0.500 mg/g), and EDTA (3.000 mg/g) as a chelating agent.

Example Formulation 43

Formulation 43 comprises phosphatidyl glycerol (107.500 mg/g) as a lipid, Tween 80 (62.500 mg/g) as a surfactant, propionate (pH 4) buffer, benzyl alcohol or paraben (5.000 mg/g) as an antimicrobial agent, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 44

Formulation 44 comprises phosphatidyl glycerol (77.243 mg/g) as a lipid, Tween 80 (67.757 mg/g) as a surfactant, propionate (pH 4) buffer, benzyl alcohol or paraben (5.000 mg/g) as an antimicrobial agent, BHT (0.200 mg/g) and sodium metabisulfite (0.500 mg/g) as antioxidants, EDTA (3.000 mg/g) as a chelating agent, and ethanol (30.000 mg/g).

Example Formulation 45

Formulation 45 comprises phosphatidyl glycerol (45.280 mg/g) as a lipid, Tween 80 (39.720 mg/g) as a surfactant, propionate (pH 5) buffer, benzyl alcohol or paraben (5.000 mg/g) as an antimicrobial agent, BHT (0.200 mg/g) and sodium metabisulfite (0.500 mg/g) as antioxidants, EDTA (3.000 mg/g) as a chelating agent, and ethanol (30.000 mg/g).

Example Formulation 46

Formulation 46 comprises phosphatidyl glycerol (90.561 mg/g) as a lipid, Tween 80 (79.439 mg/g) as a surfactant, propionate (pH 5) buffer, benzyl alcohol or paraben (5.000 mg/g) as an antimicrobial agent, BHT (0.200 mg/g) and sodium metabisulfite (0.500 mg/g) as antioxidants, EDTA (3.000 mg/g) as a chelating agent, and ethanol (30.000 mg/g).

Example Formulation 47

Formulation 47 comprises phosphatidyl glycerol (47.944 mg/g) as a lipid, Tween 80 (42.056 mg/g) as a surfactant, propionate (pH 5) buffer, benzyl alcohol or paraben (5.000 mg/g) as an antimicrobial agent, BHT (0.200 mg/g) and sodium metabisulfite (0.500 mg/g) as antioxidants, EDTA (3.000 mg/g) as a chelating agent, and ethanol (10.000 mg/g).

Example Formulation 48

Formulation 48 comprises phosphatidyl serine (50.607 mg/g) as a lipid, Brij 98 (44.393 mg/g) as a surfactant, phosphate (pH 5.5) buffer, thimerasol (5.000 mg/g) as an antimicrobial agent, BHT (0.200 mg/g) and sodium metabisulfite (0.500 mg/g) as antioxidants, glycerol (30.000 mg/g), and EDTA (1.000 mg/g) as a chelating agent.

Example Formulation 49

Formulation 49 comprises phosphatidyl serine (107.500 mg/g) as a lipid, Brij 98 (62.500 mg/g) as a surfactant, phosphate (pH 5.5) buffer, thimerasol (5.000 mg/g) as an antimicrobial agent, BHT (0.200 mg/g) and sodium metabisulfite (0.500 mg/g) as antioxidants, glycerol (30.000 mg/g), and EDTA (3.000 mg/g) as a chelating agent.

Example Formulation 50

Formulation 50 comprises phosphatidyl serine (47.944 mg/g) as a lipid, Brij 98 (42.056 mg/g) as a surfactant, phosphate (pH 5.5) buffer, thimerasol (5.000 mg/g) as an antimicrobial agent, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 51

Formulation 51 comprises phosphatidyl glycerol (46.364 mg/g) as a lipid, Brij 98 (38.636 mg/g) as a surfactant, acetate (pH 4) buffer, benzyl alcohol or paraben (5.000 mg/g) as an antimicrobial, BHT (0.200 mg/g) as an antioxidant, glycerol (30.000 mg/g), EDTA (3.000 mg/g) as a chelating agent, and ethanol (25.000 mg/g).

Example Formulation 52

Formulation 52 comprises phosphatidyl glycerol (46.364 mg/g) as a lipid, Brij 98 (38.636 mg/g) as a surfactant, acetate (pH 4) buffer, benzyl alcohol or paraben (5.000 mg/g) as an antimicrobial, BHT (0.200 mg/g) as an antioxidant, EDTA (3.000 mg/g) as a chelating agent, and ethanol (20.000 mg/g).

Example Formulation 53

Formulation 53 comprises phosphatidyl glycerol (46.098 mg/g) as a lipid, Brij 98 (43.902 mg/g) as a surfactant, acetate (pH 5) buffer, benzyl alcohol or paraben (5.000 mg/g) as an antimicrobial, BHT (0.200 mg/g) as an antioxidant, glycerol (15.000 mg/g), EDTA (3.000 mg/g) as a chelating agent, and ethanol (30.000 mg/g).

Example Formulation 54

Formulation 54 comprises phosphatidyl glycerol (43.537 mg/g) as a lipid, Brij 98 (41.463 mg/g) as a surfactant, acetate (pH 5) buffer, benzyl alcohol or paraben (5.000 mg/g) as an antimicrobial, BHT (0.200 mg/g) as an antioxidant, glycerol (30.000 mg/g), and EDTA (3.000 mg/g) as a chelating agent.

Example Formulation 55

Formulation 55 comprises phosphatidyl glycerol (45.000 mg/g) as a lipid, Brij 98 (45.000 mg/g) as a surfactant, acetate (pH 5) buffer, benzyl alcohol or paraben (5.000 mg/g) as an antimicrobial, BHT (0.200 mg/g) as an antioxidant, EDTA (3.000 mg/g) as a chelating agent, and ethanol (30.000 mg/g).

Example Formulation 56

Formulation 56 comprises phosphatidyl glycerol (59.492 mg/g) as a lipid, Brij 98 (30.508 mg/g) as a surfactant, acetate (pH 6.5) buffer, benzyl alcohol or paraben (5.000 mg/g) as an antimicrobial, BHT (0.200 mg/g) as an antioxidant, glycerol (30.000 mg/g), EDTA (3.000 mg/g) as a chelating agent, and ethanol (30.000 mg/g).

Example Formulation 57

Formulation 57 comprises phosphatidyl glycerol (39.054 mg/g) as a lipid, Brij 98 (45.946 mg/g) as a surfactant, acetate (pH 6.5) buffer, benzyl alcohol or paraben (5.000 mg/g) as an antimicrobial, BHT (0.200 mg/g) as an antioxidant, and EDTA (3.000 mg/g) as a chelating agent.

Example Formulation 58

Formulation 58 comprises phosphatidyl glycerol (35.854 mg/g) as a lipid, Brij 98 (34.146 mg/g) as a surfactant, acetate (pH 6.5) buffer, benzyl alcohol or paraben (5.000 mg/g) as an antimicrobial, BHT (0.200 mg/g) as an antioxidant, glycerol (30.000 mg/g), and EDTA (3.000 mg/g) as a chelating agent.

Example Formulation 59

Formulation 59 comprises phosphatidyl choline (50.000 mg/g) as a lipid, Tween 80 (40.000 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 60

Formulation 60 comprises phosphatidyl choline (38.571 mg/g) as a lipid, Tween 80 (51.429 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g), and ethanol (30.000 mg/g).

Example Formulation 61

Formulation 61 comprises phosphatidyl choline (41.954 mg/g) as phospholipid, Tween 80 (50.546 mg/g) as surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g), and ethanol (30.000 mg/g).

Example Formulation 62

Formulation 62 comprises phosphatidyl choline (42.632 mg/g) as a lipid, Tween 80 (47.368 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 63

Formulation 63 comprises phosphatidyl choline (46.098 mg/g) as a lipid, Tween 80 (43.902 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 64

Formulation 64 comprises phosphatidyl choline (39.721 mg/g) as a lipid, Tween 80 (50.279 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 65

Formulation 65 comprises phosphatidyl choline (44.198 mg/g) as a lipid, Tween 80 (50.802 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 66

Formulation 66 comprises phosphatidyl choline (46.453 mg/g) as a lipid, Tween 80 (51.047 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 67

Formulation 67 comprises phosphatidyl choline (51.221 mg/g) as a lipid, Tween 80 (43.779 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 68

Formulation 68 comprises phosphatidyl choline (54.167 mg/g) as a lipid, Tween 80 (43.333 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 69

Formulation 69 comprises phosphatidyl choline (66.440 mg/g) as a lipid, Brij 98 (23.560 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g). Example formulation 69 is an emulsion.

Example Formulation 70

Formulation 70 comprises phosphatidyl choline (66.440 mg/g) as a lipid, Brij 98 (23.560 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g). Example formulation 70 is a suspension.

Example Formulation 71

Formulation 71 comprises phosphatidyl choline (66.440 mg/g) as a lipid, Brij 98 (23.560 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 72

Formulation 72 comprises phosphatidyl choline (40.000 mg/g) as a lipid, Tween 80 (50.000 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g). Example formulation 72 is an emulsion.

Example Formulation 73

Formulation 73 comprises phosphatidyl choline (40.000 mg/g) as a lipid, Tween 80 (50.000 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g). Example formulation 73 is a suspension.

Example Formulation 74

Formulation 74 comprises phosphatidyl choline (40.000 mg/g) as a lipid, Tween 80 (50.000 mg/g) as a surfactant, acetate (pH 5.5) buffer, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 75

Formulation 75 comprises phosphatidyl choline (40.000 mg/g) as a lipid, Tween 80 (50.000 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 76

Formulation 76 comprises phosphatidyl choline (40.000 mg/g) as a lipid, Brij 98 (50.000 mg/g) as a surfactant, phosphate (pH 6.5) buffer, benzalkonium chloride (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 77

Formulation 77 comprises phosphatidyl choline (40.000 mg/g) as a lipid, Tween 80 (50.000 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 78

Formulation 78 comprises phosphatidyl choline (66.440 mg/g) as a lipid, Brij 98 (23.560 mg/g) as a surfactant, phosphate (pH 6.5) buffer, benzalkonium chloride (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 79

Formulation 79 comprises phosphatidyl choline (66.440 mg/g) as a lipid, Brij 98 (23.560 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 80

Formulation 80 comprises phosphatidyl choline (40.000 mg/g) as a lipid, Tween 80 (50.000 mg/g) as a surfactant, acetate (pH 5.5) buffer, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 81

Formulation 81 comprises phosphatidyl choline (40.000 mg/g) as a lipid, Tween 80 (50.000 mg/g) as a surfactant, acetate (pH 5.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 82

Formulation 82 comprises phosphatidyl choline (44.444 mg/g) as a lipid, Tween 80 (55.556 mg/g) as a surfactant, acetate (pH 5.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 83

Formulation 83 comprises phosphatidyl choline (66.440 mg/g) as a lipid, Tween 80 (23.560 mg/g) as a surfactant, acetate (pH 5.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 84

Formulation 84 comprises phosphatidyl choline (54.000 mg/g) as a lipid, Tween 80 (36.000 mg/g) as a surfactant, acetate (pH 4) buffer, benzyl alcohol or paraben (5.000 mg/g) as an antimicrobial, BHA (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 85

Formulation 85 comprises phosphatidyl choline (50.000 mg/g) as a lipid, Tween 80 (40.000 mg/g) as a surfactant, acetate (pH 4) buffer, benzyl alcohol or paraben (5.000 mg/g) as an antimicrobial, BHA (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 86

Formulation 86 comprises phosphatidyl choline (48.611 mg/g) as a lipid, Tween 80 (38.889 mg/g) as a surfactant, acetate (pH 4) buffer, benzyl alcohol or paraben (5.000 mg/g) as an antimicrobial, BHA (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 87

Formulation 87 comprises phosphatidyl choline (46.575 mg/g) as a lipid, Tween 80 (38.425 mg/g) as a surfactant, acetate (pH 4) buffer, benzyl alcohol or paraben (5.000 mg/g) as an antimicrobial, BHA (0.200 mg/g) and sodium metabisulfite (0.500 mg/g) as antioxidants, glycerol (30.000 mg/g), EDTA (3.000 mg/g) as a chelating agent, and ethanol (30.000 mg/g). Example formulation 87 is an emulsion.

Example Formulation 88

Formulation 88 comprises phosphatidyl choline (46.575 mg/g) as a lipid, Tween 80 (38.425 mg/g) as a surfactant, acetate (pH 4) buffer, benzyl alcohol or paraben (5.000 mg/g) as an antimicrobial, BHA (0.200 mg/g) and sodium metabisulfite (0.500 mg/g) as antioxidants, glycerol (30.000 mg/g), EDTA (3.000 mg/g) as a chelating agent, and ethanol (30.000 mg/g). Example formulation 88 is suspension.

Example Formulation 89

Formulation 89 comprises phosphatidyl choline (46.575 mg/g) as a lipid, Tween 80 (38.425 mg/g) as a surfactant, acetate (pH 4) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 90

Formulation 90 comprises phosphatidyl choline (50.000 mg/g) as a lipid, Tween 80 (40.000 mg/g) as a surfactant, acetate (pH 4.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 91

Formulation 91 comprises phosphatidyl choline (94.444 mg/g) as a lipid, Tween 80 (75.556 mg/g) as a surfactant, acetate (pH 4) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 92

Formulation 92 comprises phosphatidyl choline (46.712 mg/g) as a lipid, Tween 80 (38.288 mg/g) as a surfactant, acetate (pH 4) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 93

Formulation 93 comprises phosphatidyl choline (48.889 mg/g) as a lipid, Tween 80 (39.111 mg/g) as a surfactant, acetate (pH 4) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 94

Formulation 94 comprises phosphatidyl choline (39.721 mg/g) as a lipid, Tween 80 (50.279 mg/g) as a surfactant, phosphate (pH 6.5) buffer, benzyl alcohol or paraben (5.25 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 95

Formulation 95 comprises phosphatidyl choline (90.000 mg/g) as a lipid, phosphate buffer (pH 6.5), benzyl alcohol or paraben as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 96

Formulation 96 comprises phosphatidyl choline (68.700 mg/g) as a lipid, Tween 80 (8.500 mg/g) as a surfactant, phosphate (pH 7.5) buffer, BHT (0.200 mg/g) and sodium metabisulfite (0.500 mg/g) as antioxidants, benzyl alcohol or paraben (5.000 mg/g) as an antimicrobial, glycerol (30.000 mg/g), EDTA (1.000 mg/g) as a chelating agent, and ethanol (36.51 mg/g).

Example Formulation 97

Formulation 97 comprises phosphatidyl choline (71.460 mg/g) as a lipid, Tween 80 (4.720 mg/g) as a surfactant, phosphate (pH 7.5) buffer, BHA (0.200 mg/g) and sodium metabisulfite (0.500 mg/g) as antioxidants, benzyl alcohol or paraben (5.000 mg/g) as an antimicrobial, glycerol (50.000 mg/g), EDTA (3.000 mg/g) as a chelating agent, and ethanol (35.000 mg/g).

Example Formulation 98

Formulation 98 comprises phosphatidyl choline (71.460 mg/g) as a lipid, Tween 80 (4.720 mg/g) as a surfactant, phosphate (pH 7.8) buffer, BHA (0.200 mg/g) and sodium metabisulfite (0.500 mg/g) as antioxidants, benzyl alcohol or paraben (5.000 mg/g) as an antimicrobial, glycerol (15.000 mg/g), EDTA (3.000 mg/g) as a chelating agent, and ethanol (35.000 mg/g).

Example Formulation 99

Formulation 99 comprises phosphatidyl choline (71.460 mg/g) as a lipid, Tween 80 (4.720 mg/g) as a surfactant, phosphate (pH 7.8) buffer, BHA (0.200 mg/g) and sodium metabisulfite (0.500 mg/g) as antioxidants, glycerol (50.000 mg/g), EDTA (3.000 mg/g) as a chelating agent, and ethanol (15.000 mg/g).

Example Formulation 100

Formulation 100 comprises phosphatidyl choline (71.4600 mg/g) as a lipid, Tween 80 (4.720 mg/g) as a surfactant, phosphate (pH 7.5) buffer, BHA (0.200 mg/g) and sodium metabisulfite (0.500 mg/g) as antioxidants, glycerol (50.000 mg/g), EDTA (3.000 mg/g) as a chelating agent, and ethanol (35.000 mg/g).

Example Formulation 101

Formulation 101 comprises phosphatidyl choline (46.575 mg/g) as a lipid, Tween 80 (38.425 mg/g) as a surfactant, phosphate (pH 4) buffer, BHT (0.500 mg/g) and sodium metabisulfite (0.200 mg/g) as antioxidants, and EDTA (3.000 mg/g) as a chelating agent. Example formulation 101 is an emulsion.

Example Formulation 102

Formulation 102 comprises phosphatidyl choline (46.575 mg/g) as a lipid, Tween 80 (38.425 mg/g) as a surfactant, phosphate (pH 4) buffer, BHT (0.500 mg/g) and sodium metabisulfite (0.200 mg/g) as antioxidants, and EDTA (3.000 mg/g). Example formulation 102 is a suspension.

Example Formulation 103

Formulation 103 comprises phosphatidyl choline (54.643 mg/g) as a lipid, Tween 80 (30.357 mg/g) as a surfactant, phosphate (pH 4) buffer, BHA (0.500 mg/g) and sodium metabisulfite (0.200 mg/g) as antioxidants, and EDTA (3.000 mg/g) as a chelating agent.

Example Formulation 104

Formulation 104 comprises phosphatidyl choline (39.72 mg/g) as a lipid, Tween 80 (50.279 mg/g) as surfactant, phosphate (pH 6.5) buffer, benzyl alcohol or paraben (5.00 mg/g) as an antimicrobial, BHT (0.200 mg/g) and sodium metabisulfite (0.500 mg/g) as antioxidants, glycerol (30.000 mg/g) as emollient, EDTA (3.000 mg/g) as the chelating agent, and ethanol (30.000 mg/g).

Example Formulation 105

Formulation 105 comprises phosphatidyl choline (90.00 mg/g) as a lipid, phosphate (pH 6.5) buffer, benzyl alcohol or paraben as antimicrobial (5.000 mg/s), BHT (0.200 mg/g) and sodium metabisulfite (0.500 mg/g) as antioxidants, glycerol (30.000 mg/g) as emollient, EDTA (3.000 mg/g) as the chelating agent, and ethanol (30.000 mg/g).

Example Formulation 106

Formulation 106 comprises phosphatidyl choline (46.57 mg/g) as a lipid, Tween 80 (38.425 mg/g) as a surfactant, phosphate (pH 4) buffer, BHT (0.500 mg/g) and sodium metabisulfite (0.200 mg/g) as antioxidants, and EDTA (3.000 mg/g) as the chelating agent. Formulation 106 is formulated as an emulsion.

Example Formulation 107

Formulation 107 comprises phosphatidyl choline (46.57 mg/g) as a lipid, Tween 80 (38.425 mg/g) as a surfactant, phosphate (pH 4) buffer, BHT (0.500 mg/g) and sodium metabisulfite (0.200 mg/g) as antioxidants, and EDTA (3.000 mg/g) as the chelating agent. Formulation 107 as a suspension.

Example Formulation 108

Formulation 108 comprises phosphatidyl choline (54.64 mg/g) as a lipid, Tween 80 (30.357 mg/g) as a surfactant, phosphate (pH 4) buffer, BHA (0.500 mg/g) and sodium metabisulfite (0.200 mg/g) as antioxidants, EDTA (3.000 mg/g) as the chelating agent.

Example Formulation 109

Formulation 109 comprises phosphatidyl glycerol and lysophospholipid (46.364 mg/g) as a lipid, Brij 98 (38.636 mg/g) as a surfactant, acetate (pH 4) buffer, benzyl alcohol or paraben (5.000 mg/g) as an antimicrobial, BHT (0.200 mg/g) as an antioxidant, glycerol (30.000 mg/g), EDTA (3.000 mg/g) as a chelating agent, and ethanol (25.000 mg/g).

Example Formulation 110

Formulation 110 comprises phosphatidyl glycerol and lysophospholipid (46.364 mg/g) as a lipid, Brij 98 (38.636 mg/g) as a surfactant, acetate (pH 4) buffer, benzyl alcohol or paraben (5.000 mg/g) as an antimicrobial, BHT (0.200 mg/g) as an antioxidant, EDTA (3.000 mg/g) as a chelating agent, and ethanol (20.000 mg/g).

Example Formulation 111

Formulation 111 comprises phosphatidyl glycerol and lysophospholipid (46.098 mg/g) as a lipid, Brij 98 (43.902 mg/g) as a surfactant, acetate (pH 5) buffer, benzyl alcohol or paraben (5.000 mg/g) as an antimicrobial, BHT (0.200 mg/g) as an antioxidant, glycerol (15.000 mg/g), EDTA (3.000 mg/g) as a chelating agent, and ethanol (30.000 mg/g).

Example Formulation 112

Formulation 112 comprises phosphatidyl glycerol and lysophospholipid (43.537 mg/g) as a lipid, Brij 98 (41.463 mg/g) as a surfactant, acetate (pH 5) buffer, benzyl alcohol or paraben (5.000 mg/g) as an antimicrobial, BHT (0.200 mg/g) as an antioxidant, glycerol (30.000 mg/g), and EDTA (3.000 mg/g) as a chelating agent.

Example Formulation 113

Formulation 113 comprises phosphatidyl glycerol and lysophospholipid (45.000 mg/g) as a lipid, Brij 98 (45.000 mg/g) as a surfactant, acetate (pH 5) buffer, benzyl alcohol or paraben (5.000 mg/g) as an antimicrobial, BHT (0.200 mg/g) as an antioxidant, EDTA (3.000 mg/g) as a chelating agent, and ethanol (30.000 mg/g).

Example Formulation 114

Formulation 114 comprises phosphatidyl glycerol and lysophospholipid (59.492 mg/g) as a lipid, Brij 98 (30.508 mg/g) as a surfactant, acetate (pH 6.5) buffer, benzyl alcohol or paraben (5.000 mg/g) as an antimicrobial, BHT (0.200 mg/g) as an antioxidant, glycerol (30.000 mg/g), EDTA (3.000 mg/g) as a chelating agent, and ethanol (30.000 mg/g).

Example Formulation 115

Formulation 115 comprises phosphatidyl glycerol and lysophospholipid (39.054 mg/g) as a lipid, Brij 98 (45.946 mg/g) as a surfactant, acetate (pH 6.5) buffer, benzyl alcohol or paraben (5.000 mg/g) as an antimicrobial, BHT (0.200 mg/g) as an antioxidant, and EDTA (3.000 mg/g) as a chelating agent.

Example Formulation 116

Formulation 116 comprises phosphatidyl glycerol and lysophospholipid (35.854 mg/g) as a lipid, Brij 98 (34.146 mg/g) as a surfactant, acetate (pH 6.5) buffer, benzyl alcohol or paraben (5.000 mg/g) as an antimicrobial, BHT (0.200 mg/g) as an antioxidant, glycerol (30.000 mg/g), and EDTA (3.000 mg/g) as a chelating agent.

Example Formulation 117

Formulation 117 comprises phosphatidyl choline and lysophospholipid (50.000 mg/g) as a lipid, Tween 80 (40.000 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 118

Formulation 118 comprises phosphatidyl choline and lysophospholipid (38.571 mg/g) as a lipid, Tween 80 (51.429 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g), and ethanol (30.000 mg/g).

Example Formulation 119

Formulation 119 comprises phosphatidyl choline and lysophospholipid (41.954 mg/g) as phospholipid, Tween 80 (50.546 mg/g) as surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g), and ethanol (30.000 mg/g).

Example Formulation 120

Formulation 120 comprises phosphatidyl choline and lysophospholipid (42.632 mg/g) as a lipid, Tween 80 (47.368 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 121

Formulation 121 comprises phosphatidyl choline and lysophospholipid (46.098 mg/g) as a lipid, Tween 80 (43.902 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 122

Formulation 122 comprises phosphatidyl choline and lysophospholipid (39.721 mg/g) as a lipid, Tween 80 (50.279 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 123

Formulation 123 comprises phosphatidyl choline and lysophospholipid (44.198 mg/g) as a lipid, Tween 80 (50.802 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 124

Formulation 124 comprises phosphatidyl choline and lysophospholipid (46.453 mg/g) as a lipid, Tween 80 (51.047 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 125

Formulation 125 comprises phosphatidyl choline and lysophospholipid (51.221 mg/g) as a lipid, Tween 80

(43.779 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 126

Formulation 126 comprises phosphatidyl choline (54.167 mg/g) as a lipid, Tween 80 (43.333 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

Example Formulation 127

Formulation 127 comprises phosphatidyl choline and lysophospholipid (66.440 mg/g) as a lipid, Brij 98 (23.560 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g). Example formulation 69 is an emulsion.

Example Formulation 128

Formulation 128 comprises phosphatidyl choline and lysophospholipid (66.440 mg/g) as a lipid, Brij 98 (23.560 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g). Example formulation 70 is a suspension.

Example Formulation 129

Formulation 129 comprises phosphatidyl choline and lysophospholipid (66.440 mg/g) as a lipid, Brij 98 (23.560 mg/g) as a surfactant, phosphate (pH 6.5) buffer, benzyl alcohol or paraben (5.000 mg/g) as an antimicrobial, BHT (0.200 mg/g) and sodium metabisulfite (0.500 mg/g) as antioxidants, glycerol (30.000 mg/g), EDTA (3.000 mg/g) as a chelating agent, and ethanol (30.000 mg/g).

It will be understood that the exact amounts of the components of the formula may be adjusted slightly without departing from the scope of the invention. For example, in each of the above formulations, the amount antimicrobial be anywhere from about 1 mg/g to about 15 mg/g, or about 5 m/g to about 12 mg/g, or 5.25 mg/g, 6, mg/6, 7 mg/g, 8 mg/g, 9 mg/g, 10 mg/g, or 10.25 mg/g. Furthermore, the antimicrobial can be a combination of ingredients, for example benzyl alcohol and parabenes (e.g., ethyl and/or propyl).

Example Formulations 1 through 129 may also optionally include thickeners such as pectin, xanthan gum, HPMC gel, methylcellulose or carbopol.

Example 2

DIRACTIN® Clinical Studies

Clinical studies directed to DIRACTIN® (ketoprofen in TRANSFERSOME® gel) were performed in the United States and in Europe. Table 9 provides details of the number of sites patients and the like in the European and US studies.

TABLE 9

Comparative evaluation of various clinical studies conducted

| | Sites | Screen Failures | Random | PP | Discont. | Screen F. Rate | PP per site | Rel. Discont. |
|---|---|---|---|---|---|---|---|---|
| US (-06) | 37 | 329 | 555 | 376/452 | 105 | 59% | 10/12 | 19% |
| EU (-03) | 71 | 192 | 1399 | 1163 | 143 | 14% | 16 | 10% |

United States Study

A multicentre, randomized, double-blind, pacebo-controlled study of safety and efficacy of epicutaneously applied DIRACTIN® (ketoprofen in TRANSFERSOME® gel) was conducted in the United states for the treatment of osteoarthritis of the knee. The study was conducted from Q2/2008 to Q2/2009 and included 555 patients in 37 study centres. Patients were treated twice daily at approximately 12 hour intervals for 12 weeks with either:

(1) 100 mg ketoprofen (KT) in DIRACTIN® gel, epicutaneously (e.c.) or (2) Placebo gel with volume matched with 100 mg KT in DIRACTIN®, e.c.

The DIRACTIN® gel and the placebo gel included transfersomes in accordance with the descriptions provided herein. Rescue pain medication was provided in the amount of 500 mg acetaminophen up to four times a day, total 2 g.

Figure 1B:
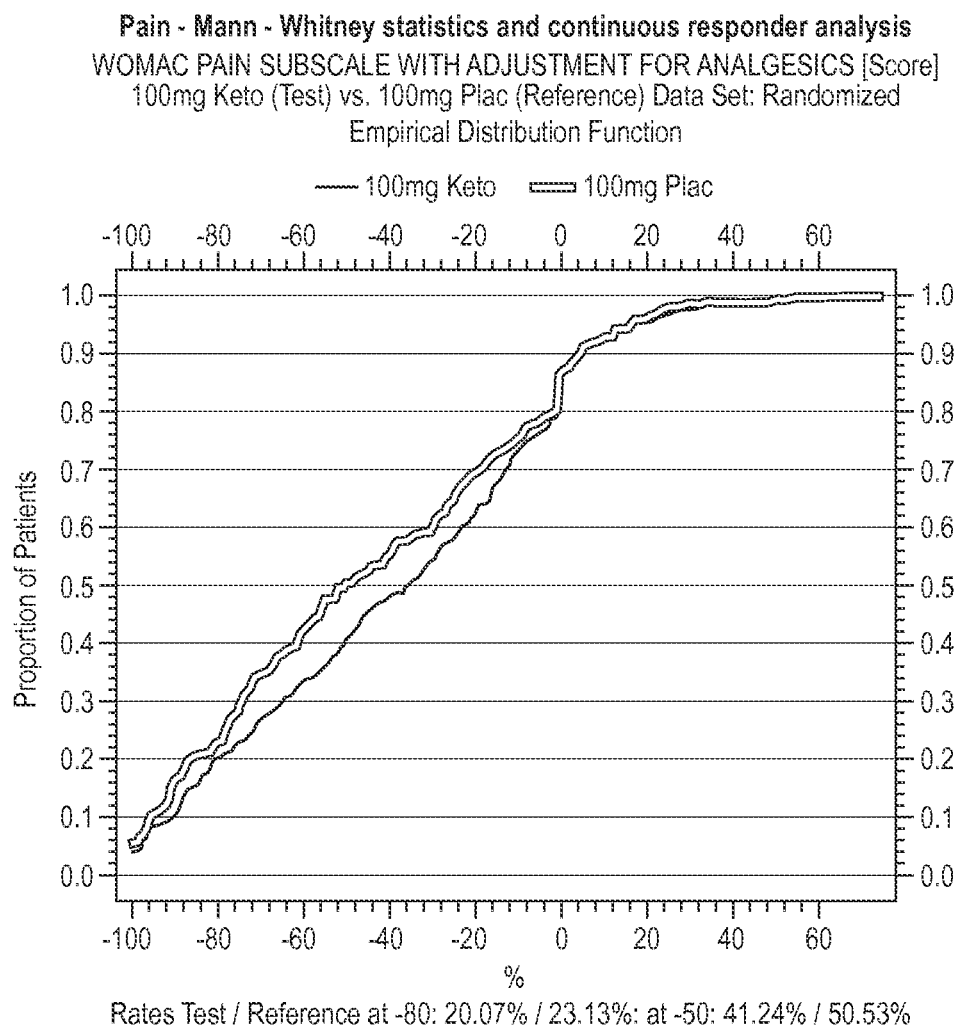
FIG. 1B shows the results of example 2 (United States study) and provides Mann-Whitney statistics and continuous responder analysis of pain measurements in patients, analysed by randomised empirical distribution function.
Figure 3:
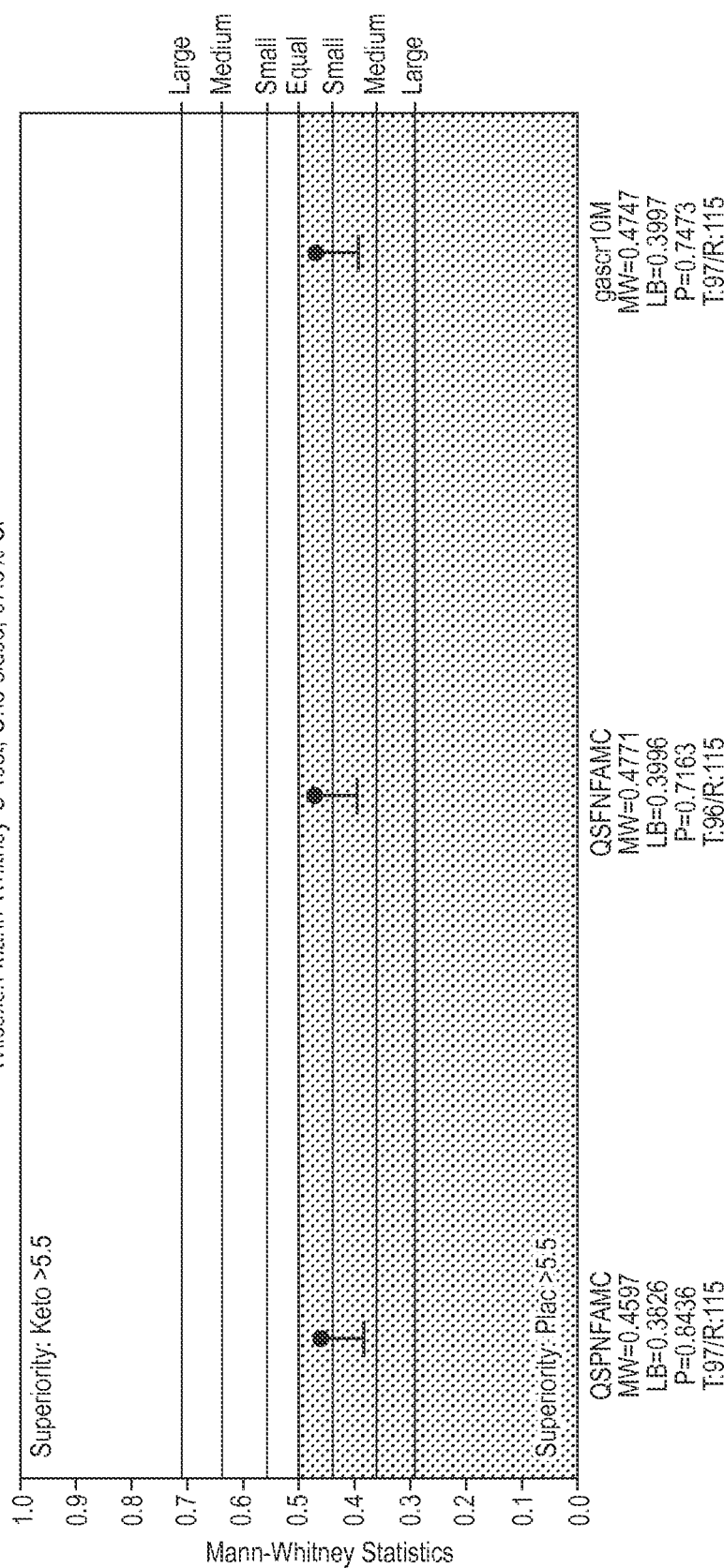
FIG. 3 shows the results of example 2 (United States study) and provides subgroup analysis results for WOMAC pain intensity at a baseline of >5.5.
Figure 4:
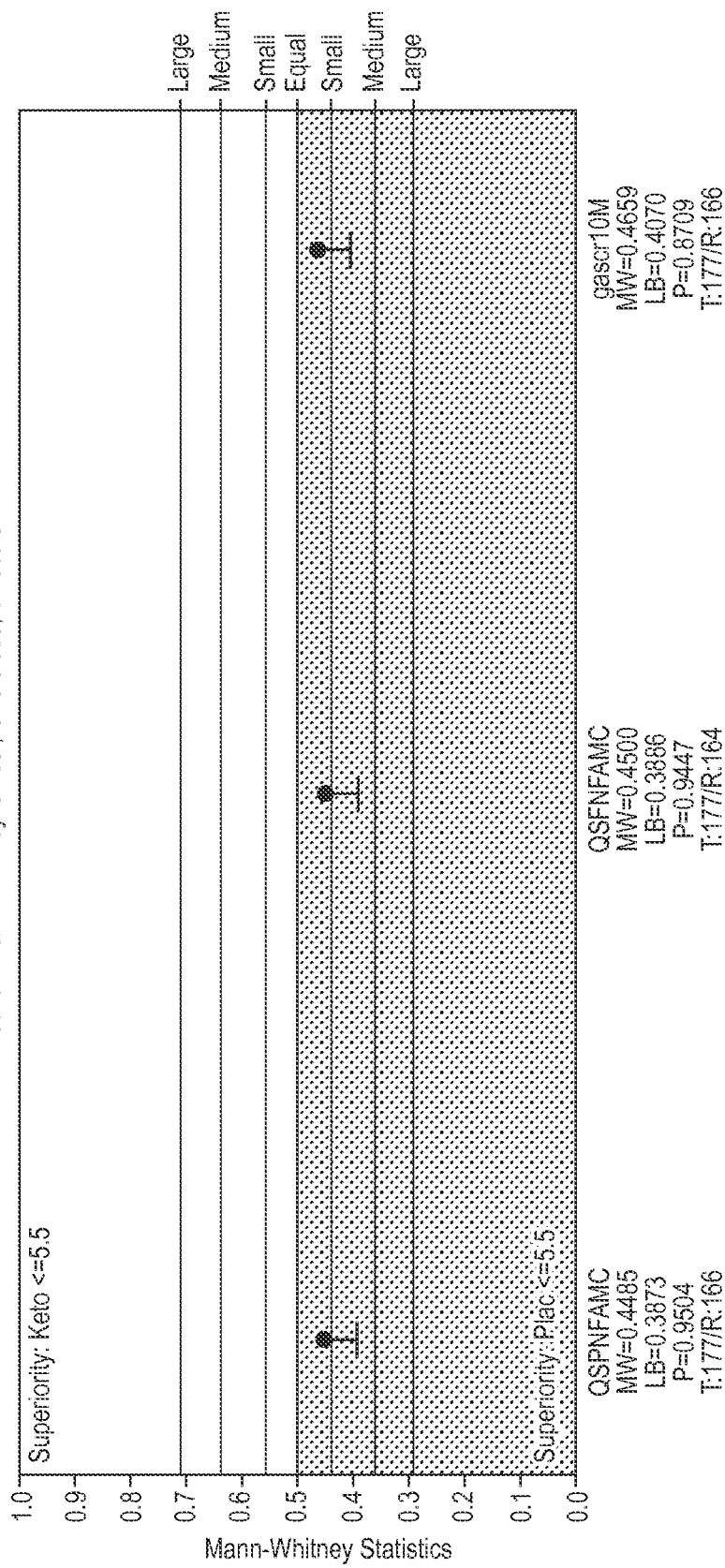
FIG. 4 shows the results of example 2 (United States study) and provides subgroup analysis results for WOMAC pain intensity at a baseline of ≤5.5.

The data from these studies established that the placebo transfersomes (i.e., transfersomes of the technology described herein) were active. Data from the US study are shown in FIGS. 1-5. FIG. 1 shows Mann-Whitney statistics and continuous responder analysis of pain measurements in patients. FIG. 2 provides the incidences of Adverse Events by organ class system. Subgroup analysis results for WOMAC pain intensity are shown in FIGS. 3 and 4; with FIG. 3 at a baseline of >5.5 and Figure for at baseline ≤5.5. Descriptive statistics for the use of rescue medication are provided in FIG. 5.

European Study

A multicentre, randomized, double-blind, placebo-controlled study of safety and efficacy of epicutaneously applied DIRACTIN® (ketoprofen in TRANSFERSOME® gel) was also conducted in Europe for the treatment of osteoarthritis of the knee. The study was conducted from Q2/2008 to Q2/2009 and included 1,399 patients in 71 study centres (in Czech Republic, Germany, Poland, and UK). Patients were treated twice daily at approximately 12 hour intervals for 12 weeks with either:

(1) 50 mg ketoprofen (KT) in DIRACTIN® gel, epicutaneously (e.c.)

(2) Placebo gel with volume matched with 50 mg KT in DIRACTIN®, e.c.

(3) 100 mg ketoprofen (KT) in DIRACTIN® gel, e.c.

(4) Placebo gel with volume matched with 100 mg KT in DIRACTIN®, e.c.

(5) 100 mg celecoxib capsule (CELEBREX®, Pfizer), oral (6) Placebo capsule, matching celecoxib, oral The DIRACTIN® gel and the placebo gel included transfersomes in accordance with the descriptions provided herein. Rescue pain medication was provided in the amount of 500 mg acetaminophen up to four times a day, total 2 g.

Figure 6:
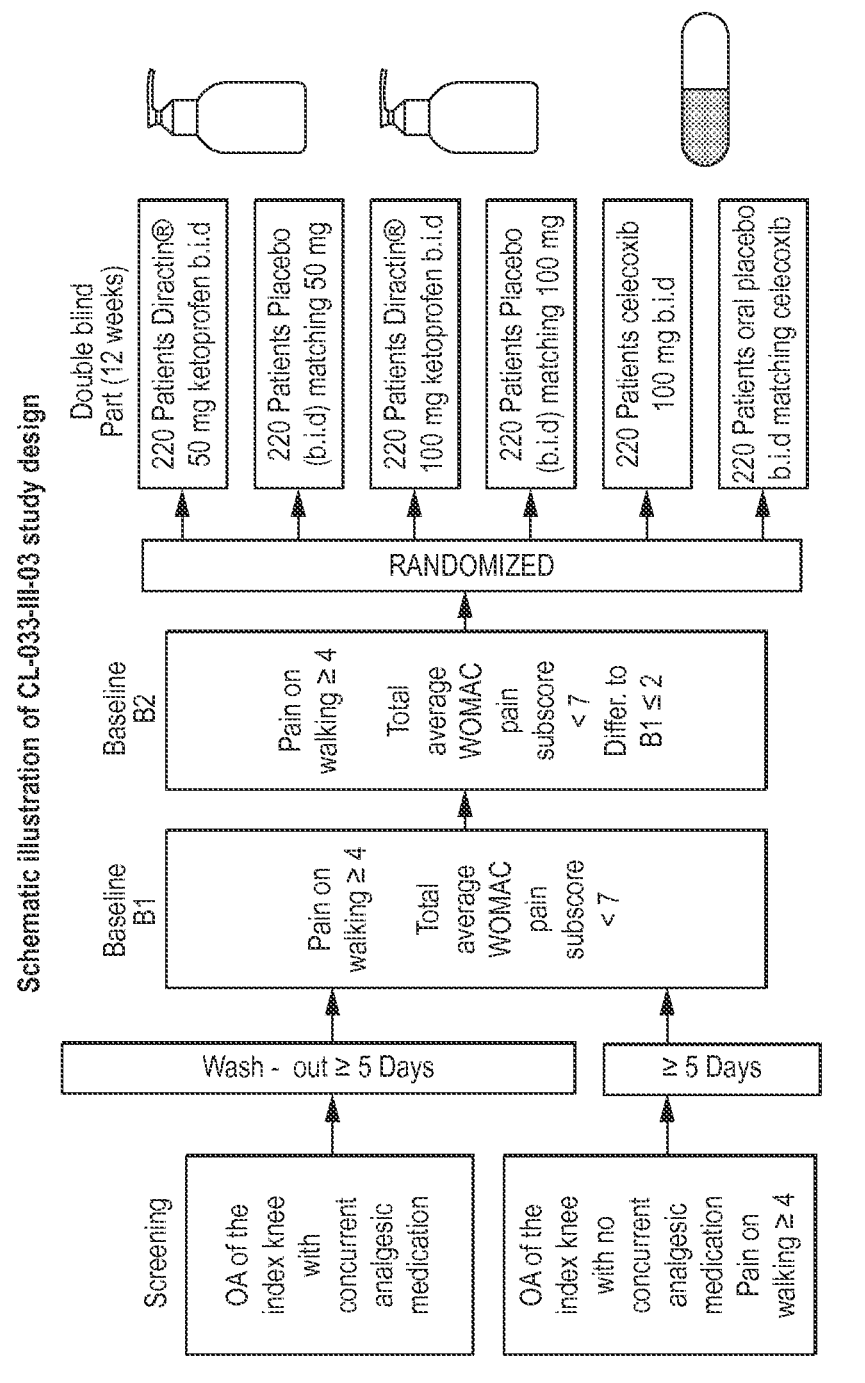
FIG. 6 shows the results of example 2 (European study) and provides a schematic illustrating the study design.
Figure 7:
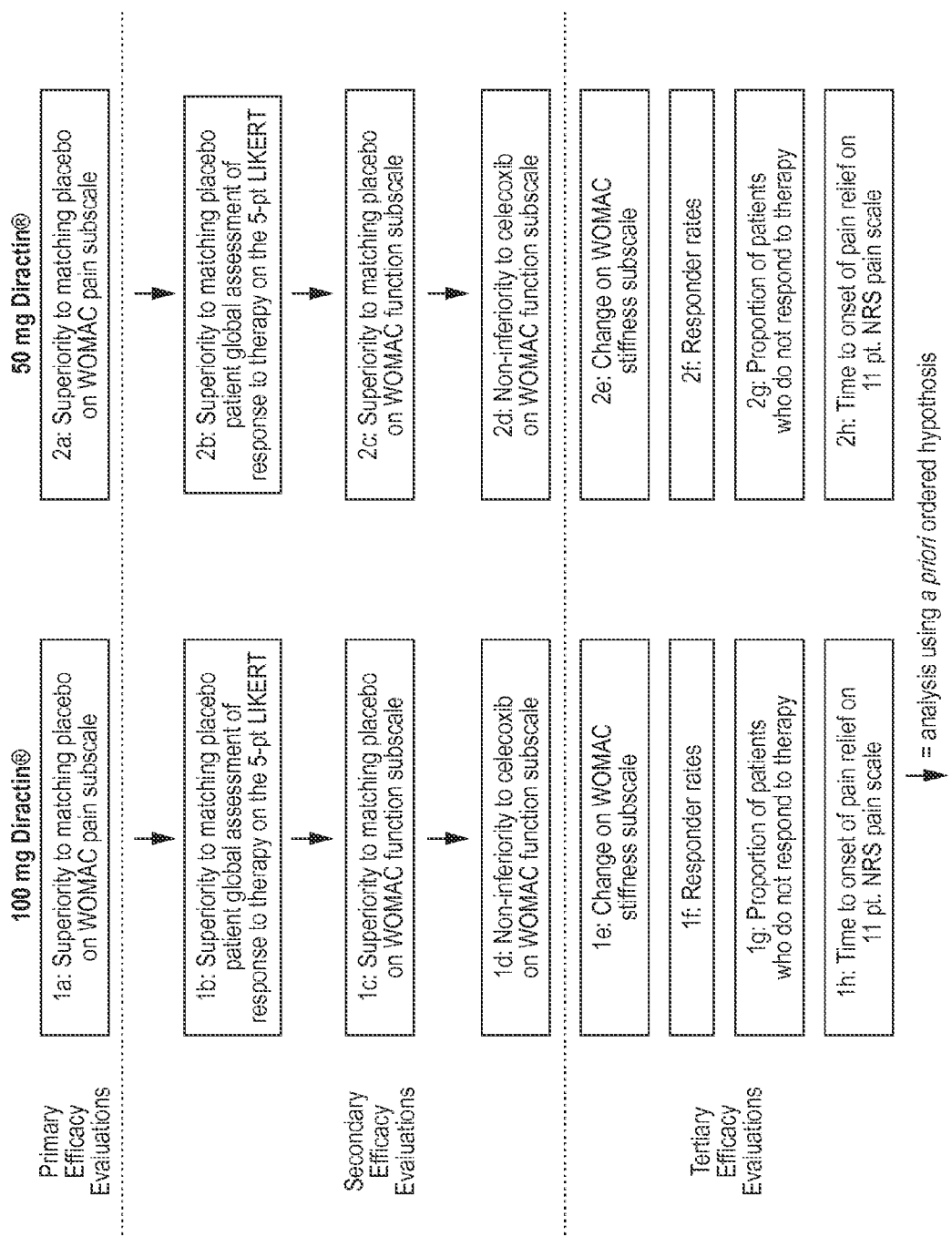
FIG. 7 shows the results of example 2 (European study) and shows the statistical evaluations.

A schematic illustrating the study design is shown on FIG. 6 and an illustration showing the statistical evaluations are shown in FIG. 7.

Figure 8A:
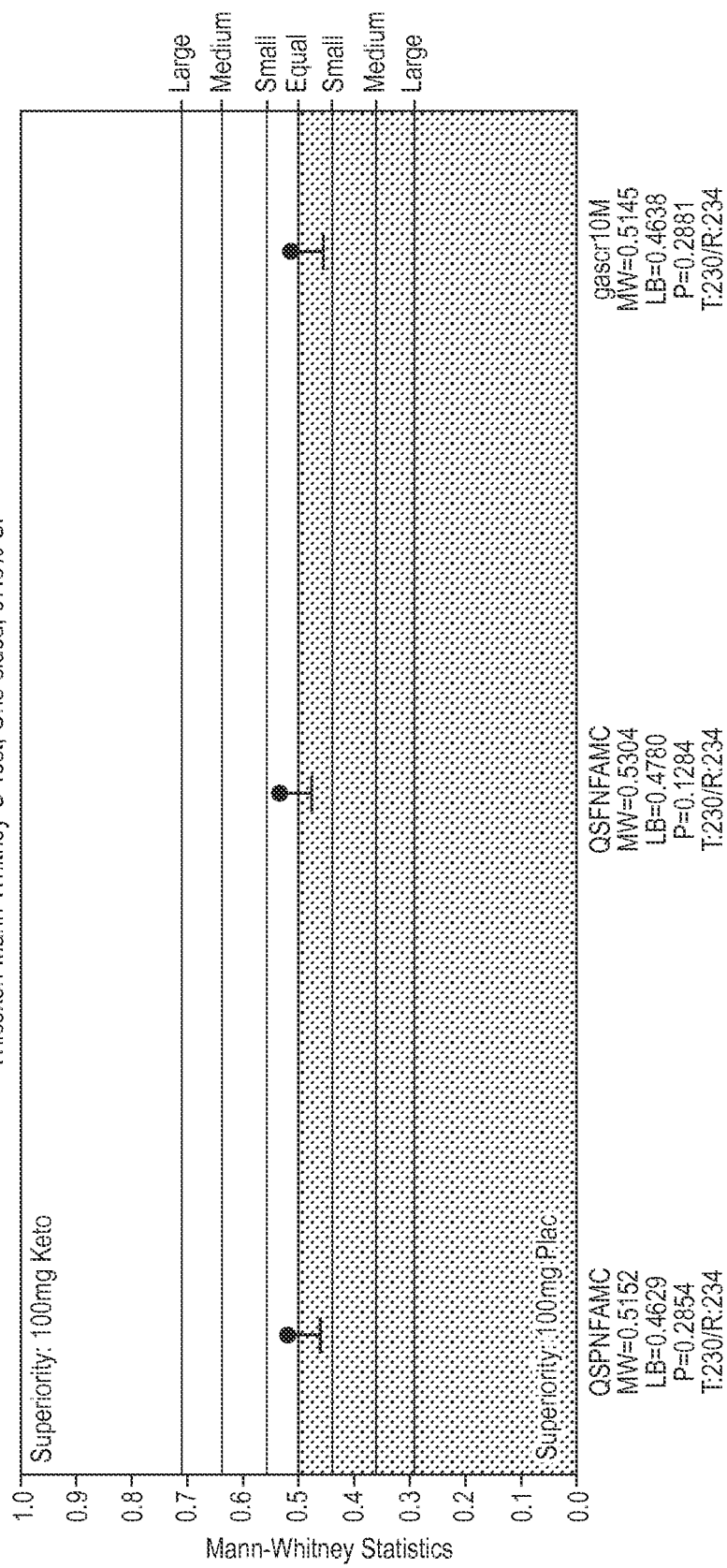
FIG. 8A shows the results of example 2 (European study) and provides Mann-Whitney statistics and continuous responder analysis of pain measurements in patients treated with 100 mg KT and placebo gel, analysed by randomised Wilcoxon-Mann-Whitney-U test.
Figure 8B:
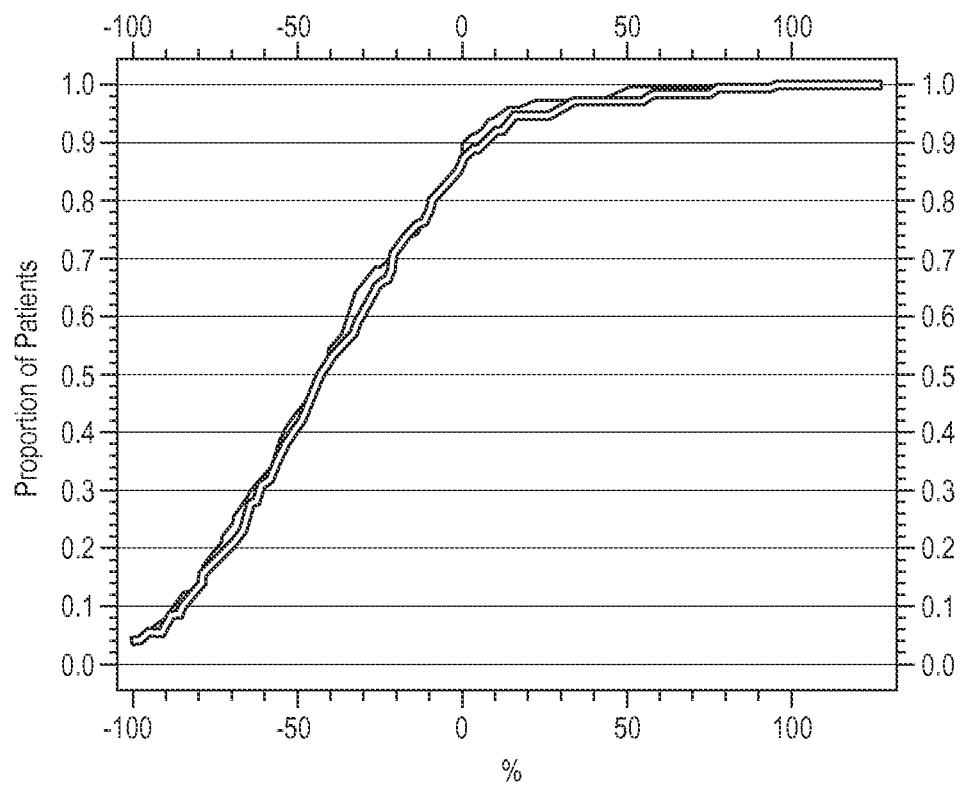
FIG. 8B shows the results of example 2 (European study) and provides Mann-Whitney statistics and continuous responder analysis of pain measurements in patients treated with 100 mg KT and placebo gel, analysed by randomised empirical distribution function.
Figure 9A:
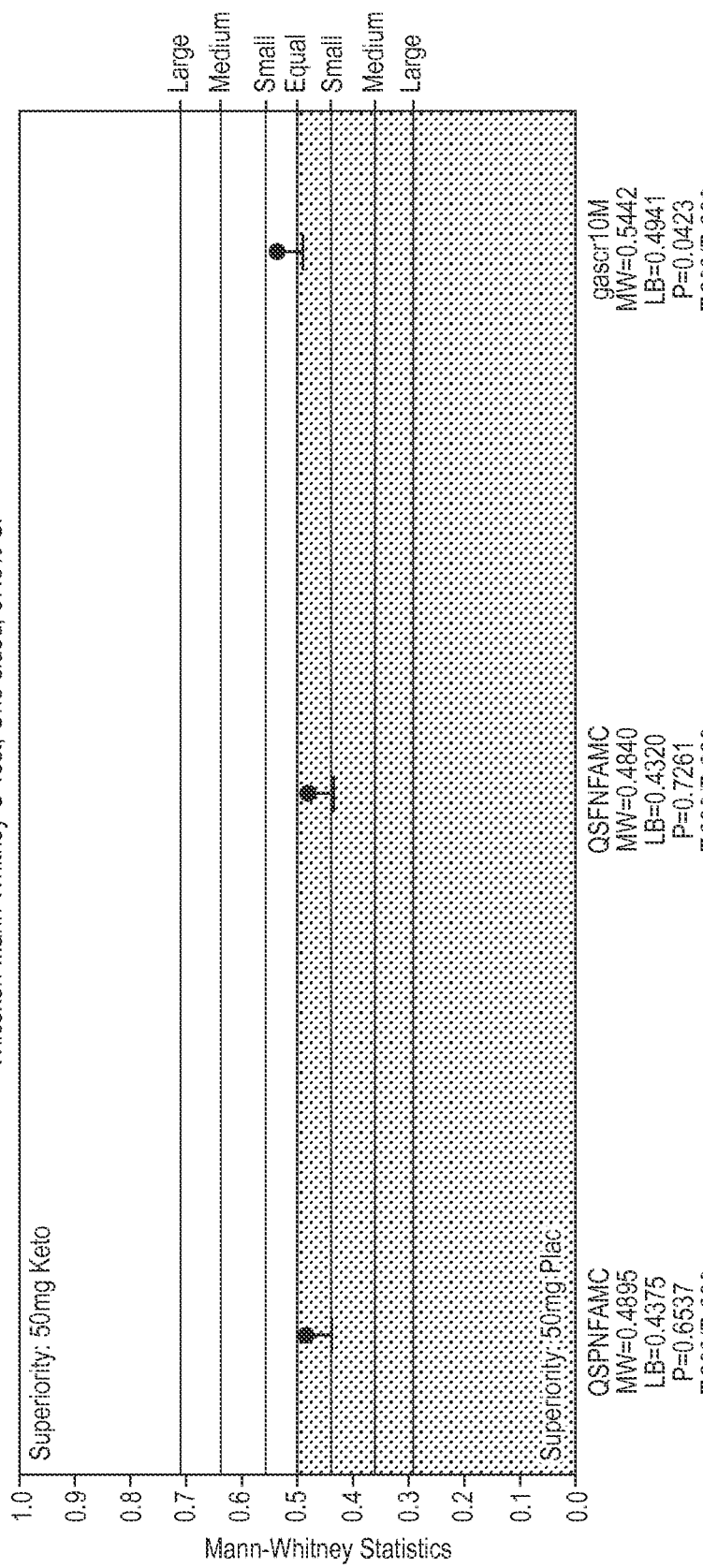
FIG. 9A shows the results of example 2 (European study) and provides Mann-Whitney statistics and continuous responder analysis of pain measurements in patients treated with 50 mg dose of KT and placebo gel, analysed by randomised Wilcoxon-Mann-Whitney-U test.
Figure 9B:
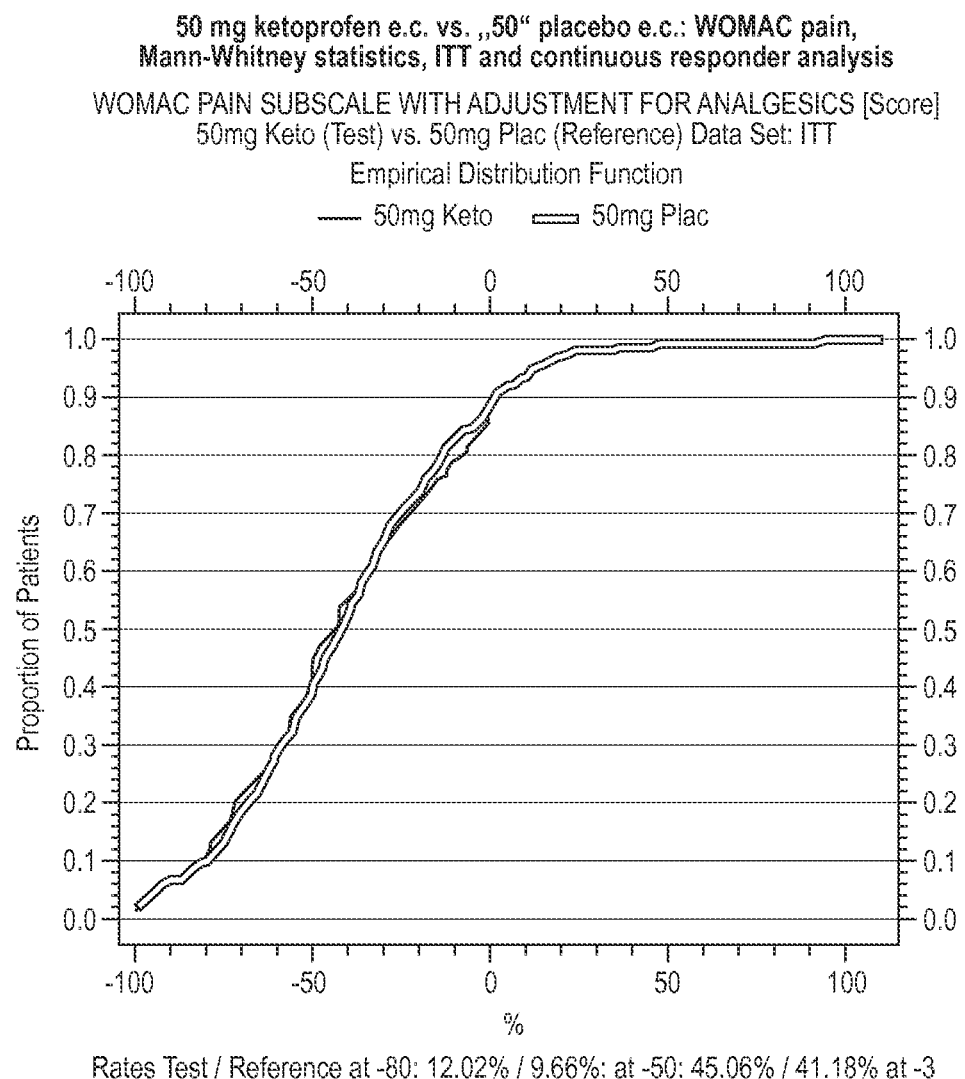
FIG. 9B shows the results of example 2 (European study) and provides Mann-Whitney statistics and continuous responder analysis of pain measurements in patients treated with 50 mg dose of KT and placebo gel analysed by randomised empirical distribution function.
Figure 10:
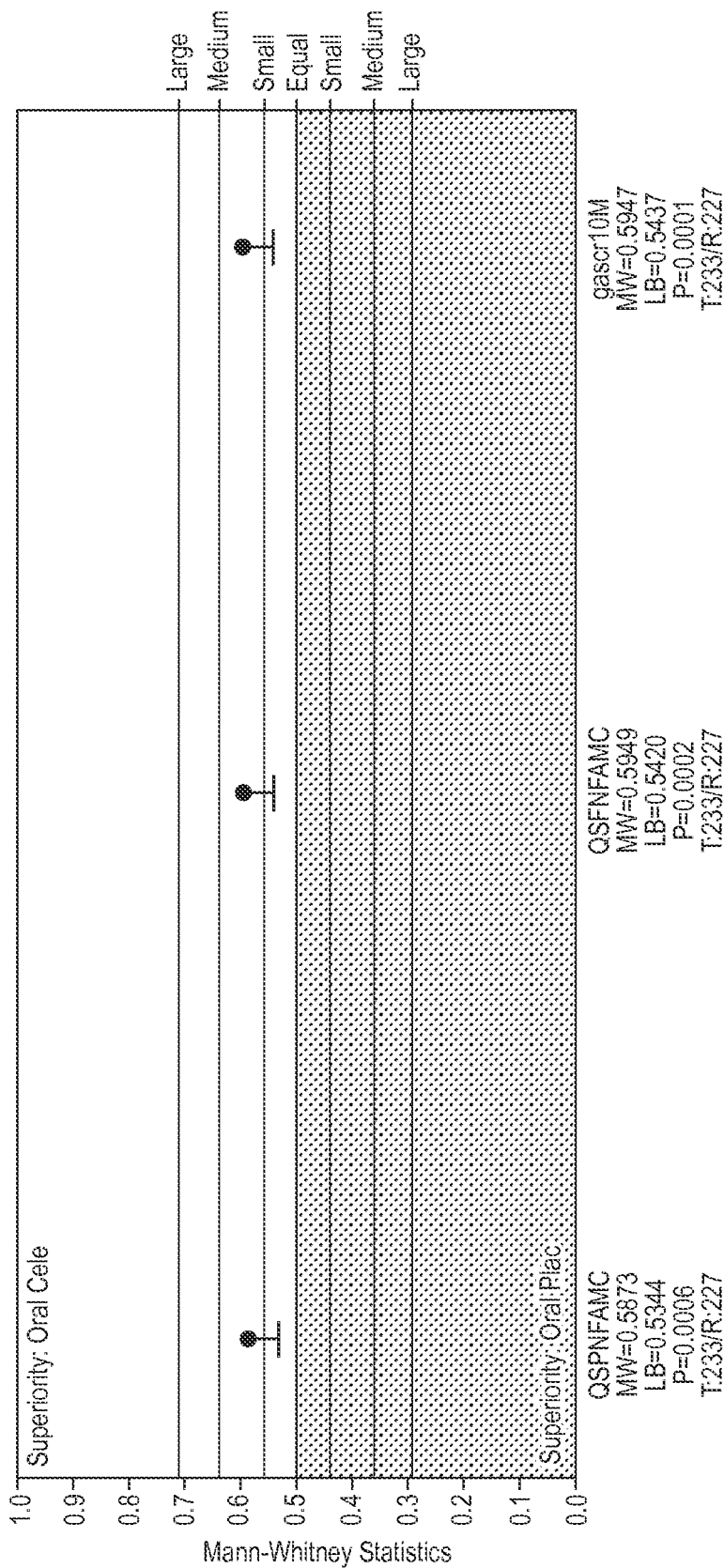
FIG. 10 shows the results of example 2 (European study) and provides Mann-Whitney statistics for 100 mg oral celecoxib capsule (CELEBREX®, Pfizer) and the oral placebo.
Figure 11A:
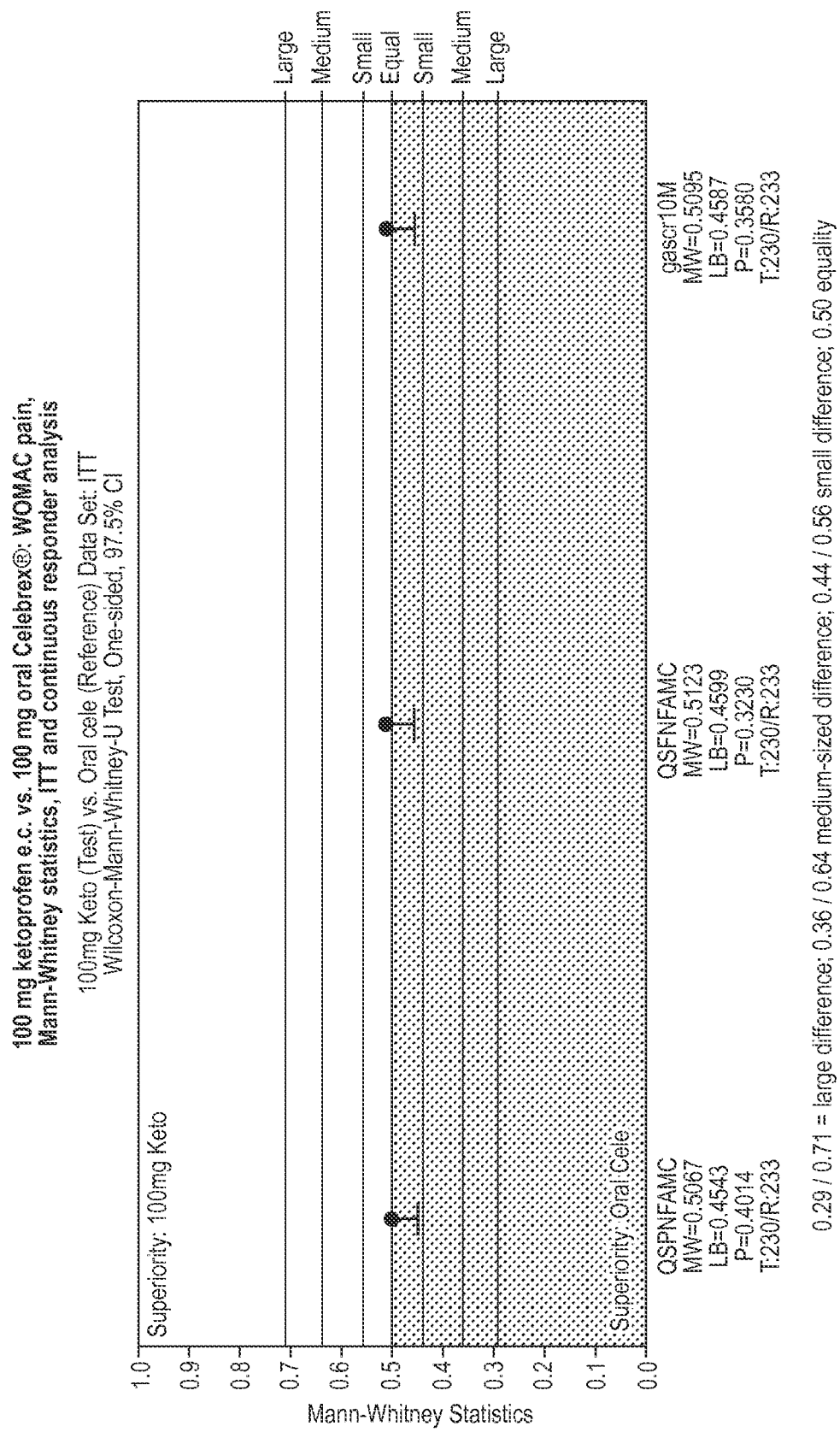
FIG. 11A shows the results that example 2 (European study) and provides WOMAC pain and Mann-Whitney statistics for the 100 mg ketoprofen and 100 mg celecoxib capsule, analysed by randomised Wilcoxon-Mann-Whitney-U test.
Figure 11B:
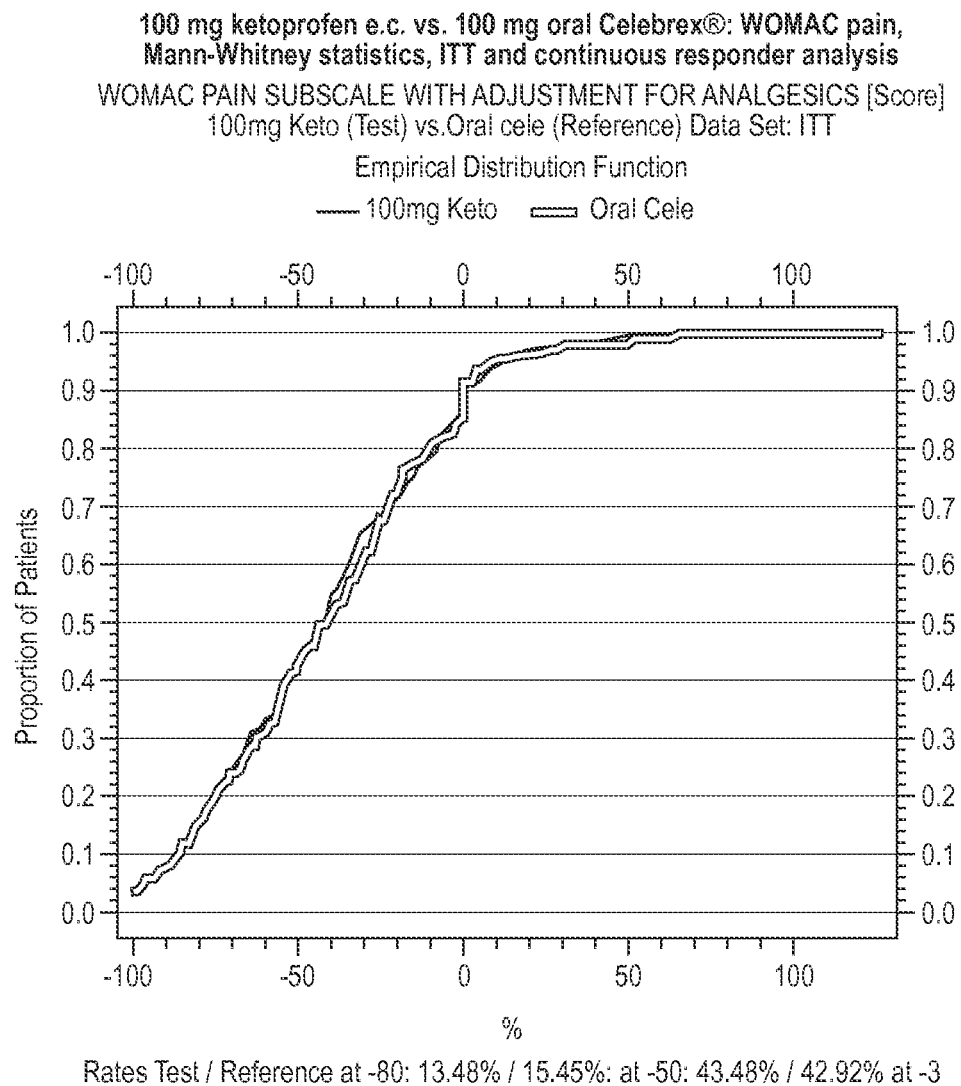
FIG. 11B shows the results that example 2 (European study) and provides WOMAC pain and Mann-Whitney statistics for the 100 mg ketoprofen and 100 mg celecoxib capsule analysed by randomised empirical distribution function.
Figure 12A:
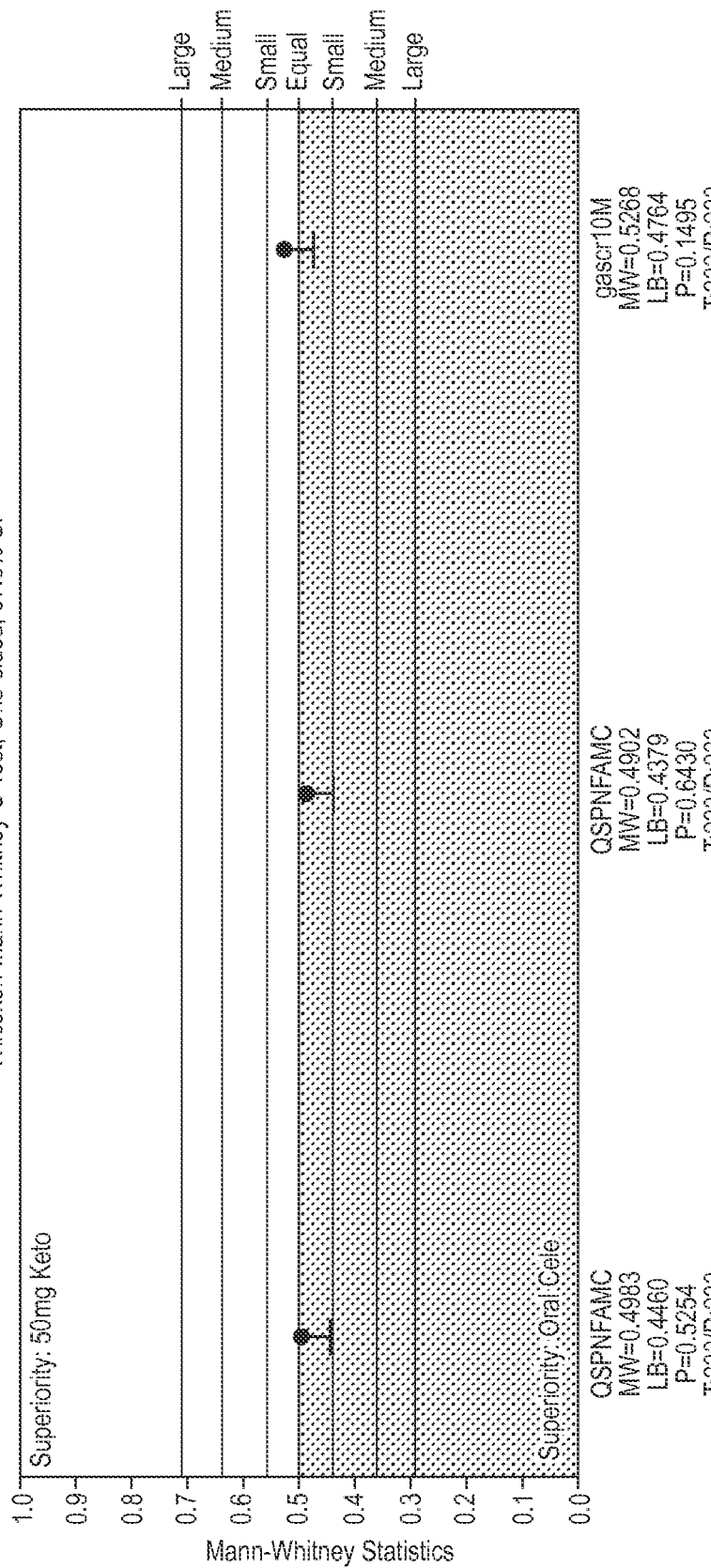
FIG. 12A shows the results of example 2 (European study) and provides Mann-Whitney statistics and continuous responder analysis of pain measurements in patients for the 50 mg dose of KT versus the 100 mg celecoxib capsule (CELEBREX®, Pfizer), analysed by randomised Wilcoxon-Mann-Whitney-U test.
Figure 12B:
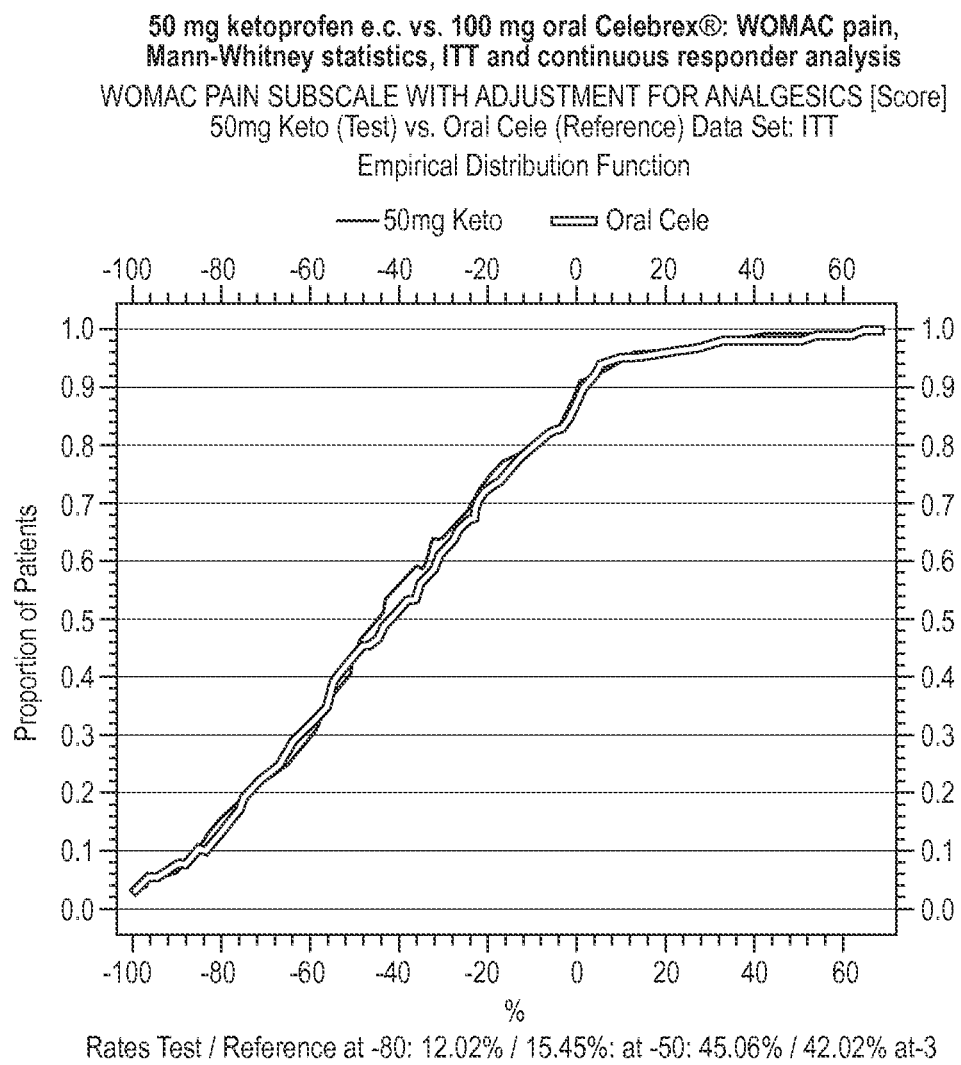
FIG. 12B shows the results of example 2 (European study) and provides Mann-Whitney statistics and continuous responder analysis of pain measurements in patients for the 50 mg dose of KT versus the 100 mg celecoxib capsule (CELEBREX®, Pfizer), analysed by randomised empirical distribution function.
Figure 13:
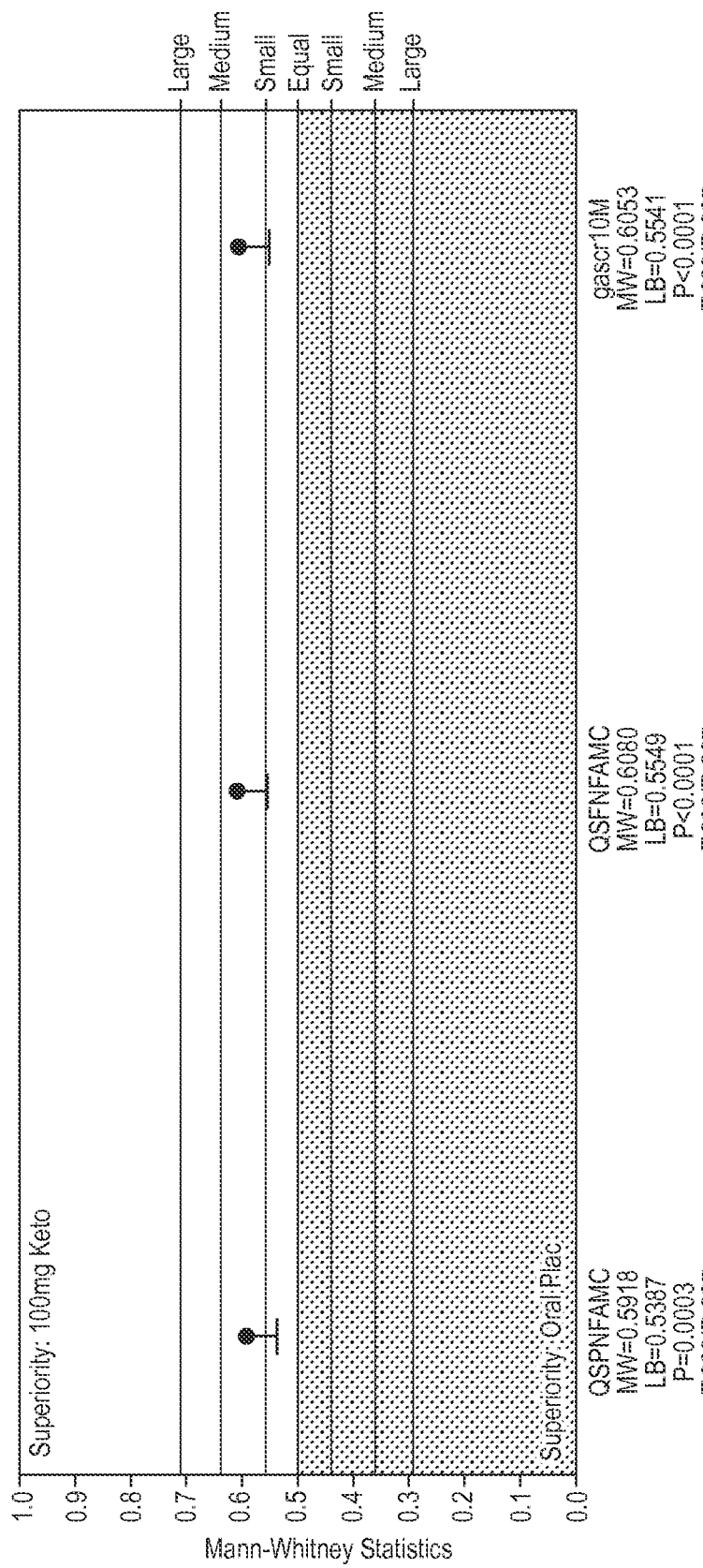
FIG. 13 shows the results of example 2 (European study) and provides Mann-Whitney statistics for the 100 mg dose of KT versus the oral placebo.
Figure 14:
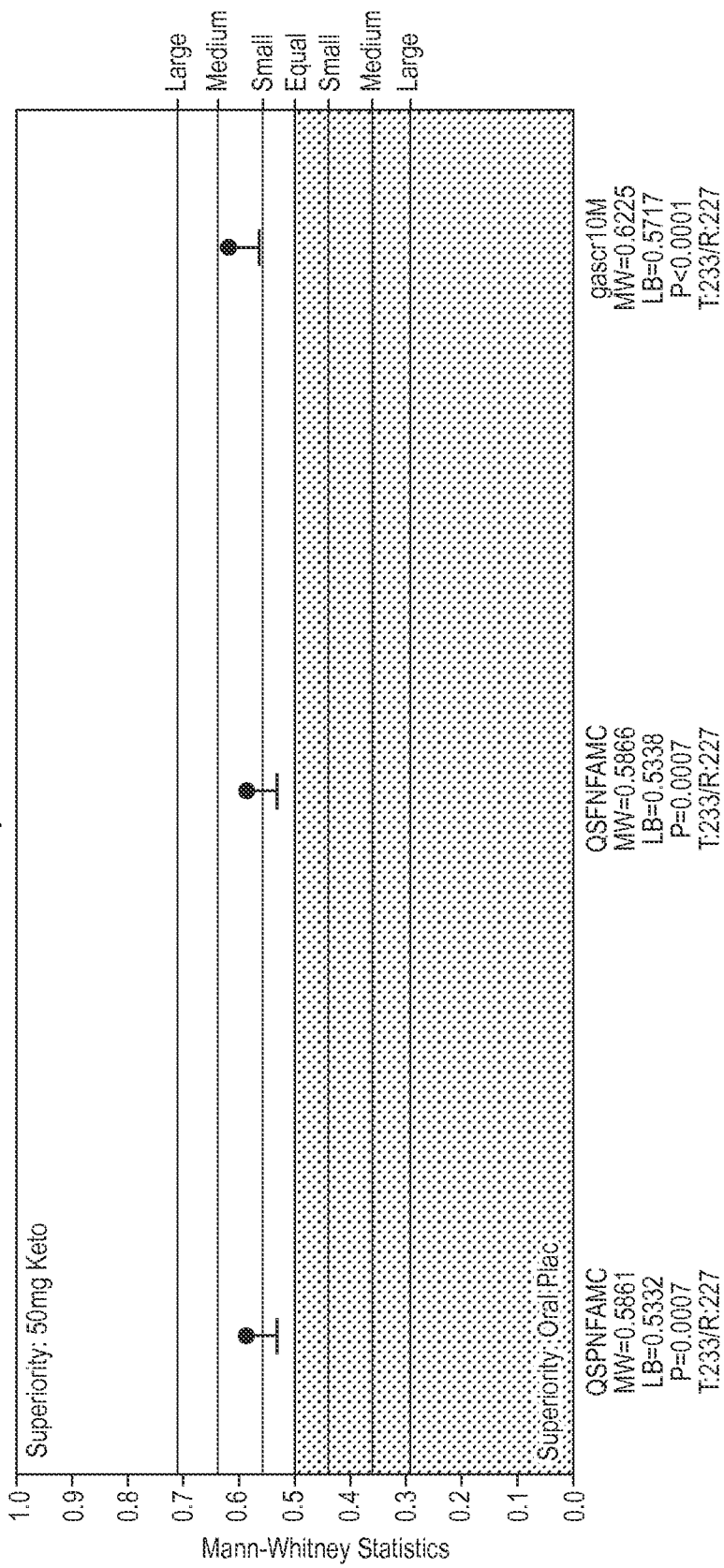
FIG. 14 shows the results of example 2 (European study) and provides Mann-Whitney statistics for the 50 mg dose of KT versus the oral placebo.
Figure 15:
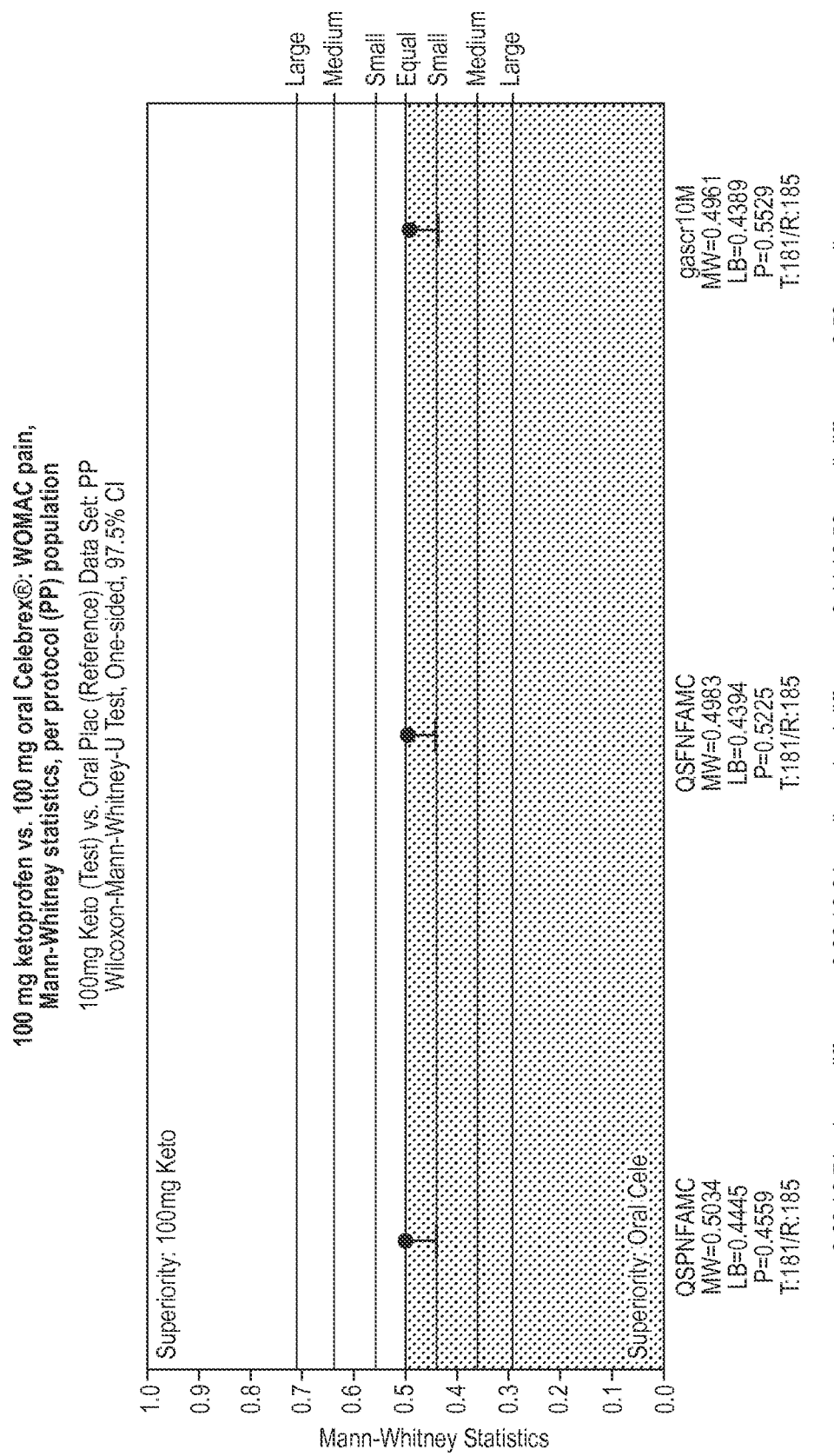
FIG. 15 shows the results of example 2 (European study) and provides Mann-Whitney statistics for the 100 mg dose of KT versus of 100 mg celecoxib capsule (CELEBREX®, Pfizer).
Figure 16:
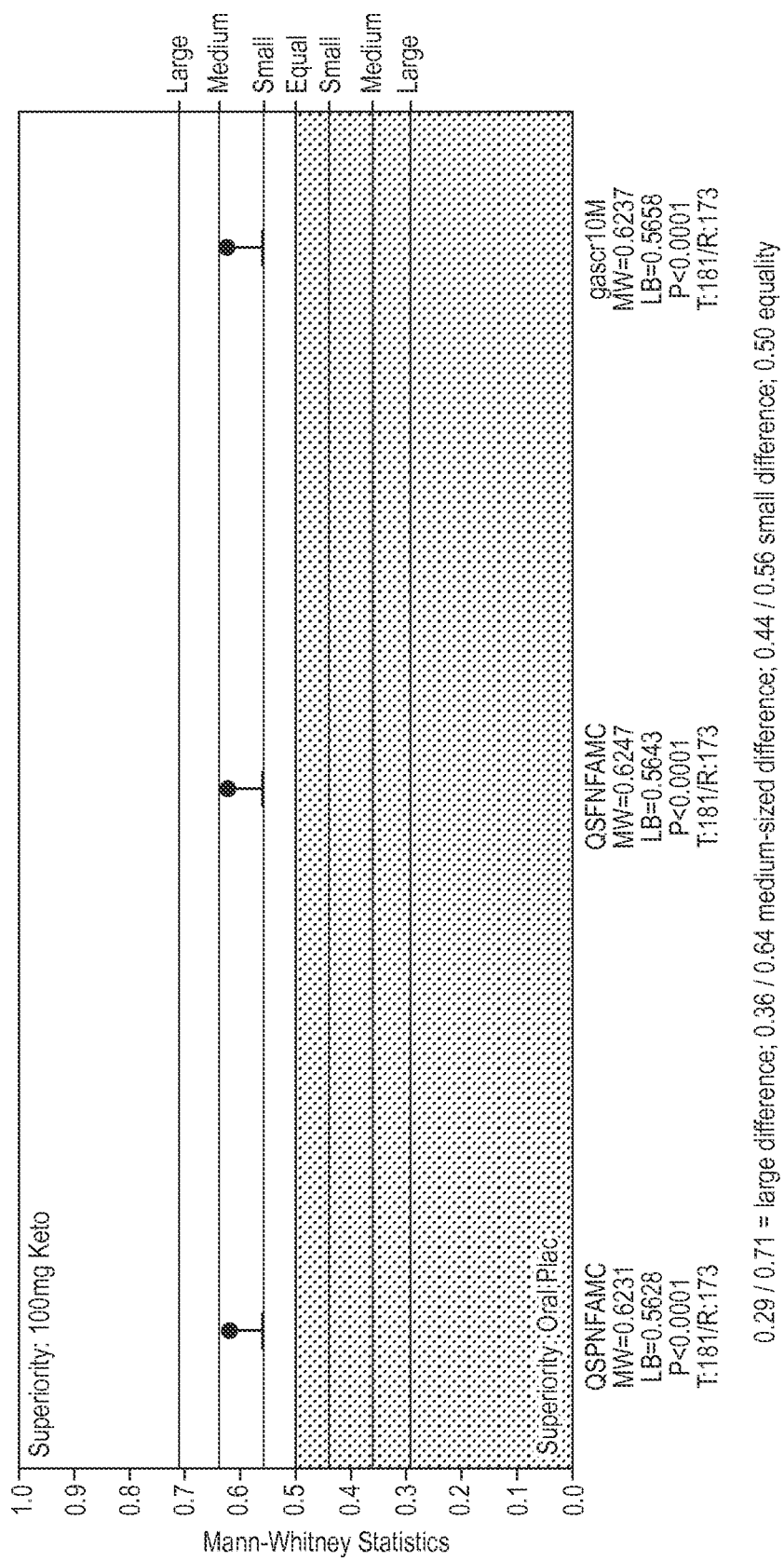
FIG. 16 shows the results of example 2 (European study) and provides Mann-Whitney statistics for the 100 mg of KT versus the oral placebo, using the "per protocol population" instead of "intention to treat" (ITT).

The data from these studies established that the placebo transfersomes (i.e., transfersomes of the technology described herein) were active. Data from the European study are shown in FIGS. 8-17. FIGS. 8-9 show Mann-Whitney statistics and continuous responder analysis of pain measurements in patients, with FIG. 8 showing results for the 100 mg dose of KT and placebo gel and FIG. 9 showing results for the 50 mg dose of KT and placebo gel. FIGS. 10 and 11 show WOMAC pain and Mann-Whitney statistics for the 100 mg celecoxib capsule (CELEBREX®, Pfizer) and the oral placebo. FIG. 12 shows Mann-Whitney statistics and continuous responder analysis of pain measurements in patients for the 50 mg dose of KT vs the 100 mg celecoxib capsule (CELEBREX®, Pfizer). FIG. 13 shows Mann-Whitney statistics for the 100 mg dose of KT vs the oral placebo and FIG. 14 shows Mann-Whitney statistics for the 50 mg dose of KT vs the oral placebo. FIG. 15 shows Mann-Whitney statistics for the 100 mg dose of KT vs 100 mg celecoxib capsule (CELEBREX®, Pfizer). FIG. 16 shows Mann-Whitney statistics for the 100 mg dose of KT vs the oral placebo, using the "per protocol population" instead of "intention to treat" (ITT). FIG. 17 shows possibly treatment related adverse events (Aes) observed in the study.

Inter-Studies Results and Conclusions

Figure 18:
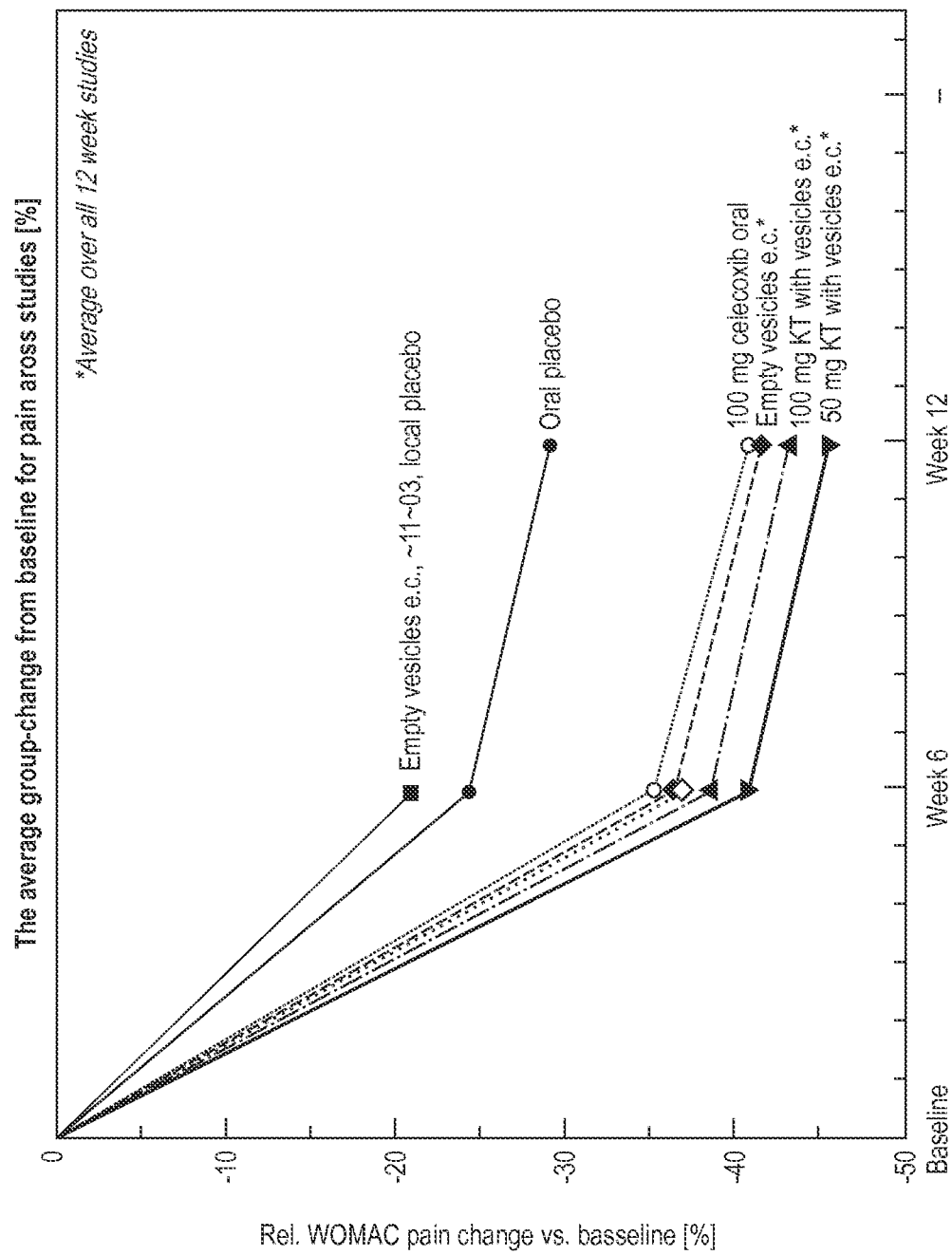
FIG. 18 shows the results of example 2 and combines the results of the US and European studies to show the average group change for the various treatments at week 6 and 12 of the studies.
Figure 19:
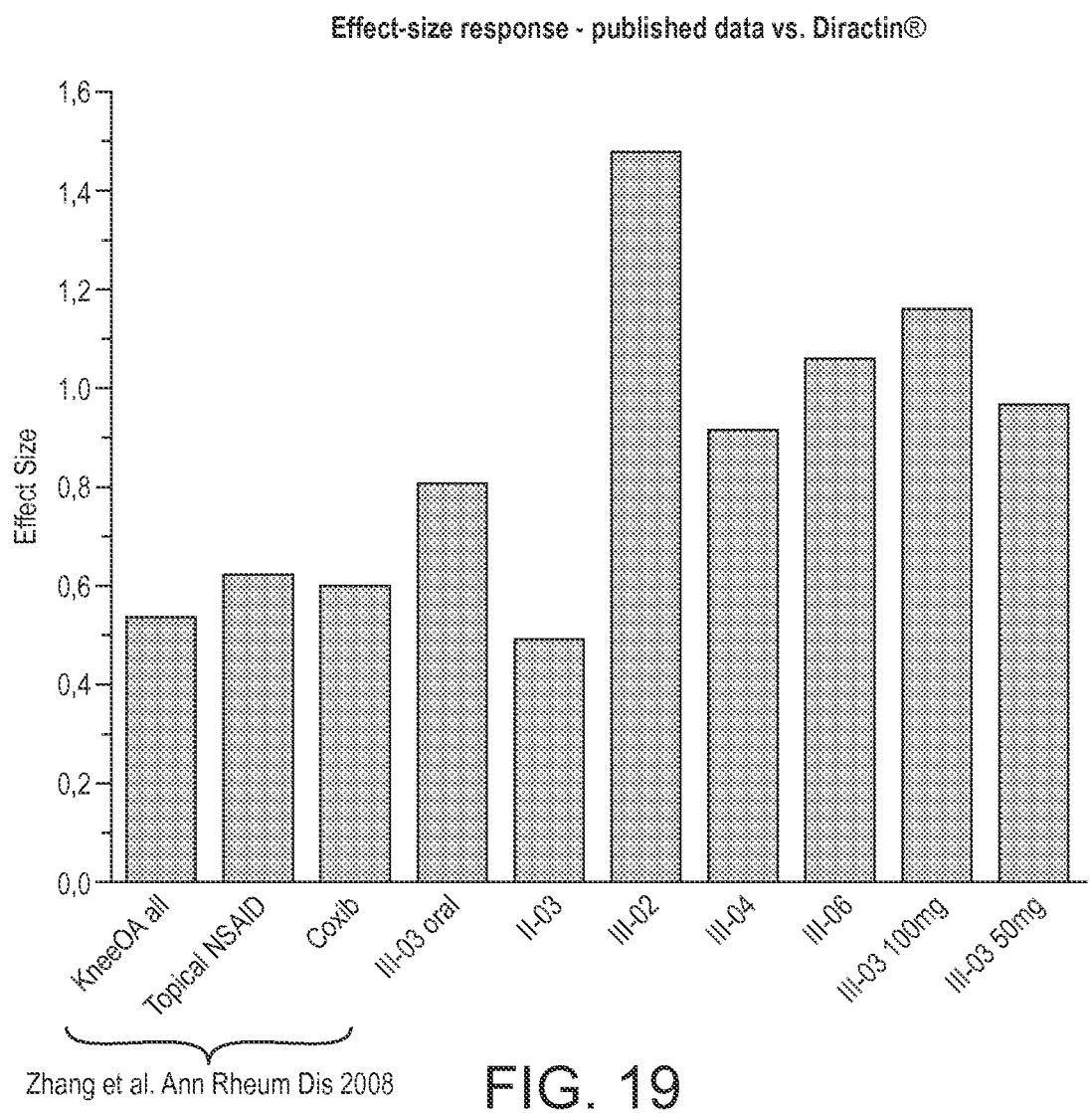
FIG. 19 shows the results of example 2 and combines the results of the US and European studies to show the effect of the placebo response in published data and by the placebo gel that is the subject of the invention.

The combined results of the US and European studies establish that the placebo gel (transfersomes gel) is equivalent or better than the ketoprofen-containing gel, and that each have similar efficacy to oral celecoxib. All three of these products are shown to be superior to oral placebo. The effectiveness of the placebo gel (transfersomes gel) was similar to oral drugs acting on Cox-II but had substantially lower side effects liability. FIG. 18 shows the average group change for the various treatments at week 6 and 12 of the studies. FIG. 19 shows the effect of the placebo response in published data and by the placebo gel that is the subject of the invention.

Example 3

Clinical Trials for Transfersomes for Inflammatory Dermatoses

A multicentre, randomized, double-blind, placebo-controlled study of safety and efficacy of IDEA-070 (transfersome spray containing ketoprofen) was conducted in the Germany for the treatment of inflammatory dermatological diseases. The study was conducted from Q1/2005 to Q4/2005 and included 240 patients in 7 study centres. The target indications for the study were atopic eczema, dishydrotic hand eczema, plaque type psoriasis, seborrheic eczema, and acne vulgaris. The treatment group used in the study received 0.24 mg ketoprofen per $cm^2$ skin in IDEA-070 spray, e.c., b.i.d. and the controls received a topical placebo (randomisation: IDEA-070/placebo: 2/1). Transfersomes used in this study were made in accordance with transfersomes as described herein. The primary objectives of the study were to evaluate the effects of IDEA-070 compared to a placebo in patients with atopic eczema, dishydrotic hand eczema, plaque type psoriasis, seborrheic eczema, and acne vulgaris using the Investigator Global Assessments score (IGA) and the secondary objectives were to evaluate the efficacy of IDEA-070 compared to a placebo using the Patient Global Assessments score (PGA) and indication specific scores (SCORAD, DASI, PASI, GAGS) as well as to test the safety of IDEA-070.

Patient inclusion in the study required that the patient (1) had one of the following diseases (mild to moderate): atopic eczema, dishydrotic hand eczema, plaque type psoriasis (hyperkeratoses removed before treatment by urea or salicylic acid), seborrheic eczema in the face or head), or acne vulgaris; (2) was aged 18-80 years; and (3) that women of childbearing potential were using a reliable method of contraception. Patients meeting any of the following criteria were excluded from the study: Systemic therapy for skin diseases within 2 weeks prior to start of treatment; UV therapy within 4 weeks prior to start of treatment; Chronic or acute illness requiring systemic antiinflammatory treatment; Skin cancer and precancerous skin lesions; History of peptic ulcers or gastric intolerance with NSAIDs; History of asthma bronchiale; History of chronic airway infection; History of renal insufficiency; Thrombocytopathia; Immunosuppressants (e.g., corticosteroids) within 2 weeks prior to start of treatment; Known sensitisation to NSAIDs; Pregnancy or lactation; Mental disorders.

Table 10 summarizes the study population used in the study.

TABLE 10

|  | Placebo | IDEA-070 | All |
|---|---|---|---|
| Acne | 17 | 33 | 50 |
| Atopic E. | 17 | 31 | 48 |
| Dishydrotic E. | 18 | 34 | 52 |
| Psoriasis | 16 | 35 | 51 |
| Seborrheic E. | 14 | 34 | 48 |
|  |  | Total | 249 |

Figure 20:
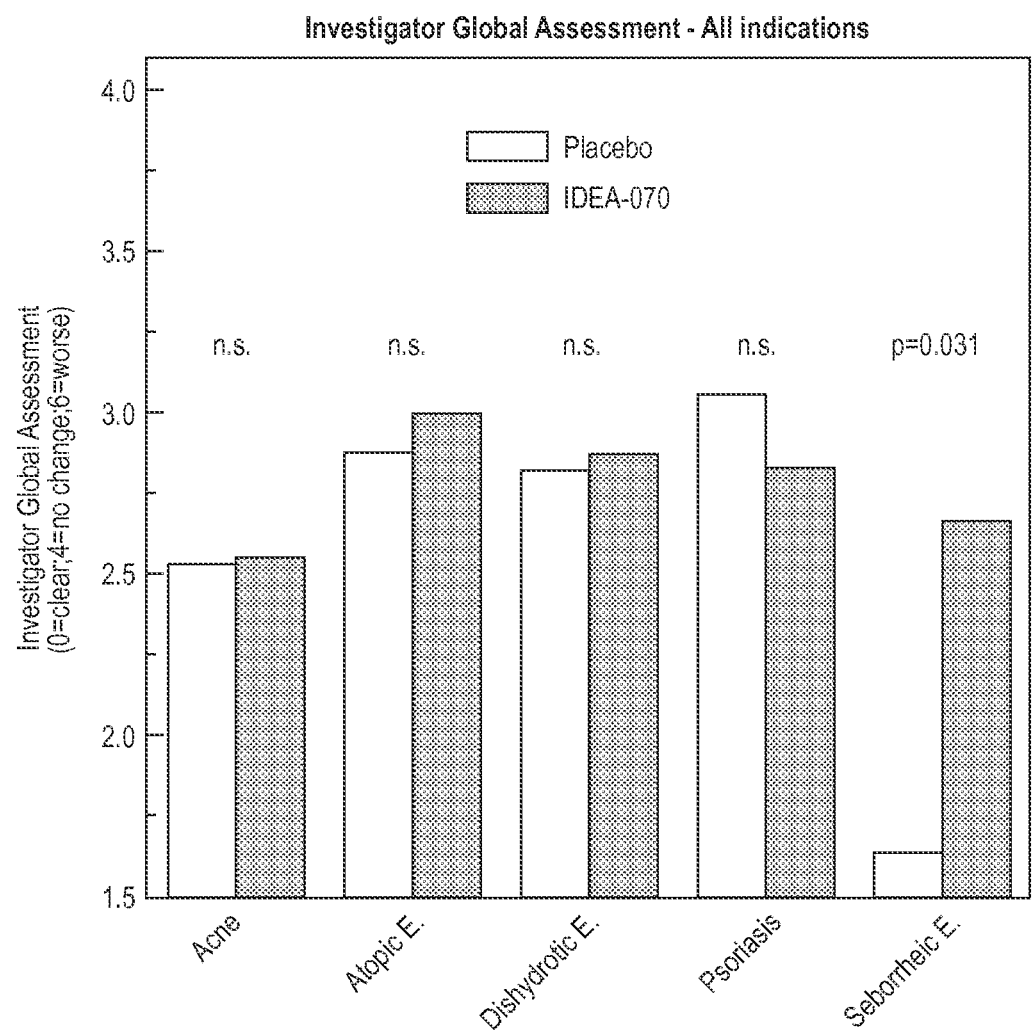
FIG. 20 shows the results of example 3 and provides the investigator global assessment score (IGA) for the five main objective indications.
Figure 21:
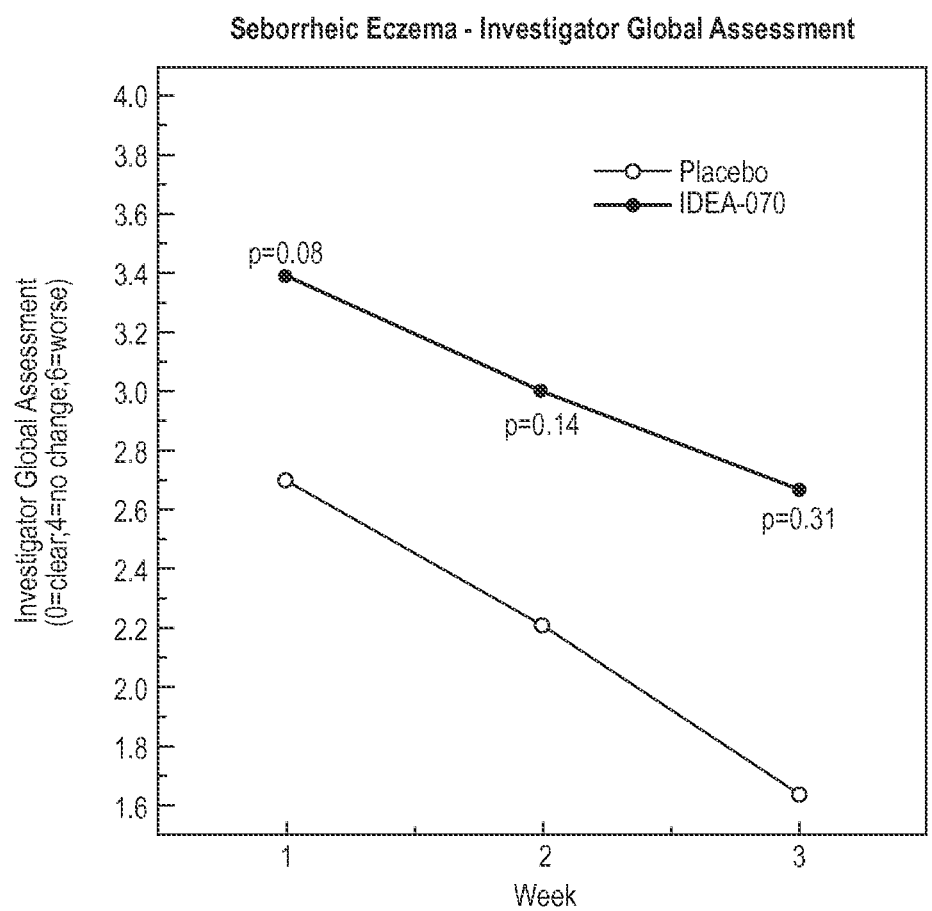
FIG. 21 shows the results of example 3 and provides the IGA score for Seborrheic Eczema.
Figure 22:
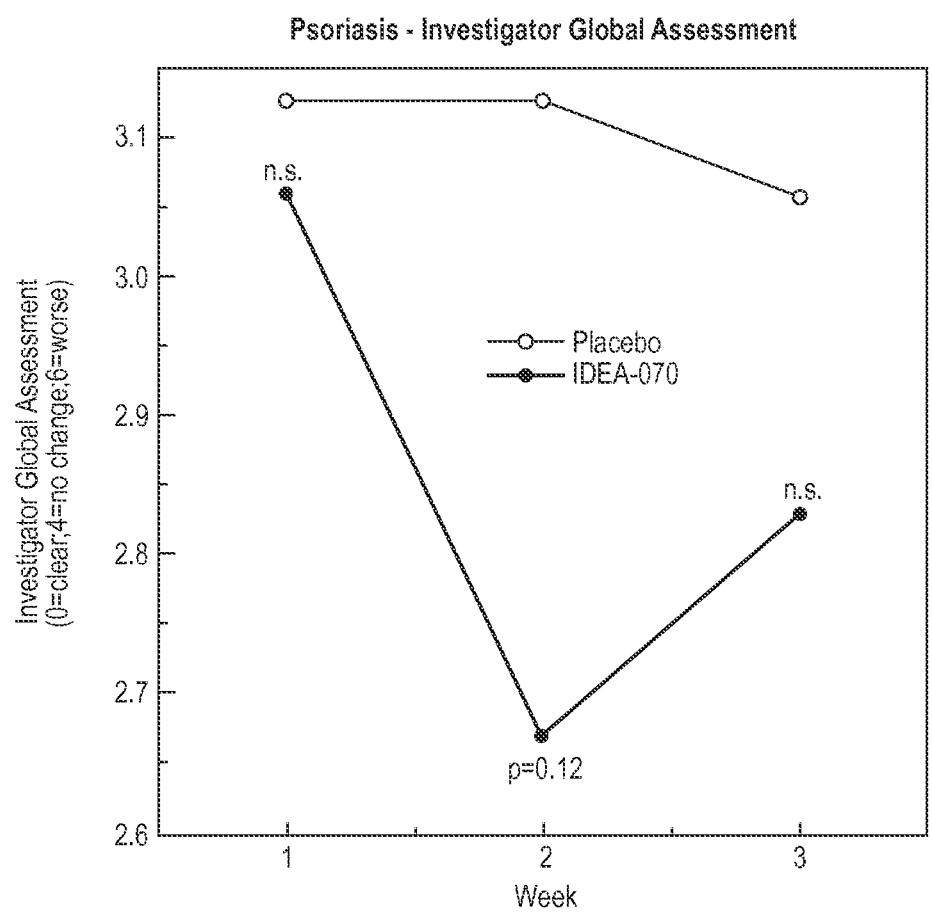
FIG. 22 shows the results of example 3 and provides the IGA score for Psoriasis.
Figure 23:
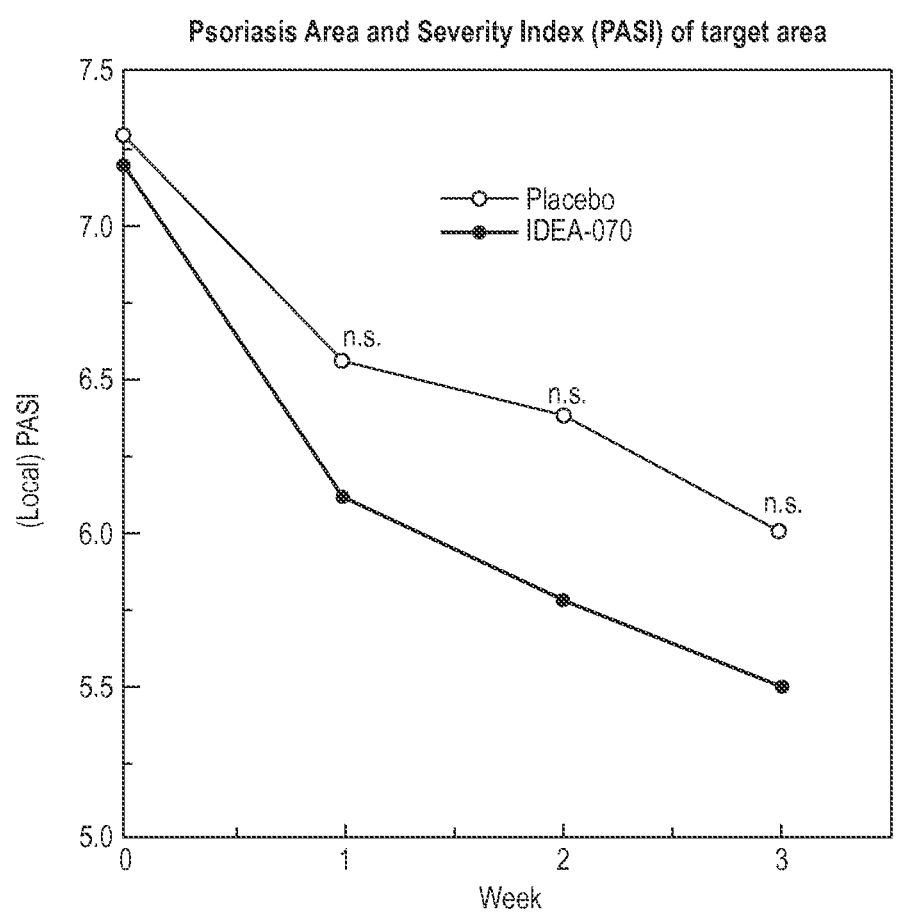
FIG. 23 shows the results of example 3 and provides the Psoriasis area and severity index (PAST) of the area targeted by the transfer zones.
Figure 24:
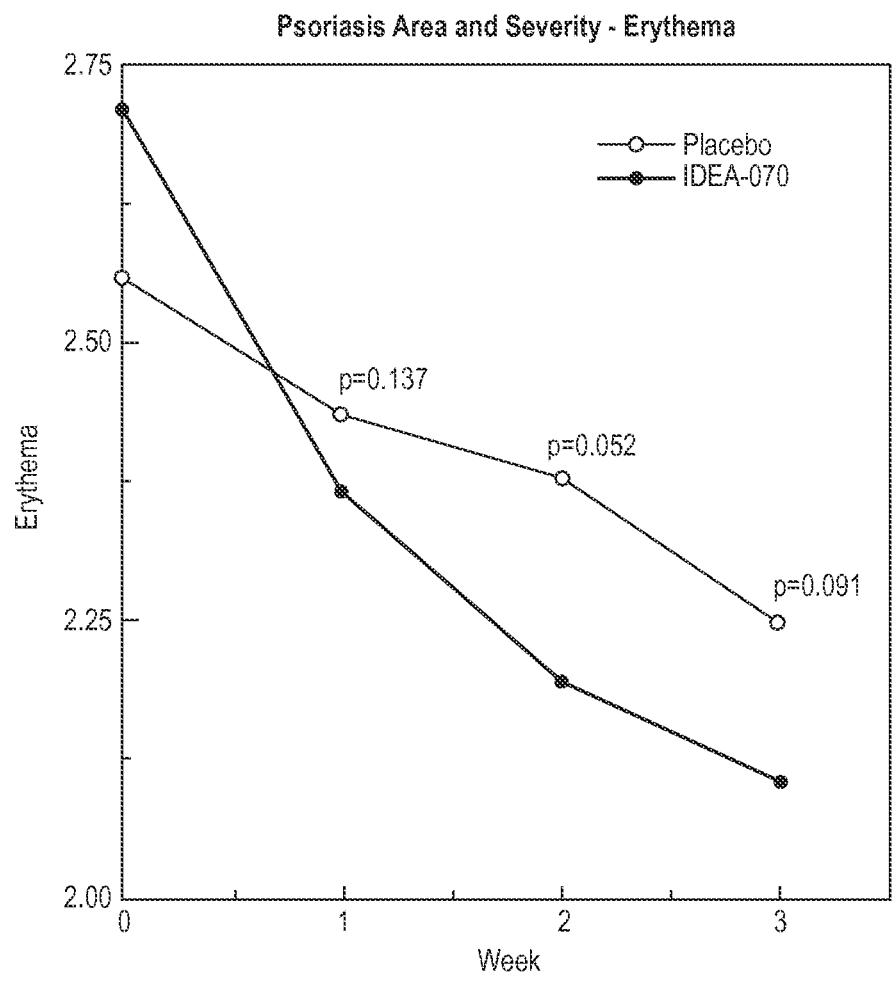
FIG. 24 shows the results of example 3 and provides the IGA score for Erythema.

The data from these studies established that the placebo transfersomes (i.e., transfersomes of the technology described herein) were active. FIGS. 20-23 provide results of the study. FIG. 20 shows the IGA score for the five main objective indications. As shown of FIG. 20 there was no significant difference between IDEA-070 and placebo for any of the indications except for seborrheic eczema, in which the placebo gel showed a more marked improvement that TDT 070 with a p value of p=0.031. FIGS. 21-23 show the IGA scores at week 1, 2 and 3 for seborrheic eczema, psoriasis, psoriasis area and severity index (PAST), and erythema, respectively.

Adverse events by indication observed in the study are shown in Table 11.

TABLE 11

|  | Placebo | IDEA-070 |
|---|---|---|
| Akne | 17.6% | 24.2% |
| Atopic E. | 41.2% | 32.3% |
| Dishydrotic E. | 16.7% | 20.6% |
| Psoriasis | 12.5% | 25.7% |
| Seborrheic E. | 7.1% | 23.5% |
| All | 19.5% | 25.1% |

Adverse events by system organ class-skin and subcutaneous tissue are shown in Table 12.

TABLE 12

|  | Placebo | IDEA-070 |
|---|---|---|
| Akne | 0 | 1 |
| Atopic E. | 0 | 5 |

TABLE 12-continued

|  | Placebo | IDEA-070 |
|---|---|---|
| Dishydrotic E. | 0 | 1 |
| Psoriasis | 1 | 4 |
| Seborrheic E. | 0 | 0 |
| All | 1 | 11 |

Example 4

Sequestration of Arachadonic Acid

Assays were performed to assess the effect of transfersomes arachadonic acid sequestration. The assays used in these studies involved using arachidonic acid as a substrate and measuring cylcooxygenase activity as an indicator of arachidonic acid sequestration Other assays could be used to measure/analyze arachidonic acid sequestration. For example sequestration could be measured using radiolabeled arachidonic acid (or another lipid), adding the transfersomes to sequester the lipid, centrifuging to separate the transfersomes (or using another method of separating transfersomes, such as filtration) and measuring the radiolabeled lipid in the transfersomes as an indicator of sequestration.

Transfersomes used in this study were made in accordance with the transfersomes described herein.

Figure 25:
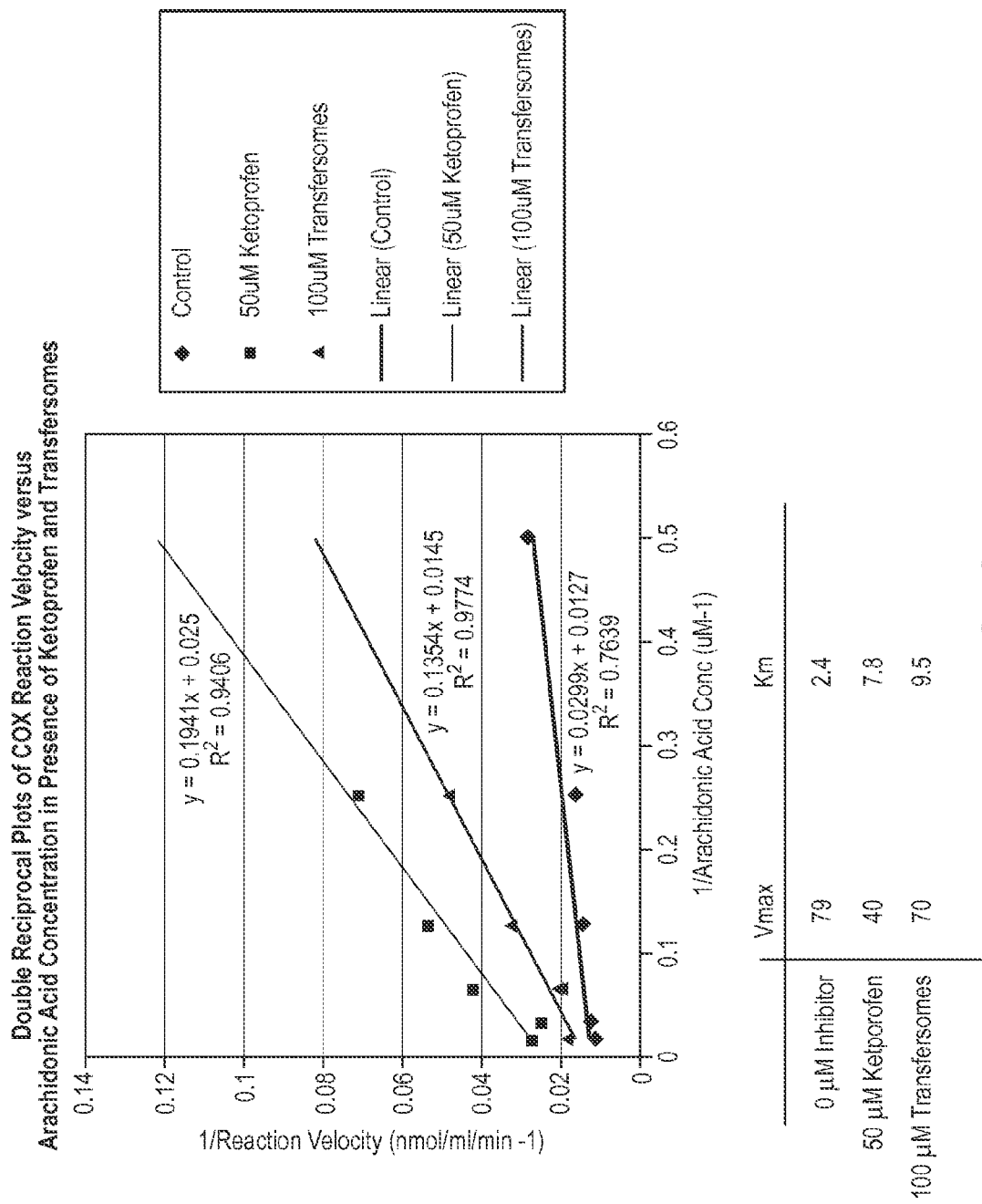
FIG. 25 shows the results of example 4 and provides a double reciprocal plot of COX reaction velocity versus Arachidonic acid concentration for a control, 50 mg ketoprofen and 100 mg transfersomes.
Figure 26:
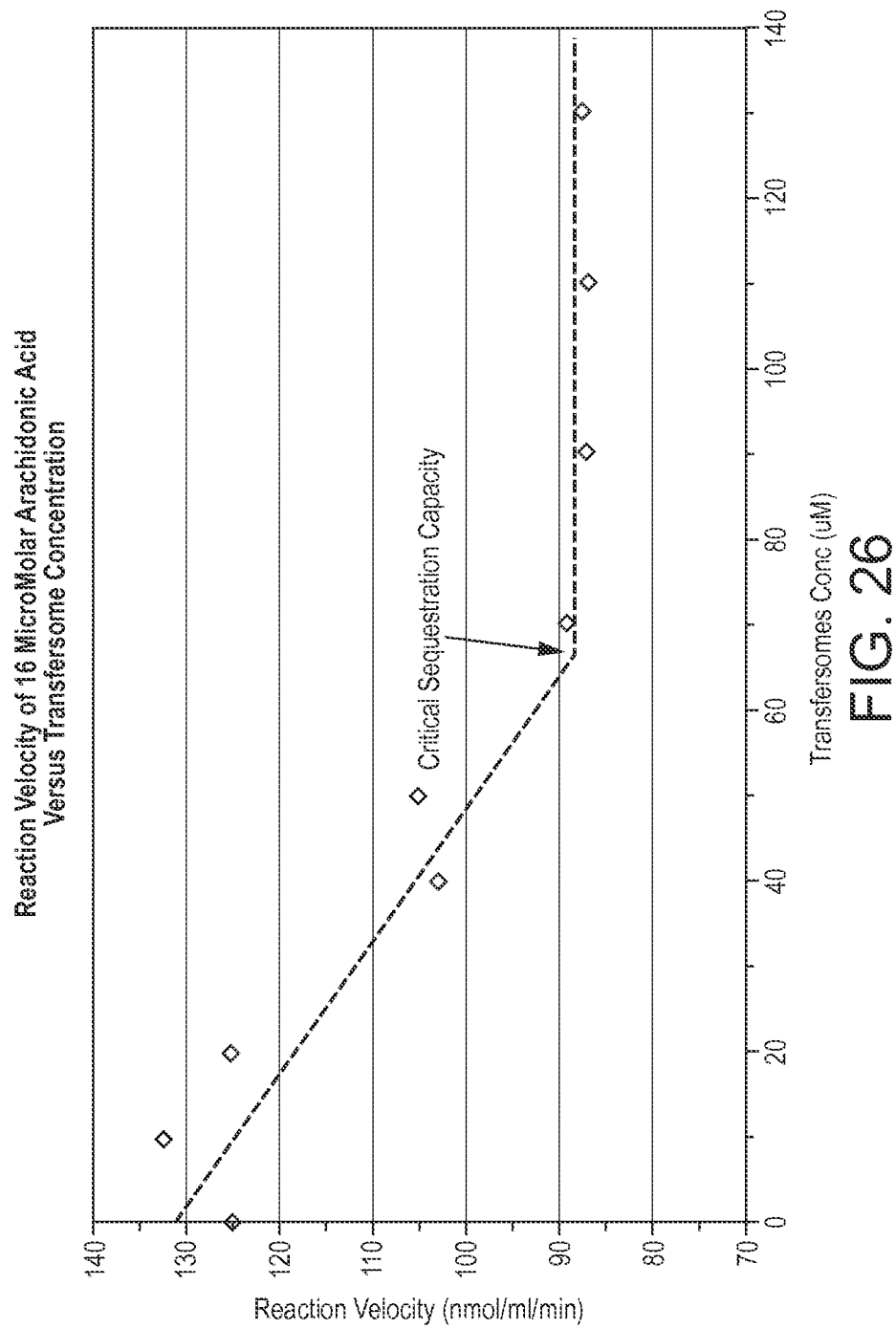
FIG. 26 shows the results of example 4 and provides the COX reaction velocity using 16 mg Arachidonic acid and increasing amounts of transfer zones.

Representative results from the COX inhibition/Sequestration assays are shown in FIGS. 25-26. FIG. 25 shows a double reciprocal plot of COX reaction velocity versus arachidonic acid concentration for a control, 50 µM ketoprofen and 100 µM transfersomes. The differences between the results of the control and the 100 µM transfersomes indicate sequestration of the arachidonic acid substrate. FIG. 26 shows the COX reaction velocity using 16 µM arachidonic acid and increasing amounts of transfersomes. The saturation at between 50-70 µM transfersomes suggests that the critical sequestration capacity of the transfersomes occurs in this range (as marked on the figure).

Example 5

Sequestration of Other Lipids

Assays are performed to assess the effect of transfersomes on other lipids. Other lipids include cholesterol, mediators of pain and inflammation (e.g., such as prostaglandins, prostaglandin precusrsors and leukotrienes. The transfersomes are effective in sequestering identified lipids.

The invention claimed is:

1. A method for the treatment of inflammatory dermatoses disorders or fungal infection comprising topically administering to a subject having an inflammatory dermatoses disorder a vesicular formulation comprising one or more phospholipids and one or more non-ionic surfactants, wherein the vesicular formulation comprises vesicles having a lipid bilayer in aqueous media and does not include a pharmaceutically active agent.

2. The method of claim 1, wherein the inflammatory dermatoses disorder is selected from the group consisting of: atopic eczema, dishydrotic hand eczema, plaque psoriasis, seborrheic eczema, erythema, and acne vulgaris.

3. The method of claim 1, wherein the formulation is a cream, lotion, ointment, gel, solution, spray, lacquer or film forming solution.

4. The method of claim 1, wherein the molar ratio of phospholipid to surfactant is about 1:3 to about 30:1.

5. The method of claim 1, wherein the formulation contains 2.0-10.0% by weight phospholipid.

6. The method of claim 1, wherein the formulation contains 0.2-5.0% by weight surfactant.

7. The method of claim 1, wherein the formulation contains 0.2% to about 0.5% by weight surfactant.

8. The method of claim 1, wherein the phospholipid is phosphatidylcholine.

9. The method of claim 1, wherein the surfactant is a nonionic surfactant selected from the group consisting of: polyoxyethylene sorbitans, polyhydroxyethylene stearates or polyhydroxyethylene laurylethers.

10. The method of claim 1, wherein the surfactant is polysorbate 80 (Tween 80).

11. The method of claim 1, wherein the inflammatory dermatoses disorder is plaque type psoriasis.

12. The method of claim 1, wherein the inflammatory dermatoses disorder is acne vulgaris.

13. The method of claim 1, wherein the inflammatory dermatoses disorder is erythema.

14. The method of claim 1, wherein the inflammatory dermatoses disorder is atopic eczema.

15. The method of claim 1, wherein the formulation is a gel.

16. The method of claim 1, wherein the formulation is a cream.

17. The method of claim 1, wherein the formulation is a spray.

18. The method of claim 1, wherein the formulation is 4-10% by weight phosphatidylcholine and 0.2-5% by weight polysorbate 80 (Tween 80).

19. The method of claim 1, wherein the surfactant is a polyoxyethylene sorbitan.

20. The method of claim 1, wherein the surfactant is a polyhydroxyethylene stearate.

* * * * *